US009790483B2

(12) United States Patent
Raines et al.

(10) Patent No.: US 9,790,483 B2
(45) Date of Patent: Oct. 17, 2017

(54) REAGENTS AND METHODS FOR ESTERIFICATION

(71) Applicant: WISCONSIN ALUMNI RESEARCH FOUNDATION, Madison, WI (US)

(72) Inventors: Ronald T. Raines, Madison, WI (US); Kalie Mix, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/093,510

(22) Filed: Apr. 7, 2016

(65) Prior Publication Data
US 2016/0297752 A1 Oct. 13, 2016

Related U.S. Application Data

(60) Provisional application No. 62/145,193, filed on Apr. 9, 2015, provisional application No. 62/319,153, filed on Apr. 6, 2016.

(51) Int. Cl.
C12N 9/96 (2006.01)
C07C 231/12 (2006.01)
C07C 319/12 (2006.01)
C07D 207/46 (2006.01)
C07K 1/13 (2006.01)
C07C 269/06 (2006.01)
C07C 245/18 (2006.01)

(52) U.S. Cl.
CPC .............. *C12N 9/96* (2013.01); *C07C 231/12* (2013.01); *C07C 245/18* (2013.01); *C07C 269/06* (2013.01); *C07C 319/12* (2013.01); *C07D 207/46* (2013.01); *C07K 1/13* (2013.01)

(58) Field of Classification Search
CPC ... C07C 251/24; C07C 231/12; C07C 319/12; C12N 9/96; C07D 207/46
See application file for complete search history.

(56) References Cited

U.S. PATENT DOCUMENTS

| 8,350,014 | B2 | 1/2013 | Raines et al. |
| 8,871,916 | B2 | 10/2014 | Raines et al. |
| 2016/0067342 | A1 | 3/2016 | Raines et al. |

OTHER PUBLICATIONS

Ibata et al. ("The Acid-catalyzed Decomposition of Diazo Carbonyl Compounds. II. Synthesis of 2- or 5-Heteroatom-substituted Oxazoles" Bull. Chem. Soc. Jpn., 57, 1984, 2450-2455).*
Aboderin A. A. et al. (1965) "Benzhydryl Esters of Amino Acids in Peptide Synthesis," J. Am. Chem. Soc. 87(23): 5469-5472.
Aboderin A. A et al. (1966) "Inactivation of Chymotrypsin by Diphenyldiazomethane," PNAS (USA) 56:1252-1259.
Andersen K. et al. (Feb. 6, 2015) "Diazo Groups Endure Metabolism and Enable Chemoselectivity in Cellulo," J. Am. Chem. Soc. 137:2412-2415.
Bräse et al. (2005) "Organic azides: an exploding diversity of a unique class of compounds," Angew. Chem. Int. Ed. 44:5188-5240.
Buck, R. T. et al. (2002) "N—H insertion reactions of rhodium carbenoids. Part 4. New chiral dirhodium(II) carboxylate catalysts," ARKIVOC (Gainesville, FL, United States) [online computer file] (2002), (8), 16-33.
Bui-Nguyen et al. (1980) "Substituent and isotope effects on the hydrolysis rates of 2-aryl-2-diazocarboxylic esters," Helv. Chimica Acta 63(1) 63-75.
Chang, J.A. and Kresge, A.J. (2003) "Kinetics and mechanism of acid-catalyzed hydrolysis of the diazo functional group of diazophenylacetamide," J. Phys. Org. Chem. 16(9):598-602.
Chiang Y. et al. (2003) "The Mandelamide Keto-Enol System in Aqueous Solution. Generation of the Enol by Hydration of Phenylcarbamoylcarbene," J. Amer. Chem. Soc. 125(1):187-194.
Chibnall et al. (1958) "Studies on the amide and C-terminal residues in proteins. 3. The esterification of proteins," Biochem. J. 68:114-118.
Chou et al. (Sep. 23, 2013) "Conversion of Azides into Diazo Compounds in Water," J. Am. Chem. Soc. 135:14936-14939.
De et al. (2009) "Solvent-Promoted and -Controlled Aza-Michael Reaction with Aromatic Amines," J. Org. Chem. 74:6260-6265.
Delpierre et al. (1965) "Inactivation of pepsin by diphenyldiazomethane," Proc. Natl. Acad. Sci. USA. 54:1161-1167.
Doscher et al. (1961) "Chemical derivatives of alpha-chymotrypsinogen IV. A comparison of the reactions of alpha-chymotrypsinogen and of simple carboxylic acids with diazoacetamidem," J. Biol. Chem. 236:1328-1337.
Doyle (1986) "Catalytic methods for metal carbene transformations," Chem. Rev. 86:919-939.
Dumitrescu et al. (Jan. 19, 2011) "Nonmetal Catalyzed Insertion Reactions of Diazocarbonyls to Acid Derivatives in Fluorinated Alcohols," Org. Lett. 13:692-695.

(Continued)

Primary Examiner — Yong Chong
(74) Attorney, Agent, or Firm — Lathrop Gage LLP

(57) ABSTRACT

Methods and reagents for esterification of biological molecules including proteins, polypeptides and peptides. Diazo compounds of formula I:

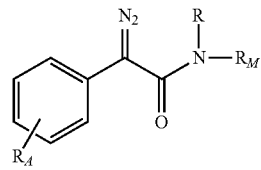

where R is hydrogen, an alkyl, an alkenyl or an alkynyl, $R_A$ represents 1-5 substituents on the indicated phenyl ring and $R_M$ is an organic group, which includes a label, a cell penetrating group, a cell targeting group, or a reactive group or latent reactive group for reaction to bond to a label, a cell penetrating group, or a cell targeting group, among other organic groups are useful for esterification of biological molecules. Also provided are diazo compounds which are bifunctional and trifunctional coupling reagents as well as reagents for the synthesis of compounds of formula I.

17 Claims, 9 Drawing Sheets

(56) References Cited

OTHER PUBLICATIONS

Friedrich E.C. and Taggart D. B. (1978) "Comparisons of the Inden-1-yl, Fluoren-9-yl, and Cycloprop[2,3]inden-1-yl Cations," J. Org. Chem. 43:805-808.
Froussios et al. (1989) "Novelle Methode De Protection Du Carboxyle Des Acid a-Amine: Esters 9-Fluorenyliques," Tetrahedron Letts, 30(26):3413-3414 full reference with English translation.
Fuchs, S.M. and Raines, R.T. (2007) "Arginine Grafting to Endow Cell Permeability" ACS Cell Biology vol. 2(3):167-170.
Furrow et al. (2004) "A general procedure for the esterification of carboxylic acids with diazoalkanes generated in situ by the oxidation of N-tert-butyldimethylsilylhydrazones with (difluoroiodo)benzene," J. Am. Chem. Soc. 126:12222-12223.
Grossberg et al. (1960) "Nature of the Combining Site of Antibody against a Hapten Bearing a Positive Charge," J. Am. Chem. Soc. 82:5478-5482.
Hansch C. et al. (1991) "A Survey of Hammett Substituent Constants and Resonance and Field Parameters," Chem. Rev. 91:165-195.
Jarowicki K. and Kocienski P. (2000) "Protecting Groups," J. Chem. Soc., Perkin Trans. 1, 2000, 2495-2527.
Jewett et al. (2010) "Rapid Cu-Free Click Chemistry with Readily Synthesized Biarylazacyclooctynones," J. Am. Chem. Soc. 132:3688-3690.
Josa-Cullere et al. (Oct. 14, 2014) "Diazo group as a new chemical reporter for bioorthogonal labelling of biomolecules," RSC Adv. 4:52241-52244 (Royal Society of Chemistry).
Larson et al. (1981) "Stabilization of charged substrates by first- and second-row heteroatoms," J. Am. Chem. Soc. 103:410-416.
Lavis L.D. (2008) "Ester Bonds in Prodrugs," ACS Chemical Biol. 3(4):203-206.
Matthews et al. (1975) "Equilibrium acidities of carbon acids. VI. Establishment of an absolute scale of acidities in dimethyl sulfoxide solution," J. Am. Chem. Soc. 97:7006-7014.
McGarrity et al. (1980) "Hydrolysis of diazomethane-kinetics and mechanism," J. Am. Chem. Soc. 102:7303-7308.
McGarrity et al. (1980) "Primary and secondary isotope effects on proton transfers to diazocarbonyl compounds," Helv. Chimica Acta 63(7):1767-78.
McGrath N.A. et al. (Aug. 2, 2012) "Diazo compounds as highly tunable reactants in 1,3-dipolar cycloaddition reactions with cycloalkynes," Chem. Sci. 3:3237-3240.
McGrath, N.A. et al. (Jan. 2015) "Diazo compounds for the bioreversible esterification of proteins," Chem. Sci. 6, 752-755.

Mix K.A. and Raines, R.T. (May 4, 2015) "Optimized Diazo Scaffold for Protein Esterification," Organic Letts. 17:2358-2361.
Mix, K.A. et al. (Oct. 2016) "Diazo Compounds: Versatile Tools for Chemical Biology," ACS Chemical Biology DOI: 10.1021/acschembio.6b00810.
Myers et al. (2009) "A phosphine-mediated conversion of azides into diazo compounds," *Angew. Chem. Int. Ed.* 48:2359-2363.
Novikov M.S. et al. (2015) "Pseudopericyclic 1,5—versus Pericyclic 1,4- and 1,6-Electrocyclization in Electron-Poor 4-Aryl-2-azabuta-1,3-dienes: Indole Synthesis from 2H-Azirines and Diazo Compounds," J. Org. Chem. 80(1) 18-29.
O'Ferrall R.A. M. et al. (1964) "Medium Effects, Isotope Rate Factors, and the Mechanism of the Reaction of Diphenyldiazomethane with Carboxylic Acids in the Solvents Ethanol and Toluene," J. Am. Chem. Soc. 86(24):5553-5561.
Riehm et al. (1965) "Structural Studies of Ribonuclease. XVII. A Reactive Carboxyl Group in Ribonuclease," *Biochemistry*. 4:772-782.
Sakakibara S. (1999) "Chemical Synthesis of Proteins in Solution," Biopolymers (Peptide Science), vol. 51, 279-296.
Shorter, J. (2000) "The Prehistory of the Hammett Equation," Chem. Listy 94:210-214.
Szele et al. (1983) "Reactions of Alkenediazonium Salts. Part 1. 2,2-Diethoxyethene-diazonium hexachloroantimonate: A diazonium, a carbenium or an oxonium salt?" *Helv. Chim. Acta.* 66:1691-1703.
Taft et al. (1988) "Structural and solvent effects evaluated from acidities measured in dimethyl sulfoxide and in the gas phase," Acc. Chem. Res. 21:463-469.
Tian et al. (Mar. 12, 2012) "Selective esterase-ester pair for targeting small molecules with cellular specificity," *Proc. Natl. Acad. Sci. USA.* 109:4756-4761.
Villalgordo, J.M. et al. (1995) "Diazo-transfer reaction with diphenyl phosphorazidate," Helv. Chimica Acta 78(8):1983-1998.
Wang, K. et al. (2007) "Synthesis of tryptamine-substituted alpha-diazo amide derivatives and study of their rhodium-catalyzed cyclization," Hecheng Huaxue 15(4)421-425—English Abstract, Drawings.
Ye et al. (1994) "Organic Synthesis with α-Diazo Carbonyl Compounds," *Chem. Rev.* 94:1091-1160.
International Search Report with Written Opinion corresponding to International Patent Application No. PCT/US2016/026501, mailed Jun. 27, 2016.
T. E. Ballard, Jr., "Small molecule control of biological function," Dissertation submitted to North Carolina State University, 2008.

* cited by examiner

REAGENTS AND METHODS FOR ESTERIFICATION

CROSS-REFERENCE TO RELATED APPLICATIONS

This application claims the benefit of U.S. provisional application 62/145,193 filed Apr. 9, 2015 and U.S. 62/319,153 filed Apr. 6, 2016, each of which is incorporated by reference herein in its entirety.

STATEMENT REGARDING GOVERNMENT SUPPORT

This invention was made with government support under GM044783 and GM007215 awarded by the National Institutes of Health. The government has certain rights in the invention.

BACKGROUND OF THE INVENTION

Chemoselective transformations [1-3] are of key importance in modern chemical biology. Proteins, peptides and amino acids have carboxyl groups in side chains and at the C-terminus. Methods and reagents for selective esterification of such carboxyl groups, particularly those in polypeptides and proteins, which are efficient and give high yield and which can be carried out in buffered aqueous solution are of particular interest. Esterification reactions that do not require a catalyst are also of particular interest. Protein esterification can for example be employed for protein labeling (isotopic, radiolabeling, or fluorescent labeling) and to provide a way to controllably and efficiently increase protein lipophilicity or increase the positive charge on the protein and therefore promote cellular uptake.[20]

It is also of interest for certain applications that the esters formed are "bio-reversible" such that the ester groups are removable by esterases. In a specific application, esterification can be employed to functionalize a protein with moieties that direct the protein towards a particular cell type or and/or which facilitate its cellular uptake. If esterification is bio-reversible, the groups added to target the protein to a cell or to enhance its uptake into the cell can be removed by endogenous enzymes in the cell to regenerate native protein.

Diazo groups are one of the most versatile functional groups in synthetic organic chemistry. [23a-e, 4, 24] It has recently been reported that diazo-compounds can be employed in place of azides as the 1,3-dipole in 1,3-dipolar cycloaddition reactions with alkynes.[4] The rates can greatly exceed those of the analogous azide [4] and the reactions are chemoselective in the presence of mammalian cells.[24] The use of diazo-compounds in such reactions was at least in part made feasible with the availability of methods that convert azides into diazo-compounds using a phosphinoester. [5] These methods are described in U.S. Pat. No. 8,350,014 which is incorporated by reference herein in its entirety for its description of such methods and diazo-compounds prepared by the methods. In addition, diazo compounds have been used to label proteins via C—H and N—H insertion reactions. [25a,b]

The esterification of carboxylic acids with diazomethane has biological potential, but suffers from non-specific reactivity with the hydroxyl groups tyrosine side chains and the amino groups on lysine side chains.[6] In addition, this process only provides access to methyl esters, which are not particularly useful in biologic systems due to their non-specific lability toward various esterases present in biological milieu. [7] Compounds with targeted specificity for common biologic functional moieties that preclude deleterious side reactions are particularly useful. [8]

Stabilized diazo compounds have found widespread use in synthetic organic chemistry. [9] This is primarily due to their ability to react with carboxylic acids and amides by forming metal carbenoids [10] to facilitate O—H or N—H bond insertion respectively. [11, 12] In an effort to avoid the use of toxic metals, it was reported that fluorous organic solvents [13] were sufficient to help facilitate the reaction due to their high polarity and poor nucleophilicity. [14] Additionally, various non-stabilized diazo compounds generated in situ were shown to be capable of carrying out the esterification of carboxylic acids [15], but their unstable nature limits their biological utility.

Early use of stabilized diazo compounds in a biological context involved adding diazo glycinamide [16], diphenyldiazomethane [17] or diazoacetamide [18, 19] to identify the reactive carboxylic acids on proteins. These methods all required adding a vast excess of the diazo compound and tedious monitoring of reaction pH to achieve modest labeling. Moreover, the reaction was not chemoselective, as amino, sulfhydryl, and phenolic side chains suffered alkylation. Such modifications are potentially deleterious to protein function and not bioreversible. [30]

It has recently been reported that the basicity of 9-diazofluorene endows this diazo compound with the ability to label a carboxyl group of a protein in an aqueous environment. [4] A comparison of the reactivity of 9-diazofluorene with that of N-benzyl-2-diazoacetamide with various carboxylic acids in acetonitrile and acetonitrile/aqueous buffer (3:1v/v) demonstrated that while both diazo compounds gave the desired esters in the organic solvent, only 9-diazofluorene gave the desired ester in aqueous medium. In contrast, diethyl 2-diazomalonate was found to be unreactive for ester formation in the organic or aqueous medium. Reactivity of the diazo compound to form the desired esters in aqueous medium was reported to be associated with the ability of the diazo compound to abstract a proton from a carboxylic acid. Further, this ability to abstract a proton was reported to be associated with the $pK_a$ (as measured in dimethylsulfoxide [21] of the conjugate acid of the organic moiety bonded to the diazo group (e.g., conjugate acids of diethylmalonate ($pK_a$=16.4), fluorene ($pK_a$=22.6) and diethylacetamide ($pK_a$ 35). 9-Diazofluorene was reported to function (at 10 eq) to label on average three of eleven carboxylates in RNase A.

While there has been some success in the development of reagents and methods for the chemoselective generation of biological esters from carboxylic acids for protein labeling and other useful protein modification, there remains a need in the art for more efficient chemoselective esterification reagents for proteins and other biological entities (e.g., nucleic acids) which result in bioreversible ester formation. Additionally, there remains a need in the art for chemoselective esterification reagents that are synthetically amenable to modification with biologically useful entities.

SUMMARY OF THE INVENTION

The invention provides methods and reagents for esterification of biological molecules including proteins, polypeptides and peptides. The invention provides certain diazo compounds of formula I:

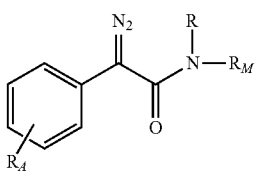

where $R_A$ represents 1-5 substituents on the indicated phenyl ring, R is hydrogen, an alkyl, alkenyl or alkynyl group, and $R_M$ is an organic group, which includes a label, a cell penetrating group, a cell targeting group, or a reactive group or latent reactive group for reaction to bond to a label, a cell penetrating group, or a cell targeting group, among other organic groups. $R_M$ optionally includes a spacer or linker group. In a specific embodiment, the cell targeting group is a protein, a polypeptide or a peptide. In a specific embodiment, the cell targeting group is an antibody or functional fragment thereof. Diazo compounds of formula I are useful to convert carboxylic acid groups of biological molecules, particularly those of the side chains and C-terminus of proteins, polypeptides and peptides into esters, by reaction of the diazo group. In specific embodiments, the esterification cis carried out in buffered aqueous solvent at pH ranging from 5-7 and preferably at pH ranging from 5.5 to 6.5 and does not require the use of a catalyst. In specific embodiments, $R_M$ is an optionally substituted alkyl, alkenyl, alkynyl or aryl group. In specific embodiments, R and $R_M$ together with the nitrogen to which they are bonded form an optionally substituted 5 to 10 member ring system, which optionally contains one or two heteroatoms in addition to the N. In specific embodiments, $R_M$ is an optionally substituted alkyl, alkenyl or alkynyl group having 1, 2, 3, 4, 5 or 6 carbon atoms. In specific embodiments, R is hydrogen, methyl or ethyl. In specific embodiments, R is hydrogen, methyl, or ethyl and $R_M$ is an optionally substituted alkyl, alkenyl or alkynyl group having 1, 2, 3, 4, 5 or 6 carbon atoms. In specific embodiments, R is hydrogen, methyl, or ethyl and $R_M$ is an alkyl, alkenyl or alkynyl group having 1, 2, 3, 4, 5 or 6 carbon atoms. Optional substitution of alkyl, alkenyl, or alkynyl groups includes substitution with non-hydrogen substituents selected from alkyl, alkoxy, halogen, haloalkyl or haloalkoxy.

In a specific embodiment, diazo-compounds are those of formula I where:
R is hydrogen, an optionally substituted alkyl, alkenyl or alkynyl group;
$R_A$ represents hydrogens at each phenyl ring position, or represents 1 to 5 non-hydrogen substituents on the phenyl ring (any remaining ring positions carrying hydrogens), wherein the non-hydrogen substituents are selected from the group consisting of alkyl, cycloalkyl, alkoxy, cycloalkoxy, alkenyl, alkenyloxy, aryl, aryl oxy, arylalkyl, arylalkyl oxy, halogen, haloalkyl, haloalkoxy, heterocyclyl, sulfhydryl (—SH), thioalky (—S-alkyl), —NH$_2$ and —NH—CO—R$_P$, where the alkyl, cycloalkyl, alkoxy, cycloalkoxy, alkenyl, alkenyloxy, aryl, aryloxy, arylalkyl, arylalkyloxy and heterocyclyl groups are optionally substituted with 1-3 non-hydrogen substituents selected from alkyl, alkoxy, halogen, haloalkyl or haloalkoxy groups and $R_P$ is hydrogen, an alkyl group or $R_{M1}$; and
$R_M$ or $R_{M1}$ are independently an optionally substituted organic group M or $M_1$, respectively, having from 1 to 100 carbon atoms and optionally nitrogen, oxygen or sulfur atoms, or -L-M, or -L$_1$-M$_1$, respectively, where -L- and -L$_1$- are independently a divalent linker moiety having from 1-30 carbon atoms and optionally nitrogen, oxygen or sulfur atoms; or
$R_M$ or $R_{M1}$ is or comprises a polymer, such as polyethylene glycol where the polymer is directly bonded into the compound or is bonded via a linker (-L- and -L$_1$-).

In specific embodiments, $R_M$ or $R_{M1}$ is a cargo molecule. In a specific embodiment, both of $R_M$ or $R_{M1}$ are cargo molecules. In specific embodiments, $R_M$ or $R_{M1}$ is or comprises a polymer. In specific embodiments, $R_M$ or $R_{M1}$ is or comprises a hydrophilic polymer. In specific embodiments, $R_M$ or $R_{M1}$ is or comprises a hydrophilic polymer having number average molecular weight of 10,000 or less. In specific embodiments, the polymer. is polyethylene glycol. In specific embodiments, the polyethylene glycol has number average molecular weight less than 10,000.

In specific embodiments, $R_A$ represents 1 to 3 non-hydrogen substituents on the phenyl ring (any remaining ring positions carrying hydrogens). In specific embodiments, $R_A$ represents 1 or 2 non-hydrogen substituents on the phenyl ring (any remaining ring positions carrying hydrogens). In specific embodiments, $R_A$ represents 1 non-hydrogen substituents on the phenyl ring (any remaining ring positions carrying hydrogens).

The invention also provides a method for esterifying one or more carboxylic acid groups in an organic or biological molecule which comprises contacting the organic or biological molecule with a diazo-compound of formula I. Esterification employing diazo-compounds of formula I can, dependent upon $R_M$ and/or $R_{M1}$, facilitate labeling, cell targeting, and/or cell penetration of the species (e.g., a protein) which is esterified. Compounds of formula I where $R_M$ and/or $R_{M1}$ is or comprises a reactive group or a latent reactive group can be employed as bifunctional or trifunctional reagents to bond other $R_M$ and/or $R_{M1}$ groups which are, for example, labels, cell penetrating groups, or cell targeting groups to the diazo-moiety of formula I. More specifically, compounds of formula I where $R_M$ and/or $R_{M1}$ is or comprises a reactive group or a latent reactive group can be employed as heterobifunctional or heterotrifunctional reagents where reactive and latent reactive groups have orthogonal reactivity.

In specific embodiments, the invention provides compounds of formula II

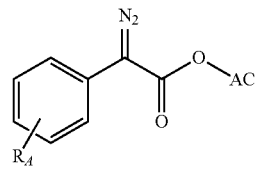

where $R_A$ is defined as for formula I above and wherein AC represents the leaving group of an activated ester. Compounds of formula V are useful at least as reagents in the preparation of the compounds of formula I. Activated esters include among others, N-hydroxysuccinimide esters (NHS esters), N-hydroxysulfosuccinimide esters (sulfo-NHS esters), N-hydroxyphthalimide esters, phenyl esters where the phenyl group is substituted with one or more electron withdrawing groups (e.g., nitro groups or halogens), optionally substituted alkyl or aryl sulfonate esters (e.g., tosyl esters, mesyl esters, or triflate esters). These compounds are useful at least for the preparation of diazo esterification reagents of this invention.

In specific embodiments of formula II, $R_A$ represents substitution of the indicated ring with 1 to 5 non-hydrogen substituents on the phenyl ring (any remaining ring positions carrying hydrogens), wherein the non-hydrogen substituents are selected from the group consisting of alkyl, cycloalkyl, alkoxy, cycloalkoxy, alkenyl, alkenyloxy, aryl, aryl oxy, arylalkyl, arylalkyl oxy, halogen, haloalkyl, haloalkoxy, heterocyclyl, sulfhydryl (—SH), thioalky (—S-alkyl), —NH$_2$ and —NH—CO—R$_P$, where the alkyl, cycloalkyl, alkoxy, cycloalkoxy, alkenyl, alkenyloxy, aryl, aryloxy, arylalkyl, arylalkyloxy and heterocyclyl groups are optionally substituted with 1 to 5 non-hydrogen substituents selected from alkyl, alkoxy, halogen, haloalkyl or haloalkoxy groups and $R_P$ is hydrogen, an alkyl group or $R_{M1}$, where $R_{M1}$ is as defined for formula I. In specific embodiments of formula II, $R_A$ is in the para position on the phenyl ring. In specific embodiments, $R_A$ is p-alkyl. In specific embodiments, $R_A$ is p-methyl. In specific embodiments, $R_A$ is p-alkyloxy. In specific embodiments, $R_A$ is p-methoxy.

In specific embodiments, the invention provides reagents of formula IIA:

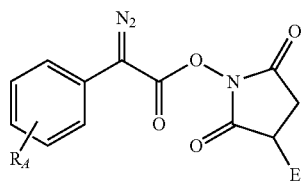

where $R_A$ is as defined for formula I, and E is hydrogen or —SO$_3^-$ (sulfo) salt (e.g., a sodium salt). In specific embodiments of formula IIA, $R_A$ is in the para position on the phenyl ring. In specific embodiments, $R_A$ is p-alkyl. In specific embodiments, $R_A$ is p-methyl. In specific embodiments, $R_A$ is p-alkyloxy. In specific embodiments, $R_A$ is p-methoxy.

Additional aspects and embodiments of the invention will become apparent to one of ordinary skill in the art on review of the following detailed description and non-limiting examples.

BRIEF DESCRIPTION OF THE DRAWINGS

FIG. 1 illustrates, in panel B, the synthetic route to diazo compounds 1-6 where the steps are a) NBS, AIBN; b) NaN$_3$, THF:H$_2$O; c) NHS, DCC, THF; d) PhCH$_2$NH$_2$, DCM; e) N-succinimidyl 3-(diphenylphosphino)propionate, then NaHCO$_3$ or DBU [5a,b], f) imidazole-1-sulfonyl azide hydrochloride, DBU, CuSO$_4$, MeOH [29].

FIG. 2 in panel B illustrates a Hammett plot of the data in panel A. Values of $\sigma_p$ are from Hansch et al. [32]. $\rho = -2.7$.

FIG. 3 also provides a graph showing the effect of $\sigma_p$ value on the chemoselectivity (ester/alcohol product ratio) of diazo compounds 1-6 in 1:1 buffer:acetonitrile at the bottom of the figure.

FIG. 4 also shows structures of acids a-c and provides a Table of product ratios illustrating chemoselectivity of esterification reactions of diazo-compound 2 in aqueous solution at the bottom of the figure.

FIG. 7, panel B is a graph showing the number of labels added to GFP for each diazo compound as determined with MALDI-TOF mass spectrometry.

DETAILED DESCRIPTION OF THE INVENTION

This invention is based at least in part on studies of the reactivity of certain diazo-compounds for esterification of carboxylic acid groups as a function of their structure and electronic properties. Diazo compounds can function for esterification of carboxylic acids. This reactivity can provide unique opportunities in chemical biology. For example, unlike the alkylation of other functional groups, O-alkylation of a carboxyl group is bioreversible because mammalian cells contain non-specific esterases.[7, 26 a-c] The esterification of carboxyl groups in proteins and other biomolecules is, however, difficult to effect, as solvent water competes effectively with alcohols for eletrophilic acyl groups. In contrast, esterification reactions mediated by diazo groups rely on the carboxyl group serving as a nucleophile (Scheme 1). [27a,b].

Scheme 1

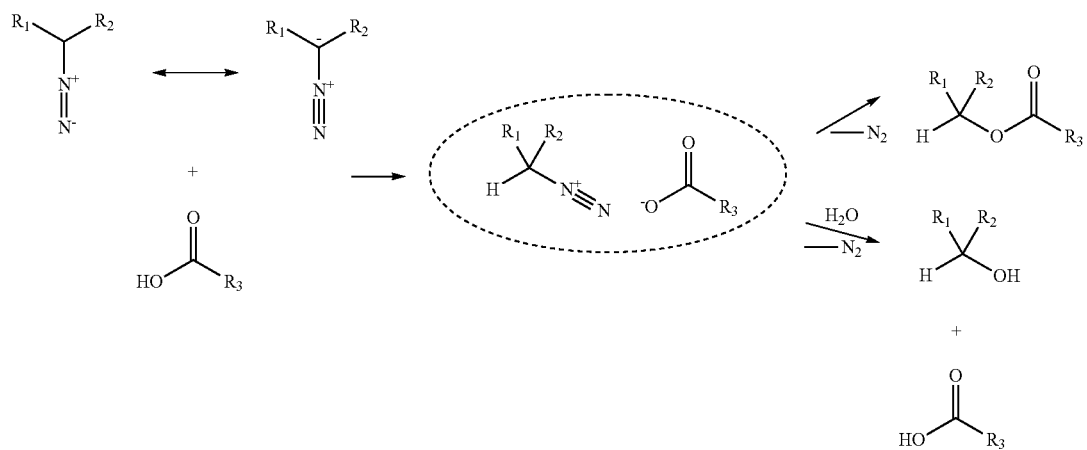

Figure 1:
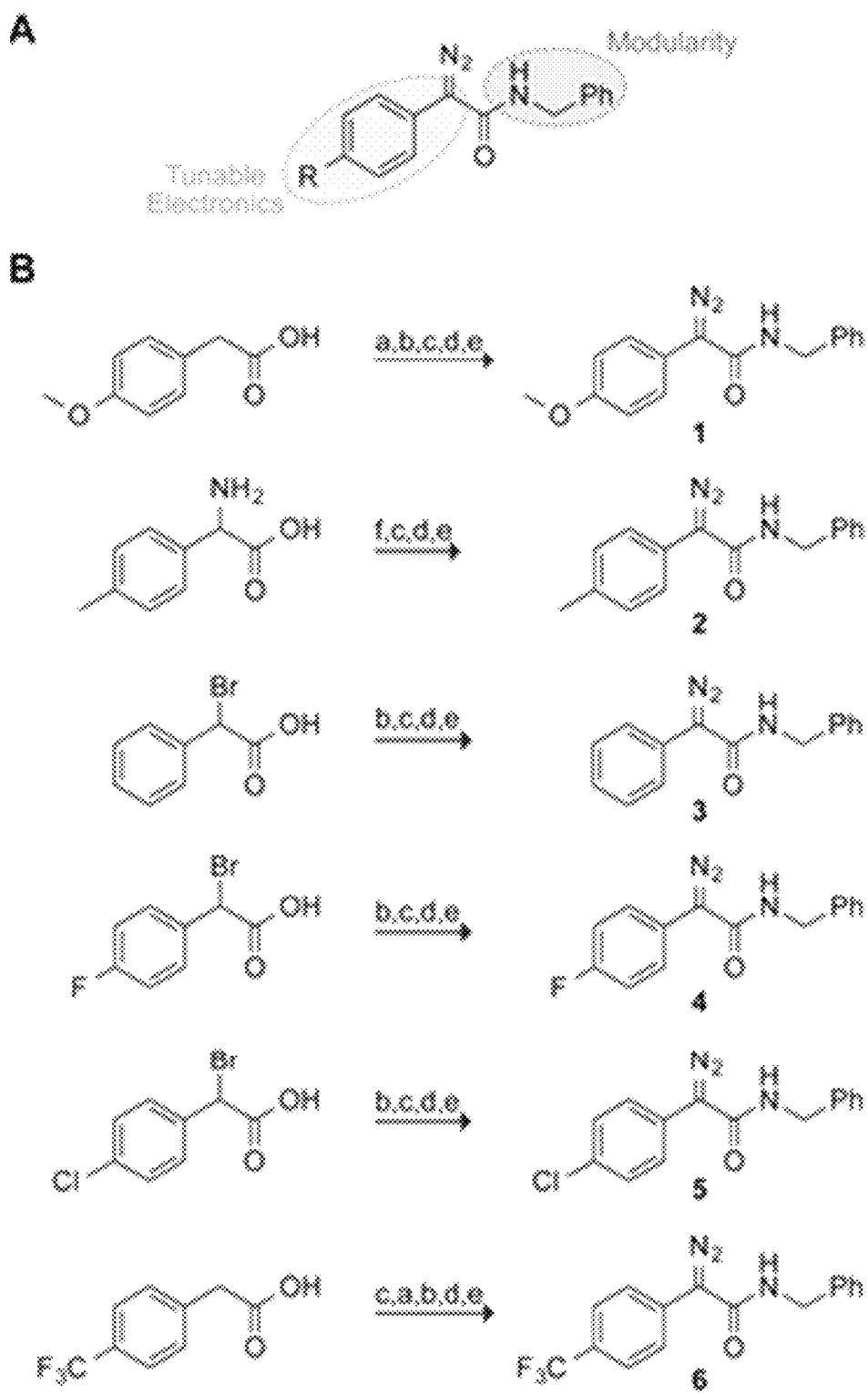
FIG. 1 illustrates, in panel A, a scaffold for testing the reactivity and selectivity of diazo compounds.

Attempts have been made to use diazo compounds to label proteins. [19, 28a-c] A large molar excess (up to 103-fold) of diazo compound was required to overcome hydrolytic decomposition. Moreover, the reaction was not chemoselective, as amino, sulfhydryl, and phenolic side chains suffered alkylation. Such modifications are potentially deleterious to protein function and not bioreversible. [30]. This invention relates to diazo-compounds exhibiting improved esterification of carboxyl groups in an aqueous environment. Derivatives of phenylglycinamide (see FIG. 1, panel A) have been investigated. This scaffold delocalizes the electron density on Cα into an amidic carbonyl group as well as a phenyl group that enables a Hammett analysis [31a-d] of the esterification reaction.

The invention provides methods and reagents for esterification of biological molecules including proteins, polypeptides and peptides. The invention provides certain diazo compounds of formula I:

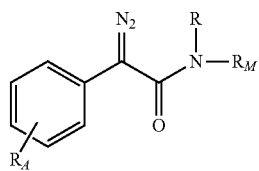

I where $R_A$ represents 1-5 substituents on the indicated phenyl ring, R is hydrogen, an alkyl, alkenyl or alkynyl group, and $R_M$ is generally an organic group, which can includes a label, a cell penetrating group, a cell targeting group, or a reactive group or latent reactive group for reaction to bond to a label, a cell penetrating group, or a cell targeting group, among other organic groups. $R_M$ optionally includes a spacer or linker group. In a specific embodiment, the cell targeting group is a protein, a polypeptide or a peptide. In a specific embodiment, the cell targeting group is an antibody or functional fragment thereof. Diazo compounds of formula I are useful to convert carboxylic acid groups of biological molecules, particularly those of the side chains and C-terminus of proteins, polypeptides and peptides into esters, by reaction of the diazo group. In specific embodiments, the esterification is carried out in buffered aqueous solvent at pH ranging from 5-7 and preferably at pH ranging from 5.5 to 6.5 and does not require the use of a catalyst. In specific embodiments, $R_M$ is an optionally substituted alkyl, alkenyl, alkynyl or aryl group. In specific embodiments, R and $R_M$ together with the nitrogen to which they are bonded form an optionally substituted 5 to 10 member ring system, which optionally contains one or two heteroatoms in addition to the N. In specific embodiments, $R_M$ is an optionally substituted alkyl, alkenyl or alkynyl group having 1, 2, 3, 4, 5 or 6 carbon atoms. In specific embodiments, R is hydrogen, methyl or ethyl. In specific embodiments, R is hydrogen, methyl, or ethyl and $R_M$ is an optionally substituted alkyl, alkenyl or alkynyl group having 1, 2, 3, 4, 5 or 6 carbon atoms. In specific embodiments, R is hydrogen, methyl, or ethyl and $R_M$ is an alkyl, alkenyl or alkynyl group having 1, 2, 3, 4, 5 or 6 carbon atoms. Optional substitution of alkyl, alkenyl, or alkynyl groups includes substitution with non-hydrogen substituents selected from alkyl, alkoxy, halogen, haloalkyl or haloalkoxy.

In a specific embodiment, diazo-compounds useful in the invention are those of formula I where:
R is hydrogen, an optionally substituted alkyl, alkenyl or alkynyl group;
$R_A$ represents hydrogens at each phenyl ring position, or represents 1 to 5 non-hydrogen substituents on the phenyl ring (any remaining ring positions carrying hydrogens), wherein the non-hydrogen substituents are selected from the group consisting of alkyl, cycloalkyl, alkoxy, cycloalkoxy, alkenyl, alkenyloxy, aryl, aryl oxy, arylalkyl, arylalkyl oxy, halogen, haloalkyl, haloalkoxy, heterocyclyl, sulfhydryl (—SH), thioalky (—S-alkyl), —NH$_2$ and —NH—CO—$R_P$, where the alkyl, cycloalkyl, alkoxy, cycloalkoxy, alkenyl, alkenyloxy, aryl, aryloxy, arylalkyl, arylalkyloxy and heterocyclyl groups are optionally substituted with 1-3 non-hydrogen substituents selected from alkyl, alkoxy, halogen, haloalkyl or haloalkoxy groups and $R_P$ is hydrogen, an alkyl group or $R_{M1}$; and
$R_M$ or $R_{M1}$ are independently an optionally substituted non-polymeric organic group M or M$_1$, respectively, having from 1 to 100 carbon atoms and optionally nitrogen, oxygen or sulfur atoms, or -L-M, or -L$_1$-M$_1$, respectively, where -L- and -L$_1$- are independently a divalent linker moiety having from 1-30 carbon atoms and optionally nitrogen, oxygen or sulfur atoms; or $R_M$ or $R_{M1}$ is or comprises a polymer, such as polyethylene glycol where the polymer is directly bonded into the compound or is bonded via a linker (-L- and -$L_1$-).

In specific embodiments, $R_M$ or $R_{M1}$ is a cargo molecule. In a specific embodiment, both of $R_M$ or $R_{M1}$ are cargo molecules. In specific embodiments, $R_M$ or $R_{M1}$ is or comprises a polymer. In specific embodiments, $R_M$ or RM1 is or comprises a hydrophilic polymer. In specific embodiments, $R_M$ or $R_{M1}$ is or comprises a hydrophilic polymer having number average molecular weight of 10,000 or less. In specific embodiments, the polymer. is polyethylene glycol. In specific embodiments, the polyethylene glycol has number average molecular weight less than 10,000.

In specific embodiments, $R_A$ represents 1 to 3 non-hydrogen substituents on the phenyl ring (any remaining ring positions carrying hydrogens). In specific embodiments, $R_A$ represents 1 or 2 non-hydrogen substituents on the phenyl ring (any remaining ring positions carrying hydrogens). In specific embodiments, $R_A$ represents one non-hydrogen substituents on the phenyl ring (any remaining ring positions carrying hydrogens).

In specific embodiments, $R_A$ represents ring substitution having at least one non-hydrogen group as listed above at the para ring position. In specific embodiments, $R_A$ represents ring substitution having at least one non-hydrogen group as listed above at a meta ring position.

The compound of formula I optionally has one or two sites for further functionalization through the $R_P$—CO—NH— group on the phenyl ring (left in the above structure) or through $R_M$ on the phenyl ring (right in the above structure).

In specific embodiments, $R_A$ includes ring substitution with a group which has a Hammett $\sigma_p$ (para-sigma) or $\sigma_m$ (meta-sigma) value of −0.2 to +0.1. In specific embodiments, $R_A$ includes ring substitution with a group which has a Hammett $\sigma_p$ (para-sigma) or $\sigma_m$ (meta-sigma) value of −0.17 to +0.1. In specific embodiments, $R_A$ includes ring substitution with a group which has a Hammett $\sigma_p$ (para-sigma) or $\sigma_m$ (meta-sigma) value of −0.17 to +0.05. In specific embodiments, $R_A$ includes ring substitution with a group which has a Hammett $\sigma_p$ (para-sigma) or $\sigma_m$ (meta-sigma) value of −0.17 to 0.

In specific embodiments, $R_A$ is substitution with a group which has a Hammett $\sigma_p$ (para-sigma) or $\sigma_m$ (meta-sigma) value of −0.2 to +0.1. In specific embodiments, $R_A$ is substitution with a group which has a Hammett $\sigma_p$ (para-sigma) or $\sigma_m$ (meta-sigma) value of −0.17 to +0.1. In specific embodiments, $R_A$ is substitution with a group which has a Hammett $\sigma_p$ (para-sigma) or $\sigma_m$ (meta-sigma) value of −0.17 to +0.05. In specific embodiments, $R_A$ is substitution with a group which has a Hammett $\sigma_p$ (para-sigma) or $\sigma_m$ (meta-sigma) value of −0.17 to 0.

In specific embodiments, $R_A$ is substitution at the para, meta or both ring position with a group which has a Hammett $\sigma_p$ (para-sigma) or $\sigma_m$ (meta-sigma) value of −0.2 to +0.1. In specific embodiments, $R_A$ is substitution at the para, meta or both ring position with a group which has a Hammett $\sigma_p$ (para-sigma) or $\sigma_m$ (meta-sigma) value of −0.17 to +0.1. In specific embodiments, $R_A$ is substitution at the para, meta or both ring position with a group which has a Hammett $\sigma_p$ (para-sigma) or $\sigma_m$ (meta-sigma) value of −0.17 to +0.05. In specific embodiments, $R_A$ is substitution at the para, meta or both ring position with a group which has a Hammett $\sigma_p$ (para-sigma) or $\sigma_m$ (meta-sigma) value of −0.17 to 0.

In specific embodiments, $R_A$ represents substitution with one or more substituents selected from alkyl groups having one to four carbon atoms, an alkenyl group having one double bond and two to four carbon atoms, an unsubstituted phenyl group, a alkylthio group (—S-alkyl) having one to four carbon atoms, an —NHCOR$_N$ group where R$_N$ is H or a methyl group, fluorine, or —NH$_2$. In specific embodiments, $R_A$ represents substitution at the para position on the ring with an alkyl group having 1-4 carbon atoms, an alkenyl group having one double bond and one to four carbon atoms, a fluorine, an alkylthio group, a phenyl group, a —NHCOH group or a —NHCOCH$_3$ group. In specific embodiments, $R_A$ represents substitution at the meta position on the ring with an alkyl group having 1-4 carbon atoms, a phenyl group, or an —NH$_2$ group.

In a specific embodiment $R_A$ is a single group in the para position on the phenyl ring of formula I. In a specific embodiment $R_A$ is a single group in a meta position on the phenyl ring of formula I.

In specific embodiments, $R_A$ is an alkyl group having 1-6 carbon atoms. In more specific embodiments, $R_A$ is methyl or ethyl. In specific embodiments, $R_A$ is a single alkyl group having 1-6 carbon atoms in the para position on the phenyl ring of formula I. In specific embodiments, $R_A$ is a single methyl or ethyl group in the para position on the phenyl ring of formula I. In specific embodiments, $R_A$ is a methyl group in the para position on the phenyl ring of formula I.

In specific embodiments, $R_A$ is a heterocyclyl group bonded to the phenyl ring of formula I via a nitrogen. In specific embodiments, $R_A$ is a heterocyclyl group bonded to the para position of the phenyl ring of formula I via a nitrogen. In specific embodiments, $R_A$ is a single piperazinyl group or a morpholino group bonded to the phenyl ring via the ring N of the group. In specific embodiments, $R_A$ is a single piperazinyl group or a morpholino group bonded to the para position of the phenyl ring via the ring N of the group.

In a specific embodiment, $R_A$ is a $R_P$—CO—NH— group where is $R_P$ is $R_{M1}$ or M1. In specific embodiments, a single $R_P$—CO—NH— group is bonded at the para position of the phenyl ring in formula I.

In embodiments, $R_M$ and $R_{M1}$ are independently an organic group having from 1-20, 1-30, 1-40 or 1-50 carbon atoms and optionally having nitrogen, oxygen or sulfur atoms. In specific embodiments, $R_M$ and/or $R_{M1}$ has 1, 2, 3, 4, or 6 heteroatoms selected from nitrogen, oxygen or sulfur. In embodiments, -L- and/or -$L_1$- is a linker moiety having from 1-6, 1-10 or 1-20 carbon atoms and optionally nitrogen, oxygen or sulfur atoms. In embodiments, -L- and/or -$L_1$- has 1-4, oxygen atoms (—O—). In embodiments, -L- and/or -$L_1$- has 1-4 —CO— moieties. In embodiments, -L- and/or -$L_1$- has 1-4 —N—R$_N$— moieties, where —R$_N$ is hydrogen or an alkyl group having 1-3 carbon atoms. In embodiments, -L- and/or -$L_1$- has 1-4 —S— moieties. In embodiments, -L- and/or -$L_1$- has one —S—S— moiety. In embodiments, -L- and/or -$L_1$- has 1 or 2 —CO—, —NR$_N$— or —NR$_N$—CO— moieties. In embodiments, -L- and/or -$L_1$- has 1 or 2 —CO—O— or —O—CO-moieties.

In specific embodiments, -L- and/or -$L_1$- are or comprise an alkenylene moiety —(CH$_2$)q-, where q is an integer from 1 to 6, 1-12 or 1-20. In specific embodiments, -L- and/or -$L_1$- are or comprise an alkoxyalkyl or ether group, e.g., —[O]a-[(CH$_2$)b-O-]r-(CH$_2$)c-, where a is 0 or 1, b and c are independently an integer from 0 to 6 (where one of b or c is not 0), and r is 0 or is an integer from 1-3, 1-6 or 1-10. In specific embodiments, -L- and/or -$L_1$- are or comprise an alkoxyalkyl or ether group, e.g., —[N—R$_N$]d-[(CH$_2$)b-O-]r-(CH$_2$)c-, where d is 1, b and c are independently an integer from 0 to 6 (where one of b or c is not 0), and r is 0 or is an integer from 1-3, 1-6 or 1-10. In specific embodiments, $R_N$ is hydrogen, b is 2 or 3, r is 1-3 or 1-6 and c is 0 or 1. In specific embodiments, -L- and/or -$L_1$- are or comprise amino moieties, e.g., —[$NR_N$]a-[($CH_2$)b-$NR_N$-]r-($CH_2$)c-, where a is 0 or 1, b and c are independently an integer from 0 to 6 (where one of b or c is not 0), and r is 0 or is an integer from 1-3, 1-6 or 1-10. In specific embodiments, each $R_N$ is hydrogen, b is 2 or 3, r is 1-3 or 1-6 and c is 0, 2 or 3. In specific embodiments, -L- and/or -$L_1$- comprise one or two X moieties at either end of the moiety which function for linkage of the spacer, where X is selected from —CO—, —OCO—, —CO—$NR_N$—, or —$R_N$—CO—.

In an embodiment, $R_M$ is an alkyl, cycloalkyl, aryl, arylalkyl, heterocyclyl or heteroaryl group which is optionally substituted with one or more alkyl, alkoxy, aryl, alkylaryl, halogen, haloalkyl, or haloalkoxy groups. In an embodiment, $R_M$ is an alkyl, cycloalkyl, aryl, arylalkyl, heterocyclyl or heteroaryl group which is optionally substituted with one or more alkyl, alkoxy, aryl, alkylaryl, halogen, haloalkyl, or haloalkoxy groups.

In an embodiment, $R_P$ is an alkyl, cycloalkyl, aryl, arylalkyl, heterocyclyl or heteroaryl group which is optionally substituted with one or more alkyl, alkoxy, aryl, alkylaryl, halogen, haloalkyl, or haloalkoxy groups. In an embodiment, $R_P$ is an alkyl, cycloalkyl, aryl, arylalkyl, heterocyclyl or heteroaryl group which is optionally substituted with one or more alkyl, alkoxy, aryl, alkylaryl, halogen, haloalkyl, or haloalkoxy groups.

In an embodiment, $R_M$ or $R_{M1}$ comprise or are independently a label or reporter molecule (e.g., a fluorescent label, an isotopic label, an imaging agent, a quantum dot, and the like). In an embodiment, the label or reporter is indirectly bonded to the diazo-compound of formula I via -L- or -$L_1$-. In a specific embodiment, only one of $R_M$ or $R_{M1}$ is or comprises a label or reporter.

In a specific embodiment, $R_M$ or $R_{M1}$ is or comprises biotin or a derivative thereof. In a specific embodiment, biotin or a derivative thereof is directed bonded in the compound of formula I or is indirectly bonded therein via a linker.

In an embodiment, $R_M$ or $R_{M1}$ comprises or is a cell penetrating group, such as a cationic domain, including peptidic cationic species (e.g., HIV-TAT, penetratin, and polyarginine (e.g., nona-arginine) and more generally cell penetrating peptides (CPP), which are also called protein transduction domains (PTDs) or non-peptidic cationic species (e.g., PAMAM dendrimers and polyethylenimine), guanidinium, positively charged amines, hydrophobic groups such as fluorenyl or pyrene, which are optionally bonded via an -alkylene-$CO_2$— (e.g., pyrenebutyrate), optionally substituted fluorenyl groups or optionally substituted phenylboronates. In an embodiment, the cell penetrating group is indirectly bonded to the diazo-compound of formula I via -L- or -$L_1$-. In a specific embodiment, only one of $R_M$ or $R_{M1}$ is or comprises a cell penetrating group.

In an embodiment, $R_M$ or $R_{M1}$ comprises or is a cell targeting group, such as a ligand for a cell-surface receptor (e.g., a steroid, folic acid, substance P, and the RGD tripeptide) or other targeting species such as nuclear localization peptides. The targeting groups can be a protein, polypeptide or peptide. The targeting groups may be an antibody or functional fragment thereof. In an embodiment, the cell targeting group is indirectly bonded to the diazo compound of formula I via -L- or -$L_1$-. In a specific embodiment, only one of $R_M$ or $R_{M1}$ is or comprises a cell targeting group.

Exemplary cell targeting groups are described in Srinivasarco et al.[38]. This reference is incorporated by reference herein for descriptions of ligands for cell targeting. In a specific embodiment, the ligand employed for cell targeting should exhibit an affinity for its receptor of dissociation constant of 10 nM or lower. In a specific embodiment, more than one cell targeting group may be employed in a given compound of formula I.

In an embodiment, $R_M$ or $R_{M1}$ comprises or is a reactive group, such as a group that reacts with an amine or a thiol. In a specific embodiment, $R_M$ is or comprises an amine reactive group, such as an N-hydroxy-succinimide ester group an N-hydroxysulfosuccinimide ester group. In a specific embodiment, $R_M$ is or comprises an amine reactive group, such as an N-hydroxyphthalimide ester group. In another specific embodiment, $R_M$ is an amine reactive activated ester such as a p-nitrophenyl ester group or a pentafluorophenyl ester group. In another specific embodiment, $R_M$ is a thiol reactive group, such as a 2-pyridyldithio group or an iodoacetyl group. In an embodiment, the functional group is bonded indirectly to the diazo-compound of formula I via -L- or -$L_1$-. In a specific embodiment, one of $R_M$ or $R_{M1}$ is or comprises a reactive group, such as an amine reactive group. In a specific embodiment, both of $R_M$ and $R_{M1}$ are or comprise a reactive group, particularly where the reactivity of the two reactive groups is orthogonal, such as where one is an amine reactive group and the other is a thiol reactive group.

In an embodiment, $R_M$ or $R_{M1}$ comprises or is a latent reactive group which is capable of being activated for reaction with an amine, thiol, alcohol or carboxylate. In an embodiment, $R_M$ or $R_{M1}$ comprises or is a latent reactive group carrying a protective group which is selectively removable to activate the latent reactive group for reaction. In an embodiment, the latent reactive group is bonded indirectly to the diazo-compound of formula I via -L- or -$L_1$-. In a specific embodiment, one of $R_M$ or $R_{M1}$ is or comprises a latent reactive group. In a specific embodiment, both of $R_M$ and $R_{M1}$ are or comprise a latent reactive group. In a specific embodiment, one of $R_M$ or $R_{M1}$ is or comprises a reactive group, such as an amine reactive group and the other is a latent reactive group, such as a protected amine reactive group. In a specific embodiment, both of $R_M$ and $R_{M1}$ are or comprise a reactive group or latent reactive, particularly where the reactivity of the two reactive groups is orthogonal, such as where one is an amine reactive group and the other is a protected thiol reactive group.

In an embodiment, where the diazo-compound of formula I comprises a reactive group and/or a latent reactive group, the invention provides bifunctional or trifunctional and particularly heterobifunctional or heterotrifunctional reagents for bonding the diazo-moiety of the compound of formula to various $R_M$ or $R_{M1}$ groups. In an embodiment, the reactive group or latent reactive group has reactivity that is orthogonal to the diazo-group of the diazo-compound of formula I. In specific embodiments, the diazo-compound comprises an amine reactive group. In specific embodiments, the diazo-compound comprises a latent amine reactive group. In specific embodiments, the diazo-compound comprises an amine reactive group other than the diazo group and a latent amine reactive group. In specific embodiments, the diazo-compound comprises a thiol reactive group. In specific embodiments, the diazo-compound comprises an amine reactive group other than a diazo group and a thiol reactive group, either of which is a latent reactive group. In specific embodiments, the diazo-compound comprises an $R_M$ or $R_{M1}$ group that is a carboxylate reactive group or a latent carboxylate reactive group (i.e., a protected carboxylate reactive group).

The invention also provides compounds of formula II:

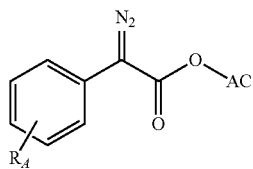

where $R_A$ is defined as for formula I above and wherein AC represents the leaving group of an activated ester. Compounds of formula II are useful at least as reagents in the preparation of the compounds of formula I. Activated esters include among others, N-hydroxysuccinimide esters (NHS esters), N-hydroxysulfosuccinimide esters (sulfo-NHS esters), N-hydroxyphthalimide esters, phenyl esters where the phenyl group is substituted with one or more electron withdrawing groups, optionally substituted alkyl or aryl sulfonate esters (e.g., tosyl esters, mesyl esters, or triflate esters).

Electron withdrawing groups include halogens and nitro groups, for example. Specific activated esters are fluorinated, chlorinated or brominated phenyl esters or nitro-substituted phenyl esters. More specifically, p-F phenyl, meta, meta-difluorophenyl, meta, meta, para-trifluorophenyl, pentafluorophenyl, p-nitro phenyl, p-chlorophenyl, and p-bromophenyl activated esters can be employed.

In specific embodiments of formula II, $R_A$ represents substitution of the indicated ring with one to five non-hydrogen substituents on the phenyl ring (any remaining ring positions carrying hydrogens), wherein the non-hydrogen substituents are selected from the group consisting of alkyl, cycloalkyl, alkoxy, cycloalkoxy, alkenyl, alkenyloxy, aryl, aryl oxy, arylalkyl, arylalkyl oxy, halogen, haloalkyl, haloalkoxy, heterocyclyl, sulfhydryl (—SH), thioalky (—S-alkyl), —NH$_2$ and —NH—CO—R$_P$, where the alkyl, cycloalkyl, alkoxy, cycloalkoxy, alkenyl, alkenyloxy, aryl, aryloxy, arylalkyl, arylalkyloxy and heterocyclyl groups are optionally substituted with 1-5 non-hydrogen substituents selected from alkyl, alkoxy, halogen, haloalkyl or haloalkoxy groups and R$_P$ is hydrogen, an alkyl group or R$_{M1}$, where R$_{M1}$ is as defined for formula I. In specific embodiments of formula II, $R_A$ is in the para position on the phenyl ring. In specific embodiments of formula II, $R_A$ is p-alkyl. In specific embodiments of formula II, $R_A$ is p-methyl. In specific embodiments of formula II, $R_A$ is p-alkyloxy. In specific embodiments of formula II, $R_A$ is p-methoxy.

In specific embodiments of formula II, the invention provides reagents of formula IIA:

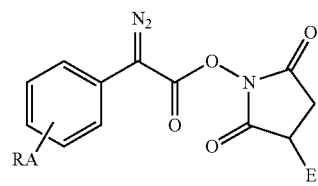

where $R_A$ is as defined for formula I, and E is hydrogen or —SO$_3$— (sulfo) salt (e.g., a sodium salt). In specific embodiments of formula IIA, $R_A$ is in the para position on the phenyl ring. In specific embodiments of formula IIA, $R_A$ is p-alkyl. In specific embodiments of formula IIA, $R_A$ is p-methyl. In specific embodiments of formula IIA, $R_A$ is p-alkyloxy. In specific embodiments of formula IIA, $R_A$ is p-methoxy. In related specific embodiments of compounds of formula IIA the NHS ester group can be replaced with an N-hydroxyphthalimide ester group.

Compounds of formula II and more specifically of formula IIA are at least useful in the preparation of compounds of formula I. As illustrated in the examples, the compounds of formula II and IIA can be reacted with amines to generate compounds of formula I.

The invention provides a method for esterifying one or more carboxylic acid groups in an organic or biological molecule which comprises contacting the organic or biological molecule with a diazo compound of formula I. In a specific embodiment, the reaction is carried out in an aqueous solution. In a specific embodiment, the reaction is carried out in a water/organic solvent mixture. In specific embodiments, the organic solvent is acetonitrile, methanol, ethanol, t-butanol, dimethylsulfoxide, THF, or related ethers. In specific embodiments, the organic solvent is acetonitrile. In specific embodiments, the reaction is carried out in solvent containing up to 70% of buffer with organic solvent. In specific embodiments, the reaction is carried out in solvent containing from 10-70% (by volume) of water or buffer with organic solvent. In specific embodiments, the reaction is carried out in solvent containing from 0.1-10% organic solvent in water or buffer. In specific embodiments, the reaction is carried out in an organic solvent selected from acetonitrile, methanol, ethanol, t-butanol, dimethylsulfoxide, THF or related ethers. The composition of the solvent is dependent upon the solubility of the diazo-compound in water. In a specific embodiment, dependent upon the solubility of the diazo-compound, the reaction is carried out in buffered aqueous solution. In a specific embodiment, the reaction is carried out at a pH ranging from 5 to 7 and more preferably 5.5 to 6.5. In a specific embodiment, the reaction is carried out at a temperature ranging from about room temperature to about 40° C. In a specific embodiment, the reaction is carried out at ambient temperature. In a specific embodiment, the reaction is carried out at a temperature ranging from 30-37° C. In a specific embodiment, the reaction is carried out at a temperature ranging from 25-30° C.

Esterification employing diazo compounds of formula I can, dependent upon R$_M$ and/or R$_{M1}$, facilitate labeling, cell targeting, and/or cell penetration of the species (e.g., protein) which is esterified. Compounds of formula I where R$_M$ and/or R$_{M1}$ is or comprises a reactive group or a latent reactive group can be employed as bifunctional or trifunctional reagents to bond other R$_M$ and/or R$_{M1}$ groups which are, for example, labels, cell penetrating groups, or cell targeting groups to the diazo-moiety of formula I. More specifically, compounds of formula I where R$_M$ and/or R$_{M1}$ is or comprises a reactive group or a latent reactive group can be employed as heterobifunctional or heterotrifunctional reagents where reactive and latent reactive groups have orthogonal reactivity.

Thus, the invention further provides a method for labeling a molecule (having one or more carboxylate groups, particularly a biological molecule) by covalently bonding a label to the molecule by esterifying the carboxylate group(s) of the molecule with a diazo-compound of formula I wherein R$_M$ and/or R$_{M1}$ is or comprises a label, particularly a fluorescent label, an isotopic label, a radiolabel, an imaging agent, or a quantum dot.

Thus, the invention further provides a method for enhancing cellular uptake of a cargo molecule (having one or more carboxylate groups) by covalently bonding cell penetrating groups to the cargo molecules by esterifying the cargo molecule with a diazo-compound of formula I wherein $R_M$ is or comprises a cell penetrating group, particularly a guanidinium, positively charged amine, hydrophobic groups such as fluorenyl or pyrene, which are optionally bonded via an -alkylene-$CO_2$— (e.g., pyrenebutyrate), optionally substituted fluorenyl group or optionally substituted phenylboronate.

Thus, the invention further provides a method for targeting of a cargo molecule (having one or more carboxylate groups) by covalently bonding a cell targeting group to the cargo molecule by esterifying the cargo molecule with a diazo-compound of formula I wherein $R_M$ and/or $R_{M1}$ is or comprises a cell targeting group, particularly a ligand for a cell-surface receptor (e.g., a steroid, folic acid, substance P, or the RGD tripeptide) or other targeting species such as nuclear localization peptides.

In a related aspect, the compound of formula I is employed to esterify a targeting group and one or more cargo molecules are otherwise bonded into the compound of formula I, for example $R_M$ or $R_{M1}$ is or comprises a cargo molecule or both $R_M$ and $R_{M1}$ are or comprise a cargo molecule. In this embodiment, the cargo molecule is, for example, a protein, polypeptide or peptide other than the targeting group or is a cargo molecule other than a protein, polypeptide or peptide. For example, in this embodiment the one or more cargo molecules can be one or more nucleic acids.

The term cargo molecule is used generally herein to refer to any molecule that it is desired to target to a cell or to introduce into a cell. In specific embodiments, cargo molecules are proteins carrying one or more carboxylate groups. In specific embodiments, cargo molecules are nucleic acids carrying one or more carboxylate groups.

Dependent upon the $R_M$ and $R_{M1}$ groups of the compound of formula I, esterification with the compound of formula I provides for a combination of labeling, enhancing cell penetration or targeting of the species esterified. Thus, the invention provides a method for labeling and adding a cell penetrating group to a selected cargo molecule. Additionally, the invention provides a method for labeling and adding a targeting group to a selected cargo molecule. Additionally, the invention provides a method for adding a targeting group and a cell penetration group to a selected cargo molecule. Additionally, the invention provides a method for adding a label, a targeting group and a cell penetration group to a selected cargo molecule. These methods are achieved by esterification of the cargo molecule with a compound of formula I herein where $R_M$ and $R_{M1}$ are selected to achieve the desired introduction of label, targeting group or cell penetration group. Thus, the invention provides methods for labeling combined with enhancement of cell penetration, for labeling combined with cell targeting, for combined cell targeting and enhanced cell penetration, or for combined labeling, enhanced cell penetration and cell targeting.

When $R_M$ or $R_{M1}$ is a polymer, such as polyethylene glycol, the invention provides a method of functionalizing a cargo molecule, such as a protein, with the polymer by esterification employing a compound of formula I. When $R_M$ or $R_{M1}$ is polyethylene glycol, the invention provides a method of pegylating a cargo molecule, such as a protein, by esterification employing a compound of formula I.

When $R_M$ or $R_{M1}$ is biotin or a derivative thereof, the invention provides a method for biotinylation of a cargo molecule, such as a protein, by esterification employing a compound of formula I. When the biotin derivative is a labelled biotin, the invention provides a method for biotinylation and labelling of the cargo molecule, particularly a protein, polypeptide or peptide.

The invention also relates in part to methods for enhancing cellular uptake of a cargo molecule by esterifying the cargo molecule with a diazo compound of formula I, wherein $R_M$ is a cell penetrating group. A number of such cell penetrating groups are known in the art, which particularly include certain peptides. In a specific embodiment, cellular uptake includes at least partial uptake into the cytosol. Cellular uptake may be in vivo or in vitro. The method of the invention is generally useful for the delivery of any desired molecule carrying one or more carboxylate groups into a cell and specifically includes nucleic acids and analogs thereof; nucleotides and analogs thereof; peptides and proteins; drugs (e.g., anticancer drugs, alkylating agents, antimetabolite, cytotoxic agents; antibiotics, and the like); reporter molecules or labels (e.g., fluorescent labels, isotopic labels, imaging agents, quantum dots, and the like). In a specific embodiment, the cargo comprises a quantum dot carrying amine functionality. The cargo molecule can include combinations of the species listed above, wherein the species are bonded to each other, particularly where the species are covalently bonded to each other. For example, a cargo molecule may combine a peptide, such as a CPP or a nuclear localizing signal with a nucleic acid, or combine a fluorescent, isotopic or other label with a nucleic acid and or peptide. In a specific embodiment, the cargo molecule is or comprises a molecule which affects, regulates or modulates gene expression in the cell, including a molecule which inhibits or decreases gene expression or a molecule which initiates or enhances gene expression. In a specific embodiment, the cargo molecule is a peptide or a protein, for example, an enzyme. In specific embodiments for enhancement of cargo molecule uptake, $R_M$ is guanidinium, an optionally substituted fluorenyl group or an optionally substituted phenylboronate. Diazo compounds of the invention are most generally compounds of formula I with variables as defined above.

Additional exemplary compounds of formula I are described in more detail below. It is noted that compounds of formula II and IIA can be employed to synthesize these additional compounds. In specific embodiments, the compound of formula I can have formula IA:

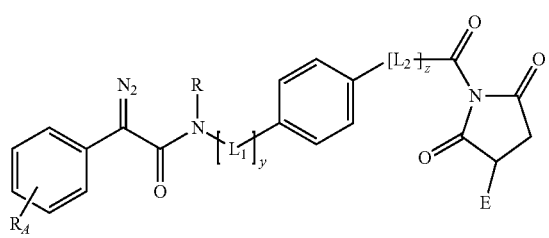

IA where R and $R_A$ are defined for formula I, y and z are 0 or 1, -$L_1$- and -$L_2$- are divalent linkers having linker structures as defined herein and E is hydrogen or —$SO_3$— (sulfo) salt (e.g., a sodium salt). Linkers -$L_1$ and $L_2$- can in an embodiment comprise 1-20, 1-12, 1-6 or 1-3 carbon atoms and optionally one or more oxygen atoms. In specific embodiments of formula IA, -$L_1$- is present and is —$CH_2$— and -L$_2$- is absent. In specific embodiments of formula IA, R$_A$ is in the para position on the phenyl ring. In specific embodiments of formula IA, R$_A$ is p-alkyl. In specific embodiments of formula IA, R$_A$ is p-methyl. In specific embodiments of formula IA, R$_A$ is p-alkyloxy. In specific embodiments of formula IA, R$_A$ is p-methoxy.

In more specific embodiments, compounds of the invention have formula IB:

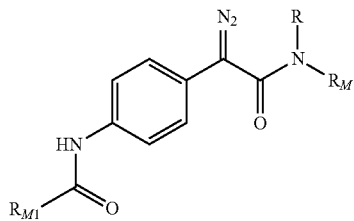

where variables are as defined above for formula I. In specific embodiments of formula IB, R is hydrogen or methyl. In specific embodiments of formula IB, R$_M$ is alkyl having 1-6 carbon atoms. In specific embodiments of formula IB, R$_M$ is an alkynyl having 3 or 4 carbon atoms.

In an embodiment of formula I, R$_M$ or R$_{M1}$ is or comprises the guanidinium group of formula III:

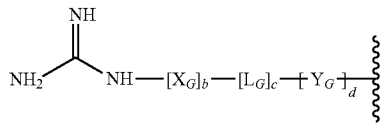

or salts thereof,
where X$_G$ and Y$_G$, independently, are optional bonding moieties (b and d independently are 0 or 1) selected from —NR$_N$—, —O—, —S—, —S—S—, —CO—NR$_N$—, —CO—O—, —NR$_N$—CO—, —O—CO—, —CO—, —CO—S—, or —S—CO—; and
L$_G$ is an optional spacer group (c is 0 or 1) having 1 to 10 carbon atoms and optionally 1-5 oxygen or nitrogen atoms. The guanidinium group can be protonated and be in the form of a salt with an appropriate anion. In a specific embodiment of formula III, b is 1 and X$_G$ is O. In a specific embodiment of formula III, c is 1 and L$_G$ is —(CH$_2$)$_G$—, where G is and integer ranging from 1-12, 1-6 or 1-3 and more specifically G is 2. In a specific embodiment of formula III, d is 1 and Y$_G$ is NH. In a specific embodiment of formula III, b is 1 and X$_G$ is 0, c is 1 and L$_G$ is —(CH$_2$)$_G$—, where G is 2 or 3 and more specifically where G is 2. In a specific embodiment of formula III, b is 1, c is 1 and d is 1, X$_G$ is O, Y$_G$ is NH and L$_G$ is —(CH$_2$)$_G$—, where G is 2 or 3 and more specifically where G is 2. In specific embodiments of compounds of formula I, wherein R$_{M1}$ is or comprises the guanidinium group of formula III, R is hydrogen or methyl and R$_M$ is an alkyl group having 1-6 carbon atoms or R$_M$ is a alkynyl group having 3-4 carbon atoms. In specific embodiments of compounds of formula I, wherein R$_M$ is or comprises the guanidinium group of formula III, R is hydrogen or methyl and R$_A$ is an alkyl group having 1-6 carbon atoms, and more specifically is a methyl group, substituted at the para position of the phenyl ring.

In a specific embodiment, the reagent of formula I, having R$_M$ or R$_{M1}$ that is or comprises the guanidinium of formula III, can be prepared, employing the amine of formula IV:

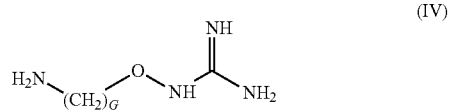

where G is 1-12, 1-6, or 1-3 and more specifically where G is 2.

In a specific embodiment of formula I, R$_M$ or R$_{M1}$ is or comprises the fluorenyl group of formula V:

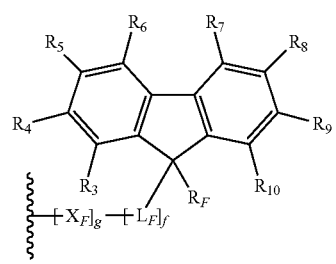

and salts thereof, wherein:
X$_F$ is an optional bonding moiety (g is 0 or 1) selected from —NR$_N$—, —O—, —S—, —S—S—, —CO—NR$_N$—, —CO—O—, —NR$_N$—CO—, —O—CO—, —CO—, —CO—S—, or —S—CO—;
L$_F$ is an optional spacer group (f is 0 or 1) having 1 to 10 carbon atoms and optionally 1-5 oxygen or nitrogen atoms;
R$_F$ is hydrogen or an alkyl group; and
R$_3$-R$_{10}$ are selected from hydrogen, alkyl, alkoxy, alkenyl, alkenoxy, alkynyl, alkynoxy, aryl, aryl oxy, alkylaryl, alkylaryloxy, arylalkyl, arylalkyloxy, heteroaryl, heteroaryloxy, carbocyclic, carbocyclyloxy, heterocyclic or heterocyclyloxy groups each of which is optionally substituted; or
R$_3$-R$_{10}$ are selected from non-hydrogen substituents, including halogens (e.g., Br—, I—, Cl—, F—), hydroxyl (—OH), nitro groups (—NO$_2$), cyano (—CN), isocyano (—NC), thiocyano (—SCN), isothiocyano (—NCS), sulfuryl (—SO$_2$), —N(R')$_2$, —COR', —COOR', —CON(R')$_2$, —NR'—CO—R', —NR'—CO—N(R')$_2$—, —CO—SR', —SO$_2$—NR'$_2$, —OR', or —SR', where each R', independently, is selected from hydrogen, alkyl, alkenyl, alkynyl, aryl, heteroaryl, heterocyclic groups, each of which groups is optionally substituted particularly with one or more halogen, hydroxyl, amino, alkylamino, or dialkylamino groups; or two of R$_3$-R$_{10}$ are linked together to form an optionally substituted carbocyclic, aryl, heterocyclic or heteroaryl ring wherein one or two carbons of the ring can be replaced with —CO— and the carbocyclic or heterocyclic rings can be saturated or unsaturated.

In a specific embodiment, all of R$_3$-R$_{10}$ are hydrogens. In a specific embodiment, all except one of R$_3$-R$_{10}$ are hydrogens. In a specific embodiment, one or more of R$_3$-R$_{10}$ are selected from hydrogen, alkyl groups having 1-3 carbon atoms, halogens, —N(R')$_2$, —COR', —COOR', —CON(R')$_2$, —NR'—CO—R', —NR'—CO—N(R')$_2$—, —CO—SR', —SO$_2$—NR'$_2$, —OR', or —SR', where each R', independently, is selected from hydrogen, alkyl, alkenyl, alkynyl, aryl, heteroaryl, heterocyclic groups, each of which groups is optionally substituted particularly with one or more halogen, hydroxyl, amino, alkylamino, or dialkylamino groups. In a specific embodiment, one or more of R$_3$-R$_{10}$ is a —NR'—CO—R' group.

In specific embodiments of the $R_M$ or $R_{M1}$ group of formula V, $R_3$-$R_{10}$ are independently selected from hydrogen, halogen, or alkyl groups having 1-3 carbon atoms. In specific embodiments, $R_3$-$R_{10}$ are independently selected from hydrogen, chlorine, bromine, iodine, fluorine or alkyl groups having 1-3 carbon atoms. In specific embodiments, $R_3$-$R_{10}$ are independently selected from hydrogen, halogen, or methyl groups. In specific embodiments, one or two of $R_3$-$R_{10}$ are independently selected from non-hydrogen substituents and the remaining R groups are hydrogens. In specific embodiments, one or two of $R_3$-$R_{10}$ are selected from halogen, or alkyl groups having 1-3 carbon atoms and the remaining R groups are hydrogen. In specific embodiments, one or two of $R_3$-$R_{10}$ are selected from halogen, or methyl groups and the remaining R groups are hydrogen.

In a specific embodiment of the $R_M$ or $R_{M1}$ group of formula V, one or both of $R_4$ and $R_9$ are —NR'—CO—R' groups. In specific embodiments, the —NR'—CO—R' groups are —NH—CO—R' groups where R' is an alkyl group or a haloalkyl group, and more specifically where R' is a methyl group or a trifluoroethyl group. In specific embodiments, none of $R_3$-$R_{10}$ are —NR'—CO—R' groups. In specific embodiments, none of $R_3$-$R_{10}$ are amine or amide groups. In specific embodiments, none of $R_3$-$R_{10}$ are isocyanate groups. In specific embodiments, the fluorenyl group can itself exhibit fluorescence.

In specific embodiments of compounds of formula I, wherein $R_{M1}$ is or comprises the fluorenyl group of formula V, R is hydrogen or methyl and $R_M$ is an alkyl group having 1-6 carbon atoms or $R_M$ is a alkynyl group having 3-4 carbon atoms. In specific embodiments of compounds of formula I, wherein $R_M$ is or comprises the fluorenyl group of formula V, R is hydrogen or methyl and $R_A$ is an alkyl group having 1-6 carbon atoms, and more specifically is a methyl group, substituted at the para position of the phenyl ring.

US published application 2016/0067342 (published Mar. 10, 2016) describes derivatization of cargo molecules with fluorenyl groups for enhancing cellular update of a cargo molecule. This application is incorporated by reference herein in its entirety for descriptions of methods of cellular uptake and descriptions of fluorenyl groups for use in the present invention.

In specific embodiments, $R_M$ or $R_{M1}$ is a phenylboronic acids such as those of formulas VIA or VIB:

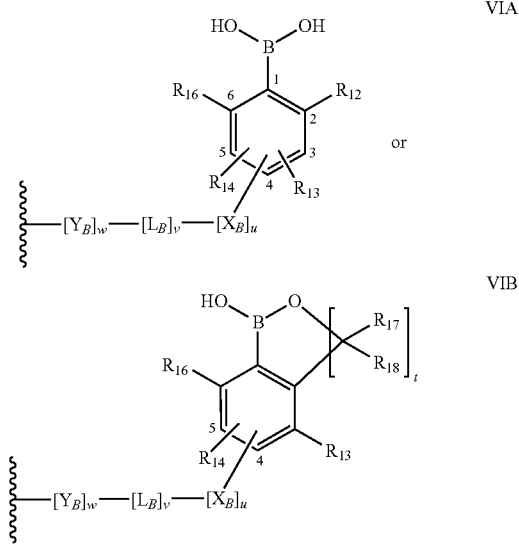

(noting that VIB is a benzoboroxole structure) or salts thereof, where these $R_M$ of $R_{M1}$ groups are attached to the compound of formula I or formula IA through ring positions 3, 4 or 5 or for formula VIB through ring positions 4 or 5;

t is 1 or 2, $X_B$ and $Y_B$ are optional bonding moieties (u and w are independently 0 or 1) selected from —NR$_N$—, —O—, —S—, —S—S—, —CO—NR$_N$—, —CO—O—, —NR$_N$—CO—, —CO—, —CO—, —CO—S—, or —S—CO—;

$L_B$ is an optional spacer group (v is 0 or 1) having 1 to 10 carbon atoms and optionally 1-5 oxygen or nitrogen atoms;

$R_{12}$-$R_{14}$, and $R_{16}$ are independently selected from hydrogen, a straight-chain or branched aliphatic group having 1-8 carbon atoms, an alicyclic group, an aryl group, a heterocyclic group, a heteroaryl group, a —CO$_2$R$_{20}$ group, a —O—CO—R$_{20}$ group, a —CON(R$_{21}$)$_2$ group, a —O—CON(R$_{21}$)$_2$ group; a —N(R$_{21}$)$_2$ group, a —OR$_{20}$ group, a —(CH$_2$)m-OH group, a —(CH$_2$)m-N(R$_{21}$)$_2$ group, a halogen, a nitro group, a cyano group, a —SO$_2$—OR$_{20}$ group, or two adjacent $R_{12}$-$R_{14}$, and $R_{16}$, together with the ring carbons to which they are attached, optionally form a 5-8-member alicyclic, heterocyclic, aryl or heteroaryl ring moiety, each of which groups or moieties is optionally substituted;

each $R_{17}$ and $R_{18}$ is independently selected from hydrogen or a C1-C3 optionally substituted alkyl group;

wherein:

each $R_{20}$ is independently selected from hydrogen, a straight-chain or branched aliphatic group having 1-8 carbon atoms, an alicyclic group, an aryl group, a heterocyclic group, or a heteroaryl group, each of which groups is optionally substituted;

each $R_{21}$ is independently selected from hydrogen, a straight-chain or branched aliphatic group having 1-8 carbon atoms, an alicyclic group, an aryl group, a heterocyclic group, a heteroaryl group, or where two $R_{21}$ together with the nitrogen to which they are attached can form a 5-8 member heterocyclic or heteroaryl ring moiety, each of which groups or moieties is optionally substituted;

m is an integer from 1-8;

wherein optional substitution is substitution by one or more non-hydrogen substituents selected from halogen; an oxo group (=O), a nitro group; a cyano group; a C1-C6 alkyl group; a C1-C6 alkoxy group; a C2-C6 alkenyl group; a C2-C6 alkynyl group; a 3-7 member alicyclic ring, wherein one or two ring carbons are optionally replaced with —CO— and which may contain one or two double bonds; an aryl group having 6-14 carbon ring atoms; a phenyl group; a benzyl group; a 5- or 6-member ring heterocyclic group having 1-3 heteroatoms and wherein one or two ring carbons are optionally replaced with —CO— and which may contain one or two double bonds; or a heteroaryl group having 1-3 heteroatoms (N, O or S); a —CO$_2$R$_{23}$ group; —OCO—R$_{23}$ group; —CON(R$_{24}$)$_2$ group; —OCON(R$_{24}$)$_2$ group; —N(R$_{24}$)$_2$ group; a —SO$_2$—OR$_{23}$ group, —OR$_{23}$ group, —(CH$_2$)m-OR$_{23}$ group, —(CH$_2$)m-N(R$_{24}$)$_2$, where m is 1-8 and each $R_{23}$ or $R_{24}$ is independently hydrogen; an unsubstituted C1-C6 alkyl group; an unsubstituted aryl group having 6-14 carbon atoms; an unsubstituted phenyl group; an unsubstituted benzyl group; an unsubstituted 5- or 6-member ring heterocyclic group, having 1-3 heteroatoms and wherein one or two ring carbons are optionally replaced with —CO— and which may contain one or two double bonds; or a heteroaryl group having 1-3 heteroatoms (N, O or S) and in addition two $R_{24}$ together with the nitrogen to which they are attached can form a heterocyclic or heteroaryl ring moiety, each of which groups or moieties is optionally substituted;

each of which $R_{23}$ and $R_{24}$ groups is in turn optionally substituted with one or more unsubstituted C1-C3 alkyl groups, halogens, oxo groups (=O), nitro groups, cyano groups, —$CO_2R_{25}$ groups, —OCO—$R_{25}$ groups, —CON($R_{26}$)$_2$ groups, —OCO—N($R_{26}$)$_2$ groups, —N($R_{26}$)$_2$ groups, a —$SO_2$—$OR_{25}$ group, —$OR_{25}$ groups, —$(CH_2)$m-$OR_{25}$ groups, —(CH2)m-N($R_{26}$)$_2$ where m is 1-8 and each of $R_{25}$ and $R_{26}$ independently are hydrogen, an unsubstituted C1-C6 alkyl group; an unsubstituted aryl group having 6-14 carbon ring atoms; an unsubstituted phenyl group; an unsubstituted benzyl group, an unsubstituted 5- or 6-member ring heterocyclic group having 1-3 heteroatoms and wherein a ring carbon is optionally replaced with —CO— and which may contain one or two double bonds; or a heteroaryl group having 1-3 heteroatoms (N, O or S) and a total of 5-14 ring atoms; and in addition two $R_{26}$ together with the nitrogen to which they are attached can form an unsubstituted heterocyclic or heteroaryl ring moiety.

In specific embodiments, —[XB]u-[LB]v-[YB]w- is at ring position 4 in formula VIA. In specific embodiments, —[XB]u-[LB]v-[YB]w- is at ring position 4 in formula VIB.

In specific embodiments of formula I having $R_{M1}$ that is a group of formula VIA or VIB, R is hydrogen or methyl, and $R_M$ is an alkyl having 1-6 carbon atoms or an alkynyl having 3 or 4 carbon atoms. In specific embodiments of formula I having $R_M$ that is a group of formula VIA or VIB, R is hydrogen or methyl, and $R_A$ is an alkyl having 1-6 carbon atoms substituted at the para position on the phenyl ring.

In additional embodiments of formula I, $R_M$ or $R_{M1}$ is a phenylboronate group of formula VII:

VII

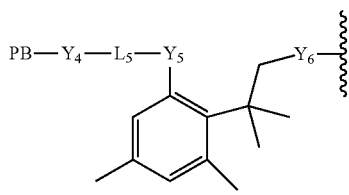

where:

PB is a phenylboronate group (as defined herein above and as in US published patent application 2003/0196433 and US provisional application 62/029,391) 666;

$Y_4$, $Y_5$ and $Y_6$ are independently selected from —O—, —S—, —NRc-, —CO—, —O—CO—, —CO—O—, —CO—NRc-, —NRc-CO—, —NRc-CO—NRc-, —OCO—NRc-, —NRc-CO—O—, —N=N—, —N=N—NRc-, —CO—S—, —S—CO—, —S—S—, —$SO_2$—, —CRc(OH)—CRc(OH)—, where Rc is hydrogen or C1-C3 alkyl; and $L_5$ is a divalent spacer moiety, as defined for -$L_1$- and/or -$L_2$- above.

Such phenylboronate groups can be introduced into a compound of formula I employing a boronation reagent, such as that of formula VIII:

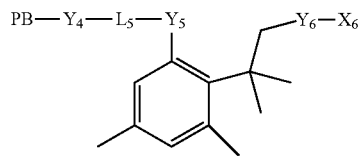

where variables are as defined for formula VII and $X_6$ is a leaving group and —$Y_6$—$X_6$ together is a reactive group and more specifically is an activated ester —$CO_2AC$ (as defined in formula II above).

In specific embodiments of compounds of formula I, wherein $R_{M1}$ is or comprises the group of formula VIII, R is hydrogen or methyl and $R_M$ is an alkyl group having 1-6 carbon atoms or $R_M$ is an alkynyl group having 3-4 carbon atoms. In specific embodiments of compounds of formula I, wherein $R_M$ is or comprises the group of formula VIII, R is hydrogen or methyl and $R_A$ is an alkyl group having 1-6 carbon atoms, and more specifically is a methyl group, substituted at the para position of the phenyl ring.

US published patent applications 2003/0196433 and 2016/0024122 are each incorporated by reference herein in its entirety for description of structures of phenylboronate groups useful in this invention for enhancing cell penetration. These references also provide methods for making phenylboronate groups which can be bonded into compounds of formula 1.

In specific embodiments of formulas herein divalent linkers are selected from the following divalent moieties:
—Y1-$L_1$-Y3-, where Y1 and Y3 are optional and may be the same or different;
—Y1-$L_1$-$L_2$-Y3-, where Y1 and Y3 are optional and may be the same or different and $L_1$ and $L_2$ are different; or —Y1-$L_1$-[$L_2$-Y2]y-$L_3$-Y3-, where Y1 and Y3 are optional, Y1, Y2 and Y3 may be the same or different, $L_1$ and $L_3$ are optional and $L_1$, $L_2$ and $L_3$ may be the same or different and y is an integer indicating the number of repeats of the indicated moiety;

wherein each $L_1$-$L_3$ is independently selected from an optionally substituted divalent aliphatic, alicyclic, heterocyclic, aryl, or heteroaryl moiety having 1 to 30 atoms and each Y1, Y2 and Y3 is independently selected from: —O—, —S—, —NRc-, —CO—, —O—CO—, —CO—O—, —CO—NRc-, —NRc-CO—, —NRc-CO—NRc-, —OCO—NRc-, —NRc-CO—O—, —N=N—, —N=N—NRc-, —CO—S—, —S—CO—, —S—S—, —$SO_2$—, —CRc(OH)—CRc(OH)—, where Rc is hydrogen or C1-C3 alkyl.

In specific embodiments, divalent linkers are selected from:
alkylene linkers (—$(CH_2)_y$—) wherein y is 1-12, and preferably 1-4;
alkoxyalkyl linkers —[$(CH_2)_q$—O—$(CH_2)_r$]$_a$— wherein q and r are zero or integers from 1-4, preferably 0, 1, 2 or 3, as long as one of q and r is not zero, and a is 1-6, preferably 2-4; or
aminoalkyl linkers —[$(CH_2)_s$—$NR_N(CH_2)_t$]$_b$— wherein $R_N$ is hydrogen or a C1-C3 alkyl group, s and t are 0 or integers from 1-4, and are preferably 0, 1 or 2 as long as one of s and t is not zero, and b is 1-3 and preferably is 1.

In specific embodiments of formulas VII and VIII, $L_5$ is —$(CH_2)_2$—.

In a specific embodiment of the reagent of formula VIII, $Y_6$—$X_6$ together is a reactive group that reacts with one or more of an amine group, a carboxylic acid group or ester thereof, a sulfhydryl group, a hydroxyl group, an azide group, a thioester group, a phoshinothioester group, an aldehyde group or a ketone group of an amino acid, peptide or protein.

In specific embodiments of formulas VIII, the boronation reagent has formula IX:

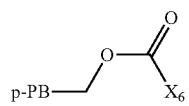

where p-PB is a phenylboronate with the boron in the para position with respect to the —$CH_2$—O—, and $X_6$ is a leaving group. Other boronation agents useful in the present invention are described in US published application 20160067342, which is incorporated by reference herein for descriptions of additional phenylboronate groups of formula VII and reagents of formula VIII.

In an embodiment, $R_M$ or $R_{M1}$ comprises or is a reactive group and more specifically an amine-reactive group. In specific embodiments, $R_M$ is an amine-reactive group or a spacer moiety substituted with an amine-reactive group for forming one or more amide bonds to a cargo molecule comprising one or more amine group. In specific embodiments, $R_M$ comprises or is a latent reactive group or a spacer moiety substituted with a latent reactive group, which latent reactive group does not react with any reactive group in the compound of formula I, or in any other group in the in compound, and which is selectively reactive, or can be selectively activated for reaction, when appropriate. A latent reactive group can, for example, be activated for reaction inside of a cell for example by enzyme action inside of a cell. A latent reactive group can for example be activated by action of an esterase, for example after the compound of formula I is delivered to a cell. In specific embodiments, $R_M$ is a spacer moiety substituted with a reactive group. More specifically, $R_M$ is a spacer moiety comprising a latent reactive group and substituted with a reactive group for forming a bond to a cargo molecule wherein the latent reactive group does not react with the reactive group or the cargo molecule and can be selectively reacted or activated for reaction after the cargo molecule is bonded to the compound of formula I. In specific embodiments, the reactive group of this $R_M$ is an amine-reactive group. In specific embodiments, the compound of formula I comprises a reactive group and a latent reactive group.

In a specific embodiment herein, esterification employing a compound of formula I can be employed to covalently bond, via ester formation, a cargo molecule to a protein or polypeptide. In this case the cargo molecule is desired to be targeted to a cell, for example, by the protein, polypeptide or peptide to which it is covalently bound. In this embodiment, the protein, polypeptide or peptide to which the compound of formula I is esterified functions for cell targeting. The targeting protein, polypeptide or peptide can be an antibody or functional fragment thereof. The protein, polypeptide or peptide can be a ligand for a cell surface receptor. The cargo molecule can itself be a protein, polypeptide or peptide other than the targeting protein, polypeptide or peptide. The cargo molecule can be a species other than a protein, polypeptide or peptide. The cargo molecule can, employing the esterification methods described herein, further comprise a label and/or a cell penetrating group. In this embodiment, the esterified protein or polypeptide is contacted with cells for enhanced uptake into cells.

In an embodiment, $R_M$ or $R_{M1}$ is or comprises a polymer which can function for protection of a protein in the bloodstream or to enhance pharmokinetics of the protein. In an embodiment, $R_M$ or $R_{M1}$ is or comprises polyethylene glycol. In more specific embodiments, the polyethylene glycol has average molecular weight ranging from 200 to 10,000. In more specific embodiments, the polyethylene glycol has average molecular weight ranging from 1,000 to 10,000. In more specific embodiments, the polyethylene glycol has average molecular weight ranging from 2,000 to 10,000. In more specific embodiments, the polyethylene glycol has average molecular weight ranging from 2,000 to 6,000. In more specific embodiments, the polyethylene glycol has number average molecular weight (Mn) ranging from 200 to 10,000, 1,000 to 10,000, 2,000 to 10,000, or from 2,000 to 6,000. Functionalized polyethylene glycol polymers useful for preparation of compounds of formula 1 are commercially available or can be prepared by well-known methods. See for example, The Sigma-Aldrich Catalogue.

In an embodiment, $R_M$ or $R_{M1}$ is or comprises biotin or a derivative thereof. In specific embodiments, the biotin derivative is any biotin derivative known in art and useful for biotinylation of a chemical or biochemical species, such as a protein, polypeptide or peptide. Biotin derivatives include labelled biotin, such as radiolabelled biotin, isotopically labelled biotin, biotin labelled with a fluorescent or other dye, or the like. Functionalized biotins, such as amine functionalized biotin, useful in the preparation of compounds of formula I containing biotin or a derivative thereof are known in the art and/or commercially available. (See, for example, Sigma-Aldrich Catalogue). Esterification of a cargo molecule, such as a protein with a compound of formula I which comprises biotin or a derivative thereof (e.g., a labelled biotin) can provide for biotinylation of the cargo molecule for any know purpose. For example, functionalization of a protein with biotin can be employed for protein capture or isolation, for example, for protein pull-down or for biotin affinity purification. Thus, the invention provides a method for biotinylating a cargo molecule or more simply a protein, polypeptide or peptide employing a compound of formula I where $R_M$ or $R_{M1}$ is or comprises biotin or a derivative thereof.

Diazo compounds of formula I can be synthesized in view of the examples provided herein and in U.S. Pat. No. 8,350,014 and in further view of what is well-known in the art. Methods herein can be routinely adapted by choice of starting materials, solvents and reagents as known in the art to prepare compounds of formula I not specifically exemplified. $R_M$ and $R_{M1}$ groups comprising labels, cell penetrating groups, or cell targeting groups can for example be in introduced into the compounds of formula I employing bioconjugation methods as found in Hermanson, G. T. *Bioconjugation Techniques* ($2^{nd}$ Ed.) 2008 Academic Press/Elsevier London, UK. This reference also contains detailed descriptions of homobifunctional and heterobifunctional crossing linking reagents which can be employed to covalently attach a $R_{M1}$ and $R_M$ groups in compounds of formula I. U.S. Pat. No. 8,350,014 is incorporated by reference herein in its entirety for descriptions of synthesis of diazo compounds.

Diazo compounds of formula I carrying one or more reactive or latent reactive groups can be prepared in view of methods herein and what is well-known in the art. For example, methods as described in Josa-Cullere (2014) [39] and Ma, M. et al. (2005) [40] can be employed to prepare compounds of formula I having NHS esters.

The terms alkyl or alkyl group refer to a monoradical of a straight-chain or branched saturated hydrocarbon. Alkyl groups include straight-chain and branched alkyl groups. Unless otherwise indicated alkyl groups have 1-20 carbon atoms (C1-C20 alkyl groups) and preferred are those that contain 1-10 carbon atoms (C1-C10 alkyl groups) and more preferred are those that contain 1-6 carbon atoms (C1-C6 alkyl groups) and. those that contain 1-3 carbon atoms (C1-C3 alkyl groups) Alkyl groups are optionally substituted with one or more non-hydrogen substituents as described herein. Exemplary alkyl groups include methyl, ethyl, n-propyl, iso-propyl, n-butyl, s-butyl, t-butyl, n-pentyl, branched-pentyl, n-hexyl, branched hexyl, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl.

A carbocyclyl group is a group having one or more saturated or unsaturated carbon rings. Carbocyclyl groups, for example, contain one or two double bonds. One or more carbons in a carbocyclic ring can be —CO— groups. Carbocyclyl groups include those having 3-12 carbon atoms, and optionally replacing 1 or 2 carbon atoms with a —CO— group and optionally having 1, 2 or 3 double bonds. Carbocyclyl groups include those having 5-6 ring carbons. Carbocyclyl groups can contain one or more rings each of which is saturated or unsaturated. Carbocyclyl groups include bicyclic and tricyclic groups. Preferred carbocyclic groups have a single 5- or 6-member ring. Carbocyclyl groups are optionally substituted as described herein. Specifically, carbocyclic groups can be substituted with one or more alkyl groups. Carbocyclyl groups include among others cycloalkyl and cycloalkenyl groups.

Cycloalkyl groups include those which have 1 ring or which are bicyclic or tricyclic. In specific embodiments, cycloalkyl groups have 1 ring having 5-8 carbon atoms and preferably have 5 or 6 carbon atoms.

Cycloalkenyl groups include those which have 1 ring or which are bicyclic or tricyclic and which contain 1-3 double bond. In specific embodiments, cycloalkenyl groups have 1 ring having 5-8 carbon atoms and preferably have 5 or 6 carbon atoms and have one double bond.

Alkenyl groups include monovalent straight-chain, branched and cyclic alkenyl groups which contain one or more carbon-carbon double bonds. Unless otherwise indicated alkenyl groups include those having from 2 to 20 carbon atoms. Alkenyl groups include those having 2 to 4 carbon atoms and those having from 5-8 carbon atoms. Cyclic alkenyl groups include those having one or more rings wherein at least one ring contains a double bond. Cyclic alkenyl groups include those which have 1, 2 or 3 rings wherein at least one ring contains a double bond. Cyclic alkenyl groups also include those having 3-10 carbon atoms. Cyclic alkenyl groups include those having a 5-, 6-, 7-, 8-, 9- or 10-member carbon ring and particularly those having a 5- or 6-member ring. The carbon rings in cyclic alkenyl groups can also carry straight-chain or branched alkyl or alkenyl group substituents. Cyclic alkenyl groups can include bicyclic and tricyclic alkyl groups wherein at least one ring contains a double bond. Alkenyl groups are optionally substituted with one or more non-hydrogen substituents as described herein. Specific alkenyl groups include ethylene, propenyl, cyclopropenyl, butenyl, cyclobutenyl, pentenyl, pentadienyl, cyclopentenyl, cyclopentadienyl, hexylenyl, hexadienyl, cyclohexenyl, cyclohexadienyl, including all isomers thereof and all of which are optionally substituted. Substituted alkenyl groups include fully halogenated or semihalogenated alkenyl groups.

Alkynyl groups include mono-valent straight-chain, branched and cyclic alkynyl group which contain one or more carbon-carbon triple bonds. Unless otherwise indicated alkynyl groups include those having from 2 to 20 carbon atoms. Alkynyl groups include those having 2 to 4 carbon atoms and those having from 5-8 carbon atoms. Cyclic alkynyl groups include those having one or more rings wherein at least one ring contains a triple bond. Cyclic alkynyl groups include those which have 1, 2 or 3 rings wherein at least one ring contains a triple bond. Cyclic alkynyl groups also include those having 3-10 carbon atoms. Cyclic alkynyl groups include those having a 5-, 6-, 7-, 8-, 9- or 10-member carbon ring and particularly those having a 5- or 6-member ring.

The carbon rings in cyclic alkynyl groups can also carry straight-chain or branched alkyl, alkenyl or alkynyl group substituents. Cyclic alkynyl groups can include bicyclic and tricyclic alkyl groups wherein at least one ring contains a triple bond. Alkynyl groups are optionally substituted with one or more non-hydrogen substituents as described herein.

An alkoxy group is an alkyl group (including cycloalkyl), as broadly discussed above, linked to oxygen, a monovalent —O-alkyl group. An aryloxy group is an aryl group, as discussed above, linked to an oxygen, a monovalent —O-aryl. A heteroaryloxy group is a heteroaryl group as discussed above linked to an oxygen, a monovalent —O-heteroaryl. Alkenoxy, alkynoxy, alicycloxy, heterocycloxy groups are analogously defined. All of such groups are optionally substituted.

An aliphatic group as used herein refers to a monovalent non-aromatic hydrocarbon group which include straight chain, branched, or cyclic hydrocarbon groups which can be saturated or unsaturated with one or more double bonds or one or more triple bonds. Aliphatic groups may contain portions which are straight-chain or branched in combination with one or more carbon rings. Carbon rings of aliphatic groups may contain one or more double bonds or one or more triple bonds. Carbon rings of aliphatic groups can contain 3- to 10-membered rings. Such carbon rings may be fused and may be bicyclic or tricyclic. Aliphatic groups are optionally substituted with one or more non-hydrogen substituents where optional substituents are described herein. Unless otherwise specified, an aliphatic group can contain 1-20 carbon atoms or can contain 1-10 carbon atoms. Aliphatic groups include those containing 1-3, 1-6, and 1-8 carbon atoms. Aliphatic groups include, among others, alicyclic groups, alkyl groups, alkenyl groups and alkynyl groups.

Heteroaliphatic groups refer generally to aliphatic groups having 1 or more heteroatoms (other than C and H). Specifically heteroatoms of heteroaliphatic groups are selected from N, P, B, O or S. In more specific embodiments, heteroaliphatic groups contain one or more oxygens, nitrogen or sulfur atoms.

An alicylic group as used herein refers to a monovalent non-aromatic cyclic hydrocarbon group which can be saturated or unsaturated with one or more double bonds or one or more triple bonds. Alicyclic rings include those containing 3- to 10-membered carbon rings. Alicyclic groups include those containing one, two, three or more rings which may be fused or linked by straight chain or branched alkylene, alkenylene or alkynylene moieties. Alicyclic groups include bicyclic and tricyclic rings. Alicyclic groups include those in which one or more carbon rings are substituted with a straight-chain or branched alkyl, alkenyl or alkynyl group. To satisfy valence requirements, a ring atom may be substituted with hydrogen or optionally with non-hydrogen substituents as described herein. One or more carbons in an alicyclic group can be —CO— groups, i.e. a carbon can be substituted with an oxo (=O) moiety. Alicyclic groups are optionally substituted with one or more non-hydrogen substituents where optional substituents are described herein. Unless otherwise specified, an alicyclic group can contain 3-20 carbon atoms or can contain 3-12 carbon atoms. Alicyclic groups include those containing 3-6 and 3-8 carbon atoms. Alicyclic groups include among others cycloalkyl, cycloalkenyl, cyclopropyl, cyclobutyl, cyclopentyl, cyclopentadienyl, cyclohexyl, cyclohexenyl and cyclohexadienyl groups, all of which are optionally substituted.

The number of carbon atoms in a given group, such as an alkyl group, can be indicated herein using the expression "Cm" where m is the number of carbon atoms. Thus, the expression "Cm1-Cm2" modifying a given chemical group indicates that the group can contain from m1 to m2 carbon atoms. For example, a C1-C6 alkyl group contains 1 to 6 carbon atoms, exclusive of carbons in any substituent on the alkyl group. Similar expressions can be used to indicate the number of atoms of N (nitrogen), O (oxygen) or other elements in a given group.

A heterocyclyl (or heterocyclic) group is a group having one or more saturated or unsaturated carbon rings and which contains one to three heteroatoms (e.g., N, O or S) per ring. These groups optionally contain one, two or three double bonds. To satisfy valence requirement, a ring atom may be substituted as described herein. One or more carbons in the heterocyclic ring can be —CO— groups. Heterocyclyl groups include those having 3-12 carbon atoms, and 1-6, heteroatoms, wherein 1 or 2 carbon atoms are replaced with a —CO— group. Heterocyclyl groups include those having 3-12 or 3-10 ring atoms of which up to three can be heteroatoms other than carbon. Heterocyclyl groups can contain one or more rings each of which is saturated or unsaturated. Heterocyclyl groups include bicyclic and tricyclic groups. Preferred heterocyclyl groups have 5- or 6-member rings. Heterocyclyl groups are optionally substituted as described herein. Specifically, heterocyclic groups can be substituted with one or more alkyl groups. Heterocyclyl groups include those having 5- and 6-member rings with one or two nitrogens and one or two double bonds. Heterocyclyl groups include those having 5- and 6-member rings with an oxygen or a sulfur and one or two double bonds. Heterocyclyl group include those having 5- or 6-member rings and two different heteroatom, e.g., N and O, O and S or N and S. Specific heterocyclyl groups include among others among others, pyrrolidinyl, piperidyl, piperazinyl, pyrrolyl, pyrrolinyl, furyl, thienyl, morpholinyl, oxazolyl, oxazolinyl, oxazolidinyl, indolyl, triazoly, and triazinyl groups.

Aryl groups include groups having one or more 5- or 6-member aromatic rings. Aryl groups can contain one, two or three, 6-member aromatic rings. Aryl groups can contain two or more fused aromatic rings. Aryl groups can contain two or three fused aromatic rings. Aryl groups are optionally substituted with one or more non-hydrogen substituents. Substituted aryl groups include among others those which are substituted with alkyl or alkenyl groups, which groups in turn can be optionally substituted. Specific aryl groups include phenyl groups, biphenyl groups, and naphthyl groups, all of which are optionally substituted as described herein. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogen replaced with one or more fluorine atoms.

Heteroaryl groups include groups having one or more aromatic rings in which at least one ring contains a heteroatom (a non-carbon ring atom). Heteroaryl groups include those having one or two heteroaromatic rings carrying 1, 2 or 3 heteroatoms and optionally have one 6-member aromatic ring. Heteroaryl groups can contain 5-20, 5-12 or 5-10 ring atoms. Heteroaryl groups include those having one aromatic ring contains a heteroatom and one aromatic ring containing carbon ring atoms. Heteroaryl groups include those having one or more 5- or 6-member aromatic heteroaromatic rings and one or more 6-member carbon aromatic rings. Heteroaromatic rings can include one or more N, O, or S atoms in the ring. Heteroaromatic rings can include those with one, two or three N, those with one or two O, and those with one or two S, or combinations of one or two or three N, O or S. Specific heteroaryl groups include furyl, pyridinyl, pyrazinyl, pyrimidinyl, quinolinyl, and purinyl groups. In specific embodiments herein aryl groups contain no heteroatoms in the aryl rings. Aryl including heteroaryl groups are optionally substituted.

Heteroatoms include O, N, S, P or B. More specifically heteroatoms are N, O or S. In specific embodiments, one or more heteroatoms are substituted for carbons in aromatic or carbocyclic rings. To satisfy valence any heteroatoms in such aromatic or carbocyclic rings may be bonded to H or a substituent group, e.g., an alkyl group or other substituent.

Heteroarylalkyl groups are alkyl groups substituted with one or more heteroaryl groups wherein the alkyl groups optionally carry additional substituents and the aryl groups are optionally substituted.

Alkylaryl groups are aryl groups substituted with one or more alkyl groups wherein the alkyl groups optionally carry additional substituents and the aryl groups are optionally substituted. Specific alkylaryl groups are alkyl-substituted phenyl groups such as methylphenyl.

Arylalkyl groups are alkyl groups substituted with one or more aryl groups, typically one aryl group. The aryl group is optionally substituted. Specific arylakly groups include benzyl, optionally substituted benzyl, phenethyl, and optionally substituted phenethyl.

Alkylheteroaryl groups are heteroaryl groups substituted with one or more alkyl groups wherein the alkyl groups optionally carry additional substituents and the aryl groups are optionally substituted.

An alkoxy group is an alkyl group, as broadly discussed above, linked to oxygen ($R_{alkyl}$—O—). An aryloxy group is an aryl group, as discussed above, linked to an oxygen ($R_{aryl}$—O—). A heteroaryloxy group is a heteroaryl group as discussed above linked to an oxygen ($R_{heteroaryl}$—O—). A carbocyclyloxy group is an carbocyclyl group, as broadly discussed above, linked to oxygen ($R_{carbocyclyl}$—O—). A heterocyclyloxy group is an carbocyclyl group, as broadly discussed above, linked to oxygen ($R_{heterocyclyl}$—O—).

An acyl group is an R'—CO group where R' in general is a hydrogen, an alkyl, alkenyl or alkynyl, aryl or heteroaryl group as described above. In specific embodiments, acyl groups have 1-20, 1-12 or 1-6 carbon atoms and optionally 1-3 heteroatom, optionally one double bond or one triple bond. In specific embodiments, R is a C1-C6 alkyl, alkenyl or alkynyl group. cyclic configuration or a combination thereof, attached to the parent structure through a carbonyl functionality. Examples include acetyl, benzoyl, propionyl, isobutyryl, or oxalyl. The R' group of acyl groups are optionally substituted as described herein. When R' is hydrogen, the group is a formyl group. An acetyl group is a $CH_3$—CO— group. Another exemplary acyl group is a benzyloxy group.

An alkylthio group is an alkyl group, as broadly discussed above, linked to a sulfur ($R_{alkyl}$—S—) An arylthio group is an aryl group, as discussed above, linked to a sulfur ($R_{aryl}$—S—). A heteroarylthio group is a heteroaryl group as discussed above linked to an sulfur ($R_{heteroaryl}$—S—). A carbocyclylthio group is an carbocyclyl group, as broadly discussed above, linked to oxygen ($R_{carbocyclyl}$—S—). A heterocyclylthio group is an carbocyclyl group, as broadly discussed above, linked to oxygen ($R_{heterocyclyl}$—S—).

The term amino group is refer to the species —N(H)$_2$—. The term alkylamino refers to the species —NHR" where R" is an alkyl group, particularly an alkyl group having 1-3 carbon atoms. The term dialkylamino refers to the species —NR"$_2$ where each R" is independently an alkyl group, particularly an alkyl group having 1-3 carbon atoms.

Groups herein are optionally substituted most generally with one or more alky, alkenyl, alkynyl, and aryl, heteroaryl, carbocyclyl, and heterocyclyl groups can be substituted, for example, with one or more oxo group, thioxo group, halogen, nitro, cyano, cyanate, azido, thiocyano, isocyano, isothiocyano, sulfhydryl, hydroxyl, alkyl, alkoxy, alkenyl, alkenyloxy, alkynyl, alkynyloxy, aryl, aryloxy, heteroaryl, heteroaryloxy, carbocyclyl, carbocyclyloxy, heterocyclyl, heterocyclyloxy, alkylthio, alkenylthio, alkynylthio, arylthio, thioheteroaryl, thioheteroaryl, thiocarbocyclyl, thioheterocyclyl, —CORs, —COH, —OCORs, —OCOH, —CO—ORs, —CO—OH, —CO—O—CO—Rs, —CON(Rs)$_2$, —CONHRs, —CONH$_2$, —NRs-CORs, —NHCORs, —NHRs, —N(Rs)$_2$, —O—SO$_2$—Rs, —SO$_2$—Rs, —SO$_2$—NHRs, —SO$_2$—N(Rs)$_2$, —NRs-SO$_2$—Rs, —NH—SO$_2$—Rs, —NRsCO—N(Rs)$_2$, —NH—CO—NHRs, —O—PO(ORs)$_2$, —O—PO(ORs)(N(Rs)$_2$), —O—PO(N(Rs)$_2$)$_2$, —N—PO(ORs)$_2$, —N—PO(ORs)(N(Rs)$_2$), —P(Rs)$_2$, —B(OH)$_2$, —B(OH)(ORs), —B(ORs)$_2$, where each Rs independently is an organic group and more specifically is an alkyl, alkenyl, alkynyl, aryl, heteroaryl, carbocyclyl, or heterocyclyl group or two Rs within the same substituent can together form a carbocyclic or heterocyclic ring having 3 to 10 ring atoms. Organic groups of non-hydrogen substituents are in turn optionally substituted with one or more halogens, nitro, cyano, isocyano, isothiocyano, hydroxyl, sulfhydryl, haloalkyl, hydroxyalkyl, amino, alkylamino, dialkylamino, arylalkyl, unsubstituted alkyl, unsubstituted alkenyl, unsubstituted alkynyl alkylalkenyl, alkylalkynyl, haloaryl, hydroxylaryl, alkylaryl, unsubstituted aryl, unsubstituted carbocylic, halo-substituted carbocyclic, hydroxyl-substituted carbocyclic, alkyl-substituted carbocyclic, unsubstituted heterocyclic, unsubstituted heteroaryl, alkyl-substituted heteroaryl, or alkyl-substituted heterocyclic. In specific embodiments, Rs groups of substituents are independently selected from alkyl groups, haloalkyl groups, phenyl groups, benzyl groups and halo-substituted phenyl and benzyl groups. In specific embodiments, non-hydrogen substituents have 1-20 carbon atoms, 1-10 carbon atoms, 1-7 carbon atoms, 1-5 carbon atoms or 1-3 carbon atoms. In specific embodiments, non-hydrogen substituents have 1-10 heteroatoms, 1-6 heteroatoms, 1-4 heteroatoms, or 1, 2, or 3 heteroatoms. Heteroatoms include O, N, S, P, B and Se and preferably are O, N or S.

In specific embodiments, optional substitution is substitution with 1-12 (or 1-3 or 1 to 3 or 1 to 6) non-hydrogen substituents. In specific embodiments, optional substitution is substitution with 1-6 non-hydrogen substituents. In specific embodiments, optional substitution is substitution with 1-3 non-hydrogen substituents. In specific embodiments, optional substituents contain 6 or fewer carbon atoms. In specific embodiments, optional substitution is substitution by one or more halogen, hydroxyl group, cyano group, oxo group, thioxo group, unsubstituted C1-C6 alkyl group or unsubstituted aryl group. The term oxo group and thioxo group refer to substitution of a carbon atom with a =O or a =S to form respectively —CO— (carbonyl) or —CS— (thiocarbonyl) groups.

In specific embodiments, non-hydrogen substituents for optional substitution include alkyl, alkoxy, halogen (F, Cl, Br or I and preferably Cl or F), haloalkyl, or haloalkoxy. In specific embodiments, non-hydrogen substituents for optional substitution include methyl, ethyl, methoxy, ethoxy, F, Cl, and trifluormethyl.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RsCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

Compounds of the invention may contain chemical groups (acidic or basic groups) that can be in the form of salts. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines

[formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Salts of the invention include "pharmaceutically acceptable salts" which refers to those salts which retain the biological effectiveness and properties of the free bases or free acids, and which are not biologically or otherwise undesirable. Pharmaceutically acceptable salts comprise pharmaceutically-acceptable anions and/or cations.

Compounds of the present invention, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention.

Additionally, inventive compounds may have trans and cis isomers and may contain one or more chiral centers, therefore exist in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form. With respect to the various compounds of the invention, the atoms therein may have various isotopic forms, e.g., isotopes of hydrogen include deuterium and tritium. All isotopic variants of compounds of the invention are included within the invention and particularly included at deuterium and $^{13}C$ isotopic variants. It will be appreciated that such isotopic variants may be useful for carrying out various chemical and biological analyses, investigations of reaction mechanisms and the like. Methods for making isotopic variants are known in the art.

In embodiments of the methods herein a cargo molecule is esterified with a compound of formula I herein and a cell or tissue is contacted with the esterified cargo molecule. Contacting with a cell or tissue is typically carried out in an aqueous buffer suitable for the cell or tissue. Contacting is typically carried out in an aqueous buffer of appropriate pH which can be readily selected by one of ordinary skill in the art. Typically, contacting is carried out at pH ranging from 5 to 8. Contacting can include administration to an organism or individual. Any suitable form of administration can be employed in the methods herein. The esterified cargo molecules of this invention can, for example, be administered orally, topically, intravenously, intraperitoneally, subcutaneously, or intramuscularly, in any suitable dosage forms well known to those of ordinary skill in the pharmaceutical arts. The esterified cargo molecules are optionally administered with a pharmaceutical carrier selected upon the basis of the chosen route of administration and standard pharmaceutical practice, such as, for example, as described in Remington's Pharmaceutical Sciences, 17th edition, ed. Alfonoso R. Gennaro, Mack Publishing Company, Easton, Pa. (1985), which is incorporated herein by reference in its entirety for suitable administration and carriers.

Cargo molecules include nucleic acids, peptides, proteins, small molecule drugs, reporters and labeling (fluorescent labels or isotopic labels for example), imaging agents, contrast agents, particles carrying reactive functional groups, quantum dots carrying reactive functional groups, among others. In general any cargo molecule that it is desired to introduce into a cell can be employed in the methods of this invention. Cargo molecules include those having a biological activity. In specific embodiments, biological activity of interest of the cargo molecule is retained on esterification or is recovered on selective removal of esterification after delivery to a cell. In a specific embodiment, the esterified cargo molecule retains at least 10% of a selected biological activity of the cargo molecule prior to esterification. In other specific embodiments, the esterified cargo molecule retains at least 50% of a selected biological activity of the cargo molecule prior to esterification. In a further specific embodiment, the esterified cargo molecule retains at least 80% of the activity of the cargo molecule prior to esterification.

In a specific embodiment, the cargo protein is an enzyme. In a specific embodiment, the cargo protein is glycosylated (i.e., is a glycoprotein). In a specific embodiment, the cargo protein is not glycosylated (i.e., is not a glycoprotein). In a specific embodiment, the esterified cargo peptide or protein retains at least 10% of a selected biological activity of the protein prior to esterification. In other specific embodiments, esterified cargo peptide or protein retains at least 50% of a selected biological activity of the protein prior to esterification. In a further specific embodiment, the esterified cargo peptide or protein retains at least 80% of the activity of the peptide or protein prior to esterification. Peptides and proteins include those having enzyme activity.

Cargo peptides include peptide ligands, cytotoxic peptides, bioactive peptides, diagnostic agents, among others. Cargo peptides include those having 2-1000 amino acids, 2-500 amino acids, 2-250 amino acids, 2-100 amino acids, 2-50 amino acids, and 2-25 amino acids and 2-10 amino acids.

Peptides and proteins include antibodies and functional fragments thereof, where the term antibody is used broadly herein. More specifically, antibodies include among others, monoclonal antibodies including humanized antibodies, human antibodies, interspecies antibodies, chimeric antibodies, human monoclonals, humanized monoclonals, interspecies antibodies made by any art-known methods. Functional fragments of antibodies include F(ab')2, F(ab)2, Fab', Fab, Fv, among others, as well as hybrid fragments. Additionally, antibodies include subfragments retaining the hypervariable, antigen-binding region of an immunoglobulin and preferably having a size similar to or smaller than a Fab' fragment. Such fragments and subfragments, including single chain fragments or multiple chain fragments, which incorporate an antigen-binding site and exhibit antibody function, are known in the art and can be prepared by methods that are well-known in the art, including by methods of preparing recombinant proteins. Antibodies and fragments thereof include therapeutic antibodies which are known in the art [35]. This reference is incorporated by reference herein in its entirety for descriptions of therapeutic antibodies which can be employed in the present invention.

In a specific embodiment, the cargo molecule is a nucleic acid which may be RNA or DNA, or an analog of a nucleic acid which may be a peptide nucleic acid, a locked nucleic acid, or a phosphoramidate-morpholino oligomer. Other art-known nucleic acid analogs include carbamate-linked DNA, phosphorothioate-linked DNA, 2'-O-methyl RNA, phosphotriester-linked DNA or methylphosphonate-linked DNA. The cargo nucleic acid can be single- or double-stranded. The nucleic acid can be an oligonucleotide or analog thereof having 2-100, 2-50 or 2-25 bases. The nucleic acid can be siRNA, microRNA, antisense oligonucleotides, decoy DNA, plasmids or other nucleic acid structures such as minicircles. Nucleic acids and analogs thereof are available from commercial sources, can be isolated from natural source or can be prepared by methods that are well-known in the art.

In a specific embodiment, the esterified cargo nucleic acid retains at least 10% of a selected biological activity of the nucleic acid prior to esterification. In other specific embodiments, the esterified cargo nucleic acid retains at least 50% of a selected biological activity of the nucleic acid prior to esterification. In a further specific embodiment, the esterified cargo nucleic acid retains at least 80% of the activity of the nucleic acid prior to esterification. In a specific embodiment, the biological activity of the nucleic acid that is retained is binding to a complementary nucleic acid or binding to another biological molecule (e.g., a peptide or protein).

Cargo nucleic acids include those having 2-1000 bases, 2-500 bases, 2-250 bases, 2-100 bases, 2-50 bases, and 2-25 bases and 2-10 bases. Nucleic acids include nucleosides and analogs thereof.

In specific embodiments, cargo molecules include transcription factors (proteins) which affect transcription of DNA to messenger RNA and thus affect expression of one or more genes. In specific embodiments, transcription factors include one or more DNA-binding domains. Transcription factors include, among others, tumor suppressors. A specific transcription factor of potential clinical interest is FOXO3 which functions as a trigger for apoptosis (36). One or more diazo-compounds of formula I can be employed to esterify transcription factors, including FOXO transcription factors, and more specifically FOXO3 to facilitate cell uptake thereof. Employing the reversible diazo esterification reagents herein, esterified groups are removed after cell uptake.

In specific embodiments, cargo molecules include proteins that function as tumor suppressors. For example, cargo molecules include PTEN which is a phosphatidylinositol-3,4,5-trisphosphate 3-phosphatase (Hopkins, et al. 2013, 7) PTEN contains a tensin-like domain as well as a phosphatase catalytic domain. PTEN negatively regulates the Akt/PKB signaling pathway functioning as a tumor suppressor. One or more diazo compounds of this invention carrying a cell penetrating group can be employed to esterify PTEN to facilite cell uptake thereof. Employing the reversible esterification reagents herein, esterified groups are removed after cell uptake. In a specific embodiment, the cargo molecule is SCRIB, a scaffold protein which is involved in cell migration, cell polarity and cell proliferation [37]. One or more diazo compounds of this invention carrying a cell penetrating group, such as a fluorenyl, can be employed to esterify SCRIB to facilite cell uptake thereof. Employing the reversible esterification reagents herein, esterified groups are removed after cell uptake to facilitate entry into the cytosol of the cell.

In specific embodiments exemplified herein, diazo compounds of this invention can be employed to esterify GFP (Green fluorescent protein) with one or more cell penetrating groups to facilitate cellular uptake of the fluorescent protein. The diazo compounds herein can be employed with various fluorescent proteins that are known in the art to facilitate their uptake into cells.

The present invention provides a method of reversibly esterifying cargo molecules having one or more or two or more carboxylate groups for labeling, or targeting and cellular uptake, wherein the ester groups are removable by ester cleavage after cellular uptake.

Cellular uptake includes at least in part uptake into the cytosol. In specific embodiments, the method employs diazo compounds of formula I to react with carboxylate groups on the cargo molecule to form esters. Preferably 2 or more carboxylate groups of the cargo molecule are reacted to covalently attach cell penetrating groups, for example via ester linkages. After esterification the cargo molecule is placed in contact with a cell or tissue and the esterified cargo molecule is taken up into the cell and at least in part into the cytosol. After uptake into the cell, the ester groups are removed within the cell, for example, by the action of cellular enzymes (e.g., esterases).

All references throughout this application, for example patent documents including issued or granted patents or equivalents; patent application publications; and non-patent literature documents or other source material; are hereby incorporated by reference herein in their entireties, as though individually incorporated by reference.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination.

One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

THE EXAMPLES

Example 1: General Experimental

Materials.

Silica gel (40 μm; 230-400 mesh) was from SiliCycle. Reagents were obtained from commercial sources and used without further purification. Dichloromethane (DMC) and tetrahydrofuran were dried over a column of alumina. Thin-layer chromatography (TLC) was performed on plates of EMD 250 μm silica 60-$F_{254}$.

Solvent Removal.

The phrase "concentrated under reduced pressure" refers to the removal of solvents and other volatile materials using a rotary evaporator at water aspirator pressure (<20 torr) while maintaining a water bath below 40° C. Residual solvent was removed from samples at high vacuum (<0.1 torr).

NMR Spectroscopy.

$^1$H and $^{13}$C NMR spectra for all compounds were acquired with Bruker spectrometers in the National Magnetic Resonance Facility at Madison operating at 400, 500, 600, or 750 MHz. Chemical shift data are reported in units of δ ☐ppm) relative to an internal standard (residual solvent or TMS).

Mass Spectrometry.

Electrospray ionization (ESI) mass spectrometry for small-molecule characterization was performed with a Micromass LCT at the Mass Spectrometry Facility in the Department of Chemistry at the University of Wisconsin-Madison. Matrix-assisted laser desorption-ionization-time-of-flight (MALDI-TOF) mass spectrometry for protein characterization was performed with a Voyager DE-Pro instrument at the Biophysics Instrumentation Facility at the University of Wisconsin-Madison.

Abbreviations:

AIBN (azobisisobutyroisonitrile); EtOAc (ethyl acetate); DCC (N,N', dicyclohexylcarbodiimide); DBU (1,8-diazabicyclo[5.4.0] undec-7-ene); THF (tetrahydrofuran); MES (2-(N-morpholino)ethanesulfonic acid; DCM (dichloromethane).

Example 2: Synthesis and Characterization Data

Preparation of α-Bromoacid S1

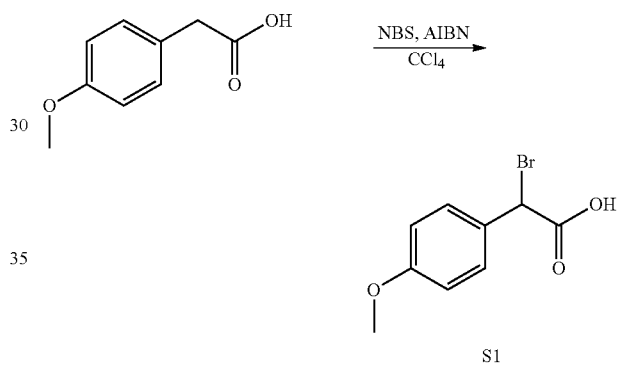

4-Methoxyphenylacetic acid (5.000 g, 30.10 mmol) was dissolved in $CCl_4$ (50 mL). N-Bromosuccinimide (NBS, 5.625 g, 31.6 mmol) and AIBN (0.985 g, 6.0 mmol) were added. The resulting solution was heated to 80° C. and allowed to reflux overnight. The succinimide by-product was removed by filtration, and the solution was concentrated under reduced pressure. The residue was purified by chromatography on silica gel, eluting with 1:1 EtOAc/hexanes to afford S1 (5.705 g, 78%) as a white solid.

Data for S1:

$^1$H NMR (500 MHz, $CDCl_3$, δ): 7.50 (d, 2H, J=8.8 Hz), 6.90 (d, 2H, J=8.8 Hz), 5.36 (s, 1H), 3.82 (s, 1H.) $^{13}$C NMR (125 MHz, $CDCl_3$, δ): 173.4, 160.5, 130.2, 126.8, 114.3, 55.4, 45.9, HRMS (ESI$^-$) m/z calcd for $C_9H_9BrO_3$ [M−H]$^-$ 242.9662; found, 242.9660.

Preparation of α-Azido Acid S2

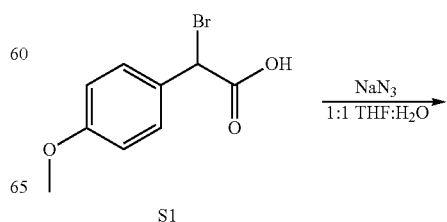

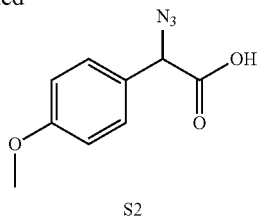

S2

α-Bromo-4-methoxyphenylacetic acid S1 (0.802 g, 3.3 mmol) was dissolved in 1:1 THF/H$_2$O (4 mL). Sodium azide (0.429 g, 6.6 mmol) was added, and the resulting solution was stirred overnight. The solution was then concentrated under reduced pressure, and the residue was dissolved in EtOAc (50 mL). The resulting solution was washed with 0.1 M HCl (2×50 mL). The organic layer was dried over anhydrous Na$_2$SO$_4$(s) and concentrated under reduced pressure to afford S2 (0.412 g, 62%) as a white solid.

Data for S2:
$^1$H NMR (500 MHz, CDCl$_3$, δ): 7.35 (d, 2H, J=8.7 Hz), 6.95 (d, 2H, J=8.7 Hz), 5.00 (s, 1H), 3.83 (s, 3H). $^{13}$C NMR (125 MHz, CDCl$_3$, δ): 173.5, 160.5, 129.1, 125.2, 114.6, 64.6, 55.4, HRMS (ESI$^-$) m/z calcd for C$_9$H$_9$N$_3$O$_3$ [M–H]$^-$ 206.0571; found, 206.0577.

Preparation of α-Azido 4-Methoxyphenylacetic Amide S3

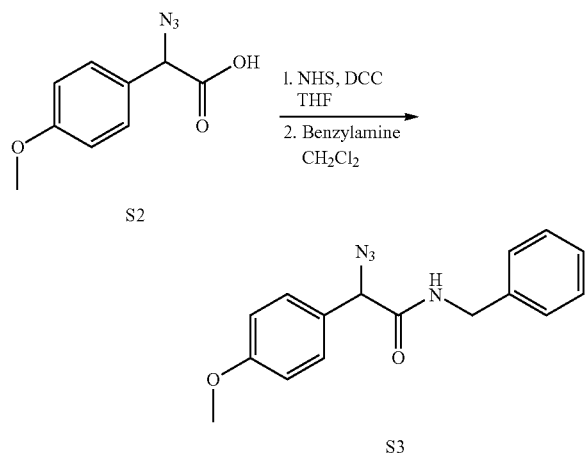

α-Azido-4-methoxyphenylacetic acid S2 (0.412 g, 2.0 mmol) was dissolved in THF (5 mL), and the resulting solution was cooled in an ice bath. N-Hydroxysuccinimide (NHS, 0.230 g, 2.0 mmol) was added, followed by the portion-wise addition of DCC (0.453 g, 2.2 mmol). The resulting solution was warmed to ambient temperature and stirred overnight. The slurry was removed by filtration, and the solution was concentrated under reduced pressure. The residue was dissolved in EtOAc (10 mL) and washed with saturated aqueous NaHCO$_3$ (2×10 mL). The organic layer was dried over anhydrous Na$_2$SO$_4$(s) and concentrated under reduced pressure. The residue was purified by chromatography on silica gel, eluting with 3:7 EtOAc/hexanes, and used immediately. The NHS ester (0.4 g, 1.2 mmol) was dissolved in CH$_2$Cl$_2$ (10 mL). Benzylamine (0.10 mL, 1.3 mmol) was added dropwise, and the resulting solution was stirred overnight. The solution was then concentrated under reduced pressure. The residue was dissolved in EtOAc (10 mL) and washed with 0.1 M HCl (2×10 mL) and saturated aqueous NaHCO$_3$ (2×10 mL). The organic layer was dried over anhydrous anhydrous Na$_2$SO$_4$(s) and concentrated under reduced pressure to afford S3 (0.255 g, 43%) as a white solid.

Data for S3:
$^1$H NMR (500 MHz, CD$_3$CN, δ): 7.34-7.30 (m, 4H), 7.27-7.23 (m, 3H), 6.97 (d, 2H, J=8.8 Hz), 4.99 (s, 1H), 4.37 (m, 2H), 3.80 (s, 3H). $^{13}$C NMR (125 MHz, CD$_3$CN, δ): 169.4, 161.0, 139.8, 130.2, 129.4, 128.4, 128.2, 128.0, 115.1, 66.6, 55.9, 43.6. HRMS ESI$^+$) m/z calcd for C$_{16}$H$_{16}$N$_4$O$_2$ [M+H]$^+$ 297.1347; found, 297.1346.

Preparation of α-Diazo Amide 1

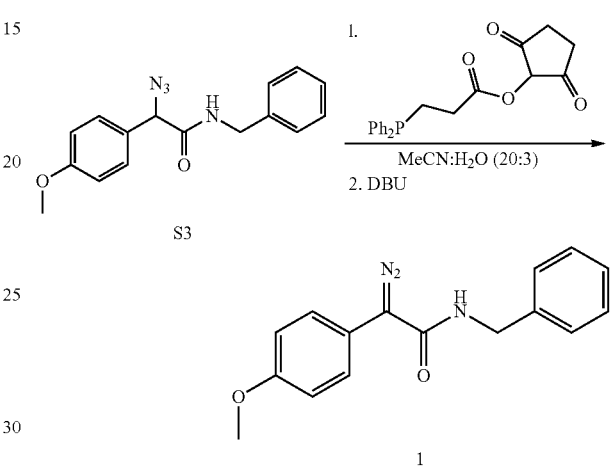

α-Azidoamide S3 (0.356 g, 1.2 mmol) was dissolved in 20:3 MeCN/H$_2$O (12 mL), and the resulting solution was cooled in an ice bath. N-Succinimidyl 3-(diphenylphosphino)propionate (0.440 g, 1.24 mmol) was added slowly. The solution was warmed to ambient temperature and stirred until all azide was consumed (~12 h as monitored by TLC). DBU (0.21 mL, 1.4 mmol) was added, and the solution was stirred for 1 h. The solution was then diluted with brine (10 mL) and extracted with CH$_2$Cl$_2$ (2×20 mL). The organic layer was dried over anhydrous Na$_2$SO$_4$(s) and concentrated under reduced pressure. The residue was purified by chromatography on silica gel, eluting with 1:1 EtOAc/hexanes to afford 1 (0.095 g, 28%) as an orange solid.

Data for 1:
$^1$H NMR (500 MHz, CD$_3$CN, δ): 7.37 (d, 2H, J=8.9 Hz), 7.34-7.29 (m, 4H), 7.26-7.23 (m, 1H), 4.43 (d, 2H, J=6.2 Hz), 3.80 (s, 3H). $^{13}$C NMR (125 MHz, CDCl$_3$, δ): 165.4, 159.7, 138.4, 130.3, 128.7, 127.7, 117.5, 115.3, 63.1, 55.4, 44.1. HRMS (ESI$^+$) m/z calcd for C$_{16}$H$_{15}$N$_3$O$_2$ [M+H]$^+$ 282.1238; found, 282.1232.

Preparation of α-Azido Acid S4

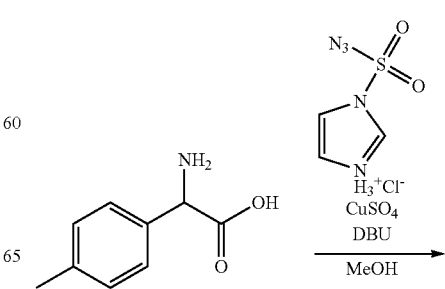

-continued

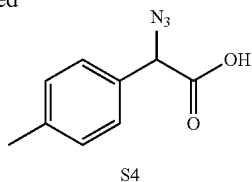

Imidazole-1-sulfonyl-azide hydrochloride was prepared as reported previously. [29] Spectral data and yields match those reported previously. α-Amino-4-methylphenylacetic acid (2.000 g, 12.1 mmol) was dissolved in MeOH (24 mL). DBU (3.61 mL, 24.2 mmol), CuSO$_4$ (0.300 g, 1.2 mmol), and azide (3.030 g, 14.5 mmol) were added sequentially. The resulting solution was heated to 40° C. and stirred overnight. The solution was then concentrated under reduced pressure. The residue was dissolved in EtOAc (30 mL) and washed twice with 1 M aqueous HCl (2×30 mL). The organic layers were combined and dried over anhydrous Na$_2$SO$_4$(s). The solution was concentrated under reduced pressure. The residue was dissolved in benzene and recrystallized from benzene and hexanes to afford S4 (0.390 g, 17%) as a white solid.

Data for S4:
$^1$H NMR (600 MHz, CDCl$_3$, δ): 7.30 (d, 2H, J=8.1 Hz), 7.24 (d, 2H, J=7.8 Hz), 5.01 (s, 1H), 2.37 (s, 3H). $^{13}$C NMR (150 MHz, CDCl$_3$, δ): 173.4, 139.7, 130.2, 129.9, 127.6, 64.9, 21.2. HRMS (ESI$^-$) m/z calcd for C$_9$H$_9$N$_3$O$_2$ [M−H]$^-$ 190.0622; found, 190.0625.

Preparation of α-Azido-Methylphenylacetic Amide S5

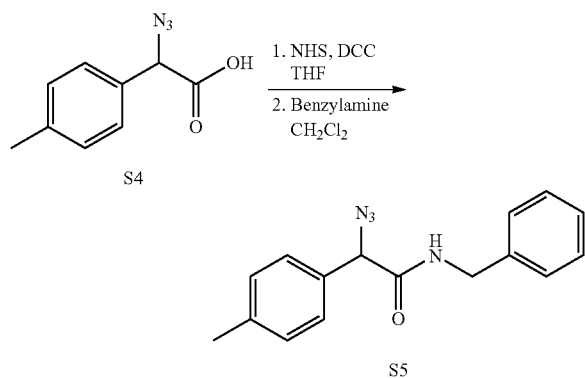

α-Azido 4-methylphenylacetic acid S4 (2.204 g, 11.6 mmol) was dissolved in THF (30 mL) and cooled in an ice bath. N-Hydroxysuccinimide (1.334 g, 11.6 mmol) was added, followed by portion-wise addition of DCC (2.637 g, 12.8 mmol). The resulting solution was warmed to ambient temperature and stirred overnight. The slurry was removed by filtration, and the solution was concentrated under reduced pressure. The residue was dissolved in EtOAc (30 mL). The resulting solution was washed with saturated aqueous NaHCO$_3$ (2×30 mL). The organic layer was dried over anhydrous Na$_2$SO$_4$(s), concentrated under reduced pressure, and used immediately. The NHS ester (2.5 g, 8.7 mmol) was dissolved in CH$_2$Cl$_2$ (30 mL). Benzylamine (0.98 mL, 9.6 mmol) was added dropwise, and the resulting solution was stirred overnight. The solution was then concentrated under reduced pressure. The residue was dissolved in EtOAc (30 mL) and washed with 0.1 M HCl (2×30 mL) and saturated aqueous NaHCO$_3$ (2×30 mL). The organic layer was dried over anhydrous anhydrous Na$_2$SO$_4$(s) and concentrated under reduced pressure to afford S5 (1.988 g, 61%) as a white solid.

Data for S5:
$^1$H NMR (500 MHz, CD$_3$CN, δ): 7.33-7.28 (m, 4H), 7.26-7.22 (m, 5H), 5.00 (s, 1H), 4.36 (dd, 2H, J=1.8, 6.2 Hz), 2.35 (s, 3H). $^{13}$C NMR (125 MHz, CD$_3$CN, δ): 169.2, 140.0, 139.8, 133.5, 130.4, 129.4, 128.8, 128.0, 66.9, 43.6, 21.1. HRMS (ESI$^+$) m/z calcd for C$_{16}$H$_{16}$N$_4$O [M+H]$^+$ 281.1397; found, 281.1395.

Preparation of α-Diazo-Methylphenylacetic Amide 2

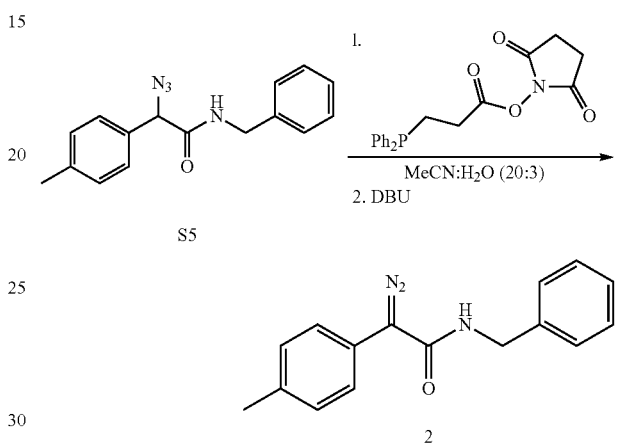

α-Azido 4-methylphenylacetic amide S5 (1.995 g, 7.1 mmol) was dissolved in 20:3 MeCN/H$_2$O (50 mL), and the resulting solution was cooled in an ice bath. N-Succinimidyl 3-(diphenylphosphino)propionate (2.769 g, 7.8 mmol) was added slowly. The solution was warmed to ambient temperature and stirred until all azide was consumed (~24 h as monitored by TLC). DBU (1.27 mL, 8.5 mmol) was added, and the solution stirred for 45 min. The solution was then diluted with brine (10 mL) and extracted with CH$_2$Cl$_2$ (2×30 mL). The organic layer was dried over anhydrous Na$_2$SO$_4$(s) and concentrated under reduced pressure. The residue was purified by chromatography on silica gel, eluting with 4:6 EtOAc/hexanes to afford 2 (1.038 g, 55%) as an orange solid.

Data for 2:
$^1$H NMR (600 MHz, CD$_3$CN, δ): 7.33-7.23 (m, 9H), 6.63 (s, 1H), 4.44 (d, 2H, J=6.2 Hz), 2.34 (s, 3H). $^{13}$C NMR (150 MHz, CD$_3$CN, δ): 165.5, 140.7, 138.1, 130.9, 129.3, 128.2, 128.1, 127.9, 124.1, 63.74, 44.0, 21.1. HRMS (ESI$^+$) m/z calcd for C$_{16}$H$_{15}$N$_3$O [M+H]$^+$ 266.1288; found, 266.1292.

General Procedure for Preparation of Azides S6-S8

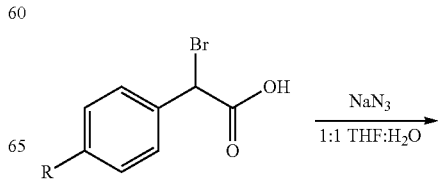

-continued

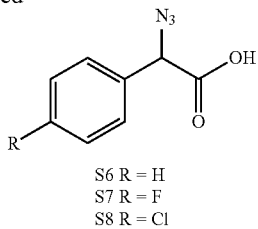

S6 R = H
S7 R = F
S8 R = Cl

Each α-bromophenylacetic acid (23.3 mmol) was dissolved in a solution of 1:1 THF/H$_2$O (24 mL). Sodium azide (1.512 g, 46.5 mmol) was added, and the resulting solution was stirred overnight. The solution was then concentrated under reduced pressure. The residue was dissolved in EtOAc (50 mL), and washed with 0.1 M HCl (2×50 mL). The organic layer was dried over anhydrous Na$_2$SO$_4$(s) and concentrated under reduced pressure to afford a white solid (S6: 4.076 g, 99%; S7: 4.016 g, 89%; S8: 3.761 g, 77%).

Data for Azide S6:
$^1$H NMR (400 MHz, CDCl$_3$, δ): 7.43 (m, 5H), 5.05 (s, 1H). $^{13}$C NMR (400 MHz, CDCl$_3$, δ): 174.0, 133.1, 129.6, 129.2, 127.7, 65.1. HRMS (ESI$^+$) m/z calcd for C$_8$H$_7$N$_3$O$_2$ [M+H]$^+$ 177.0533; found, 177.0538.

Data for Azide S7:
$^1$H NMR (400 MHz, CDCl$_3$, δ): 7.41 (dd, 2H, J=5.1, 8.5 Hz), 7.12 (t, 2H, J=8.4 Hz), 5.05 (s, 1H). $^{13}$C NMR (100 MHz, CDCl$_3$, δ): 175.0, 163.5 (d, J=249.6 Hz), 129.8 (d, J=8.5 Hz) 129.1 (d, J=2.6 Hz), 116.5 (d, J=22.1 Hz), 64.5. HRMS (ESI$^-$) m/z calcd for C$_8$H$_6$FN$_3$O$_2$ [M–H]$^-$ 194.0371; found, 194.0378.

Data for Azide S8:
$^1$H NMR (400 MHz, CDCl$_3$, δ): 7.41 (d, 2H, J=8.4 Hz), 7.37 (d, 2H, J=8.3 Hz), 5.06 (s, 1H). $^{13}$C NMR (125 MHz, CDCl$_3$, δ): 174.7, 135.8, 131.5, 129.5, 129.0, 64.3. HRMS (ESI$^-$) m/z calcd for C$_8$H$_6$ClN$_3$O$_2$ [M–H]$^-$ 210.0075; found, 210.0078.

General Procedure for Preparation of Amides S9-S11

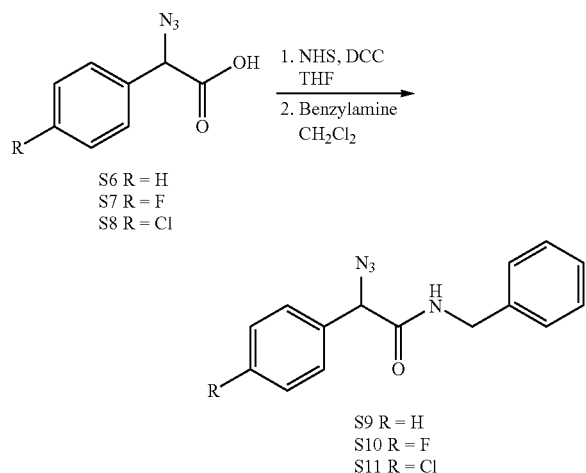

S6 R = H
S7 R = F
S8 R = Cl

S9 R = H
S10 R = F
S11 R = Cl

Each α-azidoacetic acid (S6-S8) (15.4 mmol) was dissolved in THF (30 mL), and the resulting solution was cooled in an ice bath. N-Hydroxysuccinimide (NHS) (1.772 g, 15.4 mmol) was added, followed by portion-wise addition of DCC (3.177 g, 15.4 mmol). The solution was warmed to ambient temperature and stirred overnight. The slurry was removed by filtration, and the solution was concentrated under reduced pressure. The residue was dissolved in EtOAc (50 mL) and washed with saturated aqueous NaHCO$_3$ (2×50 mL). The organic layer was dried over anhydrous Na$_2$SO$_4$(s) and concentrated under reduced pressure. The residue was purified by chromatography on silica gel, eluting with 1:1 EtOAc/hexanes. The resulting solution was then concentrated under reduced pressure and used immediately. The NHS ester (10.5 mmol) was dissolved in CH$_2$Cl$_2$ (105 mL). Benzylamine (1.16 mL, 10.6 mmol) was added drop-wise, and the resulting solution was stirred overnight. The solution was concentrated under reduced pressure. The residue was dissolved in EtOAc (50 mL) and washed with 0.1 M HCl (2×50 mL) and saturated aqueous NaHCO$_3$ (2×50 mL). The organic layer was dried over anhydrous Na$_2$SO$_4$(s) and concentrated under reduced pressure. The residue was purified by chromatography on silica gel, eluting with 30% EtOAc/hexanes to afford a white solid (S9: 2.384 g, 58% for 2 steps; S10: 2.062 g, 47% for 2 steps; S11: 2.179 g, 47% for 2 steps).

Data for Amide S9:
$^1$H NMR (500 MHz, CD$_3$CN, δ): 7.43-7.42 (m, 5H), 7.31-7.29 (m, 2H), 7.26-7.22 (m, 3H), 5.06 (s, 1H), 4.37 (d, 2H, J=6.2). $^{13}$C NMR (125 MHz, CDCl$_3$, δ): 167.8, 137.5, 134.9, 129.2, 129.1, 128.8, 127.8, 127.73, 127.67, 67.4, 43.7. HRMS (ESI$^+$) m/z calcd for C$_{15}$H$_{14}$N$_4$O [M+H]$^+$ 267.1241; found, 267.1241.

Data for Amide S10:
1H NMR (600 MHz, CD3CN, δ): 7.45-7.42 (dd, 2H, J=5.4, 8.7 Hz), 7.23-7.30 (m, 2H), 7.26-7.22 (m, 3H), 7.18-7.15 (m, 2H), 5.08 (s, 1H), 4.37 (dd, 2H, J=3.0, 6.2 Hz). $^{13}$C NMR (100 MHz, CDCl$_3$, δ): 167.6, 163.1 (d, J=249.2 Hz), 137.5, 130.9 (d, J=2.0 Hz), 129.5 (d, J=8.5 Hz), 128.8, 127.8, 116.2 (d, J=21.8 Hz), 105.0, 66.6, 43.7. HRMS (ESI$^+$) m/z calcd for C$_{15}$H$_{13}$FN$_4$O [M+H]$^+$ 285.1147; found, 285.1150.

Data for Amide S11:
$^1$H NMR (500 MHz, CD$_3$CN, δ): 7.44-7.39 (m, 4H), 7.33-7.27 (m, 2H), 7.25-7.22 (m, 3H), 5.08 (s, 1H), 4.36 (m, 2H). $^{13}$C NMR (125 MHz, CD$_3$CN, δ): 168.8, 139.7, 135.5, 135.2, 130.4, 129.9, 129.4, 128.2, 128.0, 66.3, 43.6. HRMS (ESI$^+$) m/z calcd for C$_{15}$H$_{13}$ClN$_4$O [M+H]$^+$ 301.0851; found, 301.0850.

General Procedure for Preparation of Diazo Compounds 3-5

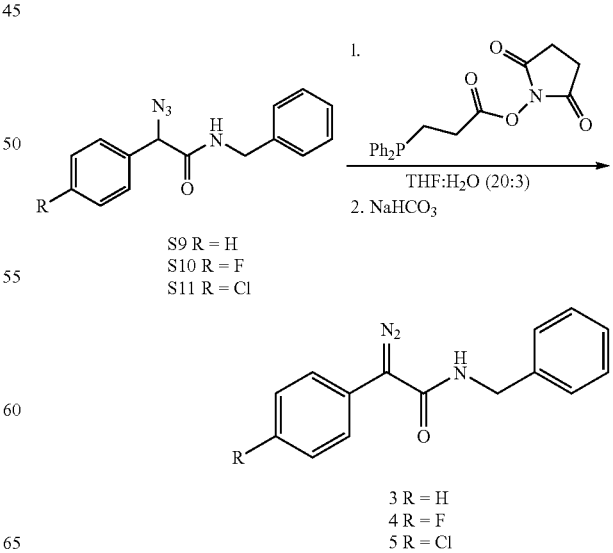

S9 R = H
S10 R = F
S11 R = Cl

3 R = H
4 R = F
5 R = Cl

Each α-azidobenzylamide (S9-S11) (7.3 mmol) was dissolved in a solution of 20:3 THF:H₂O (75 mL) and cooled in an ice bath. N-Succinimidyl 3-(diphenylphosphino)propionate (2.734 g, 7.7 mmol) was added slowly. The resulting solution was warmed to ambient temperature and stirred until all azide was consumed (6-12 h as monitored by TLC). Saturated aqueous NaHCO₃ (73 mL) was added, and the solution was stirred overnight. The solution was then diluted with brine (50 mL) and extracted with CH₂Cl₂ (2×70 mL). The organic layer was dried over anhydrous Na₂SO₄(s) and concentrated under reduced pressure. The residue was purified by chromatography on silica gel, eluting with 1:1 EtOAc/hexanes to afford an orange solid (3: 1.012 g, 55%; 4: 0.887 g, 45%; 5: 0.877 g, 42%).

Data for Diazo 3:
$^1$H NMR (600 MHz, CD₃CN, δ): 7.46-7.41 (m, 4H), 7.34-7.28 (m, 4H), 7.28-7.23 (m, 2H), 6.73 (s, 1H), 4.44 (d, 2H, J=6.1 Hz). $^{13}$C NMR (125 MHz, CD₃CN, δ): 165.1, 140.6, 130.2, 129.3, 128.2, 127.8, 127.7, 127.6, 127.4, 64.0, 43.9. HRMS (ESI⁺) m/z calcd for C₁₅H₁₃N₃O [M+H]⁺ 252.1132; found, 252.1125.

Data for Diazo 4:
$^1$H NMR (500 MHz, CD₃CN, δ): 7.49-7.46 (dd, 2H, J=5.4, 8.6 Hz), 7.34-7.29 (m, 4H), 7.26-7.23 (m, 1H), 7.20-7.16 (t, 2H, J=8.8), 6.70 (s, 1H), 4.43 (d, 2H, J=6.2). $^{13}$C NMR (125 MHz, CD₃CN, δ): 165.2, 162.5 (d, J=244.9 Hz), 140.6, 130.2, (d, J=8.3 Hz), 129.2, 128.1, 127.8, 123.4 (d, J=3.1 Hz), 116.9 (d, J=22.1 Hz), 62.99, 43.8. HRMS (ESI⁺) m/z calcd for C₁₅H₁₂FN₃O [M+H]⁺ 270.1038; found, 270.1032.

Data for Diazo 5:
$^1$H NMR (500 MHz, CD₃CN, δ): 7.45 (d, 2H, J=8.8 Hz), 7.42 (d, 2H, 8.9 Hz), 7.35-7.30 (m, 4H), 7.28-7.26 (m, 1H), 6.79 (s, 1H), 4.44 (d, 2H, J=6.1 Hz). $^{13}$C NMR (125 MHz, CDCl₃, δ): 164.1, 138.1, 133.5, 129.9, 128.8, 128.5, 127.8, 127.7, 124.7, 63.5, 44.2. HRMS (ESI⁺) m/z calcd for C₁₅H₁₂ClN₃O [M+H]⁺ 286.0742; found, 286.0748.

Preparation of Ester S12

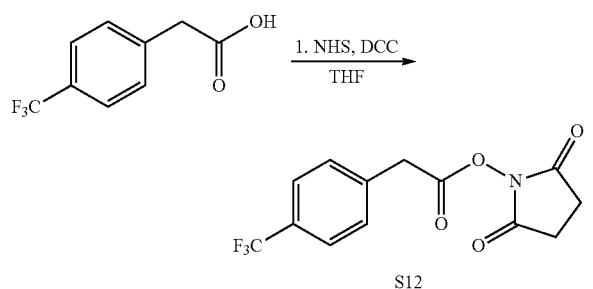

4-(Trifluoromethyl)phenylacetic acid (5.000 g, 24.5 mmol) was dissolved in THF (50 mL), and the resulting solution was cooled in an ice bath. N-Hydroxysuccinimide (2.818 g, 24.5 mmol) was added, followed by DCC (5.047 g, 24.5 mmol). The solution was warmed to ambient temperature and stirred overnight. The slurry was removed by filtration, and the solution was concentrated under reduced pressure. The residue was dissolved in EtOAc (50 mL) and washed with saturated aqueous NaHCO₃ (2×50 mL). The organic layer was dried over anhydrous Na₂SO₄(s) and concentrated under reduced pressure. The residue was purified by chromatography on silica gel, eluting with 1:1 EtOAc/hexanes to afford S12 (7.301 g, 99%) as a white solid.

Data for Ester S12:
$^1$H NMR (400 MHz, CDCl₃, δ): 7.63 (d, 2H, J=7.99 Hz), 7.48 (d, 2H, J=7.92 Hz), 4.00 (s, 2H), 2.84 (s, 4H). $^{13}$C NMR (125 MHz, CDCl₃, δ): 168.9, 166.1, 135.27, 130.2 (q, J=32.6 Hz), 129.7, 125.8 (q, J=3.7 Hz), 123.9 (q, J=272.1 Hz), 37.4, 25.6. HRMS (EI⁺) m/z calcd for C₁₃H₁₀F₃NO₄ [M+H]⁺ 301.0557; found, 301.0565.

Preparation of α-Bromoester S13

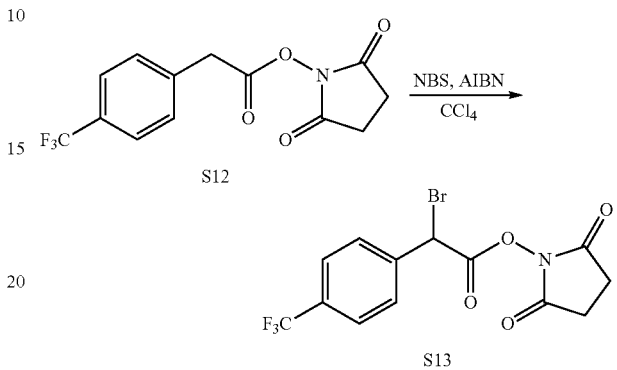

Ester S12 (3.763 g, 12.5 mmol) was dissolved in CCl₄ (25 mL). N-Bromosuccinimide (3.329 g, 18.7 mmol) and AIBN (0.394 g, 2.4 mmol) were added. The resulting solution was heated to 80° C. and allowed to reflux overnight. The succinimide by-product was removed by filtration, and solution was concentrated under reduced pressure. The residue was purified by chromatography on silica gel, eluting with 1:1 EtOAc/hexanes to afford S13 (2.037 g, 43%) as a white solid.

Data for S13:
$^1$H NMR (500 MHz, CDCl₃, δ): 7.72 (d, 2H, J=8.3 Hz), 7.69 (d, 2H, J=8.6 Hz), 5.68 (s, 1H), 2.86 (s, 4H). $^{13}$C NMR (125 MHz, CDCl₃, δ): 168.2, 163.8, 137.7, 131.9 (q, J=32.8 Hz), 129.2, 126.1 (q, J=3.7 Hz), 123.6 (q, J=272.5 Hz), 40.7, 25.6. HRMS (EI¹ m/z calcd for C₁₃H₉BrF₃NO₄ [M+H]⁺ 378.9662; found, 378.9667.

Preparation of α-Bromoamide S14

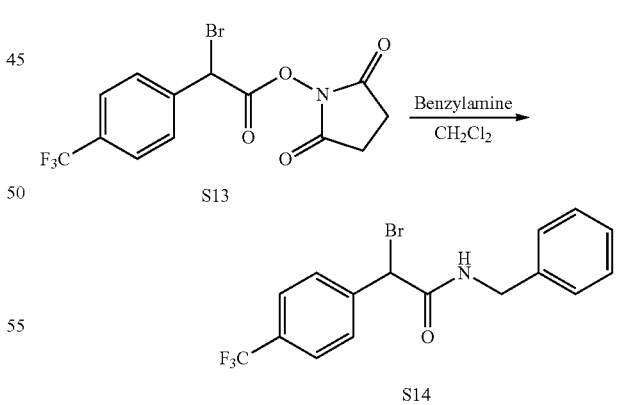

α-Bromoester S13 (3.297 g, 8.7 mmol) was dissolved in CH₂Cl₂ (80 mL). Benzylamine (0.91 mL, 8.7 mmol) was added drop-wise, and the resulting solution was stirred overnight. The solution was concentrated under reduced pressure, and the residue was dissolved in EtOAc (50 mL). The solution was washed with 0.1 M HCl (2×50 mL) and saturated aqueous NaHCO₃ (2×50 mL). The organic layers were dried over anhydrous Na₂SO₄(s) and concentrated under reduced pressure. The residue was purified with chromatography on silica gel, eluting with 1:1 EtOAc/hexanes to afford S14 (1.456 g, 45%) as a white solid.

Data for S14:

$^1$H NMR (500 MHz, CD$_3$CN, δ): 7.76 (d, 2H, J=8.3 Hz), 7.72 (d, 2H, J=2H), 7.51 (s, 1H), 7.35 (t, 3H, J=7.4 Hz), 7.29 (t, 3H, J=7.7 Hz), 5.59 (s, 1H), 4.40 (m, 2H). $^{13}$C NMR (125 MHz, CDCl$_3$, δ): 166.2, 141.2, 137.1, 131.1 (q, J=32.8 Hz), 128.9, 128.8, 128.0, 127.8, 125.9 (q, J=3.7 Hz), 123.7 (q, J=272.3 Hz), 49.8, 44.6. HRMS (ESI$^+$) m/z calcd for C$_{16}$H$_{13}$BrF$_3$NO [M+H]$^+$ 372.0206; found, 372.0210.

Preparation of α-Azidoamide S15

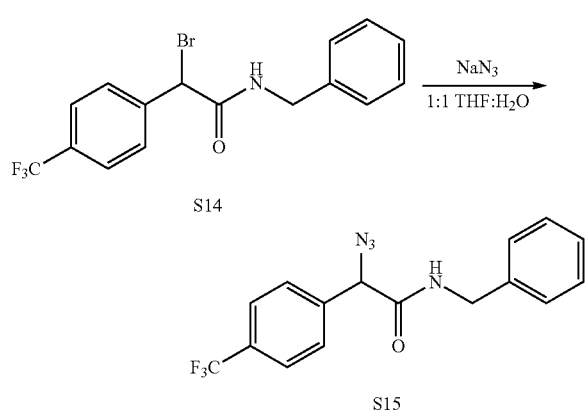

α-Bromoamide S14 (1.823 g, 4.9 mmol) was dissolved in 1:1 THF/H$_2$O. Sodium azide (0.637 g, 9.8 mmol) was added, and the resulting solution was stirred overnight. The solution was concentrated under reduced pressure. The residue was dissolved in EtOAc (50 mL), and the resulting solution was washed twice with 0.1 M HCl (2×50 mL). The organic layer was dried over anhydrous Na$_2$SO$_4$(s) and concentrated under reduced pressure to afford S15 (1.018 g, 62%) as a white solid.

Data for S15: $^1$H NMR (500 MHz, CD$_3$CN, δ): 7.74 (d, 2H, J=8.1 Hz), 7.60 (d, 2H, J=8.0 Hz), 7.42 (s, 1H), 7.31 (m, 2H), 7.24 (m, 3H), 5.19 (s, 1H), 4.37 (d, 2H, J=6.2 Hz). $^{13}$C NMR (125 MHz, CD$_3$CN, δ): 170.2, 142.8, 141.4, 132.9 (q, J=32.3 Hz), 131.2, 131.1, 130.0, 129.8, 128.5 (q, J=3.9 Hz), 126.9 (q, J=271.3 Hz), 68.2, 45.4. HRMS (ESI$^+$) m/z calcd for (C$_{16}$H$_{13}$F$_3$N$_4$O) [M+H]$^+$ 335.1115; found, 335.1112.

Preparation of α-Diazoamide 6

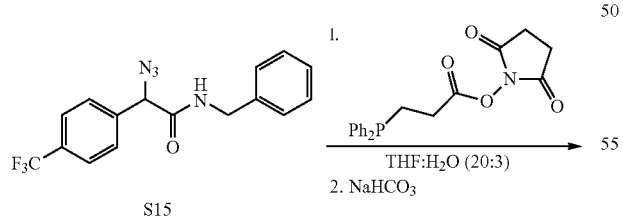

α-Azidoamide S15 (1.002 g, 2.99 mmol) was dissolved in 20:3 THF/H$_2$O (30 mL), and the resulting solution was cooled in an ice bath. N-Succinimidyl 3-(diphenylphosphino)propionate (1.115 g, 3.14 mmol) was added slowly. The solution was warmed to ambient temperature and stirred until all azide was consumed (~5 h as monitored by TLC). Saturated aqueous NaHCO$_3$ (30 mL) was added, and the solution was stirred overnight. The solution was diluted with brine (30 mL) and extracted with CH$_2$Cl$_2$ (2×30 mL). The organic layer was dried over anhydrous Na$_2$SO$_4$(s) and concentrated under reduced pressure. The residue was purified by chromatography on silica gel, eluting with 1:1 EtOAc/hexanes to afford 6 (0.382 g, 40%) as an orange solid.

Data for 6:

$^1$H NMR (400 MHz, CDCl$_3$, δ): 7.65 (d, 2H, J=8.0 Hz), 7.50 (d, 2H, J=8.1 Hz), 7.38-7.31 (m, 5H), 5.70 (s, 1H), 4.59 (d, 2H, J=4.6 Hz). $^{13}$C NMR (125 MHz, CD$_3$CN, δ): 164.2, 140.4, 132.9, 128.3, 127.9, 127.6 (q, J=32.4 Hz), 126.5 (q, J=3.9 Hz), 126.3, 125.3 (q, J=270.8 Hz), 64.0, 43.9. HRMS (ESI$^+$) m/z calcd for C$_{16}$H$_{12}$F$_3$N$_3$O [M+H]$^+$ 320.1006; found, 320.0993.

Example 3: Measurement of Reaction Rate Constants

Each diazo compound and BocGlyOH were dissolved separately in CD$_3$CN at a concentration of 50 mM. The solutions were combined in an NMR tube at an equimolar ratio, mixed, and then inserted immediately into an NMR spectrometer. A 16-scan $^1$H NMR spectrum was acquired every 10 min. Percent conversion was monitored by disappearance of starting material and appearance of product as determined by integration of multiple $^1$H NMR spectral peaks. No other products were apparent by $^1$H NMR spectroscopy. The value of the second-order rate constant was determined by linear regression analysis of a plot of 1/[diazo] versus time (data not shown). All reactions were performed in triplicate.

Example 4: Esterification of BocGlyOH

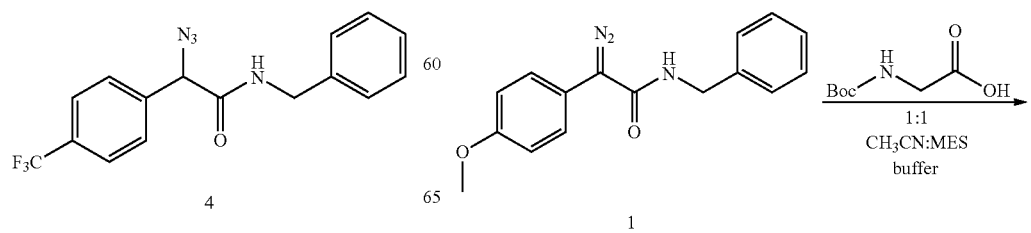

-continued

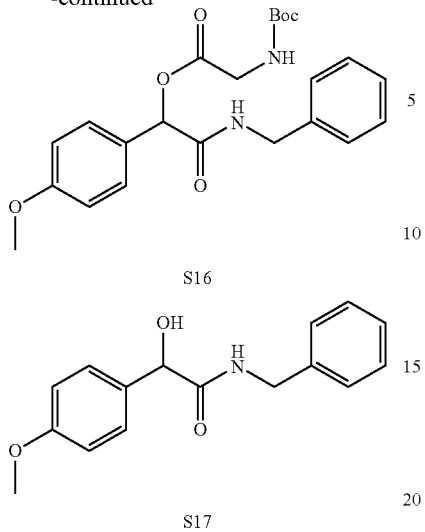

S16

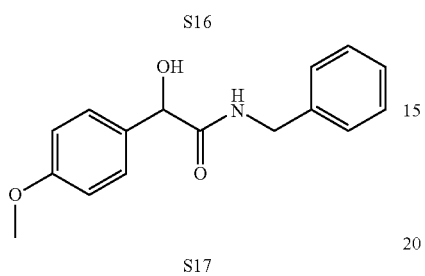

S17

-continued

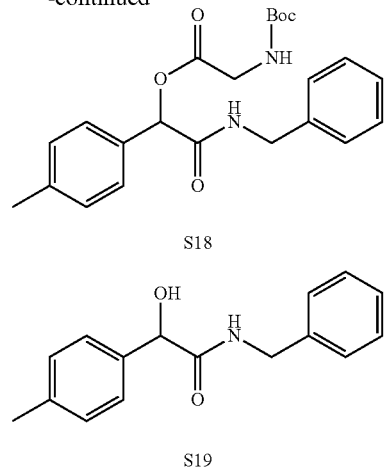

S18

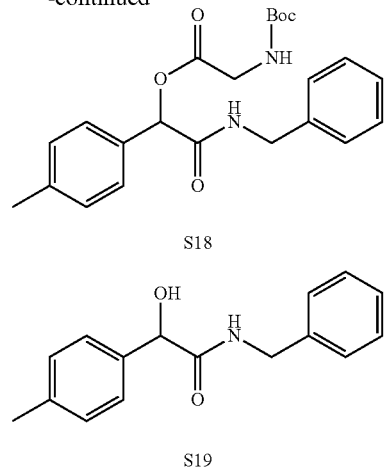

S19

Diazo compound 1 (0.005 g, 0.02 mmol) and BocGlyOH (0.003 g, 0.02 mmol) were added to a 1:1 solution of acetonitrile/100 mM MES-HCl buffer at pH 5.5, and the resulting solution was stirred for 6 h at ambient temperature. The reaction mixture was concentrated under reduced pressure, and the ratio of products was determined by integration of $^1$H NMR spectral peaks.

Data for S16:

$^1$H NMR (400 MHz, CD$_3$CN, δ): 7.60 (s, 1H), 7.37-7.22 (m, 7H), 6.93 (d, 2H, J=8.4 Hz), 5.91 (s, 1H), 5.74 (s, 1H), 4.43-4.31 (m, 2H), 3.94-3.82 (m, 2H), 3.79 (s, 3H), 1.38 (s, 9H). $^{13}$C NMR (100 MHz, CD$_3$CN, δ): 170.4, 169.3, 161.1, 157.4, 139.9, 129.9, 129.3, 128.6, 128.1, 127.9, 114.8, 80.3, 76.7, 55.9, 43.2, 28.4 HRMS (ESI$^+$) m/z calcd for C$_{23}$H$_{28}$N$_2$O$_6$ [M+H]$^+$ 429.2021; found, 429.2021.

Data for S17:

$^1$H NMR (500 MHz, CD$_3$CN, δ): 7.47 (s, 1H), 7.33-7.25 (m, 4H), 7.23-7.21 (m, 3H), 6.90 (d, 2H, J=8.8 Hz), 4.97 (d, 1H, J=4.5 Hz), 4.40-4.32 (m, 2H), 4.16 (d, 2H, J=4.5 Hz), 3.78 (s, 3H). $^{13}$C NMR (125 MHz, CD$_3$CN, δ): 173.3, 160.4, 140.3, 133.8, 129.3, 129.0, 128.1, 127.8, 114.5, 74.3, 55.8, 43.1. HRMS (ESI$^+$) m/z calcd for C$_{16}$H$_{17}$NO$_3$ [M+H]$^+$ 272.1282; found, 272.1278.

Diazo compound 2 (0.005 g, 0.02 mmol) and BocGlyOH (0.003 g, 0.02 mmol) were added to 1:1 acetonitrile/100 mM MES-HCl buffer at pH 5.5, and the resulting solution was stirred for 6 h at ambient temperature. The solution was then concentrated under reduced pressure, and the ratio of products was determined by integration of $^1$H NMR spectral peaks.

Data for S18:

$^1$H NMR (500 MHz, CD$_3$CN, δ): 7.65 (s, 1H), 7.33-7.28 (m, 4H), 7.25-7.20 (m, 5H), 5.92 (s, 1H), 5.77 (s, 1H), 4.42-4.31 (m, 2H), 3.92-3.82 (m, 2H), 2.34 (s, 3H), 1.38 (s, 9H). $^{13}$C NMR (125 MHz, CD$_3$CN, δ): 170.4, 169.2, 157.4, 140.0, 139.8, 133.7, 130.1, 129.3, 128.3, 128.1, 127.9, 80.3, 76.8, 43.2, 43.2, 28.4, 21.2. HRMS (ESI$^+$) m/z calcd for C$_{23}$H$_{28}$N$_2$O$_5$ [M+NH$_4$]$^+$ 430.2337; found, 430.2336.

Data for S19:

$^1$H NMR (500 MHz, CD$_3$CN, δ): 7.46 (s, 1H), 7.31-7.28 (m, 4H), 7.25-7.21 (m, 3H), 7.17 (d, 2H, J=7.9 Hz), 4.99 (d, 1H, J=4.2 Hz), 4.40-4.32 (m, 2H), 4.18 (d, 1H, J=4.5 Hz), 2.32 (s, 1H). $^{13}$C NMR (125 MHz, CD$_3$CN, δ): 173.3, 140.3, 138.74, 138.71, 129.8, 129.3, 128.1, 127.9, 127.6, 74.6, 43.1, 21.1. HRMS (ESI$^+$) m/z calcd for C$_{16}$H$_{17}$NO$_2$ [M+H]$^+$ 256.1333; found, 256.1330.

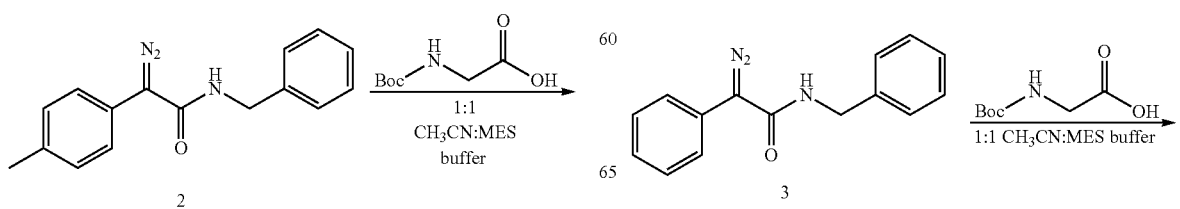

-continued

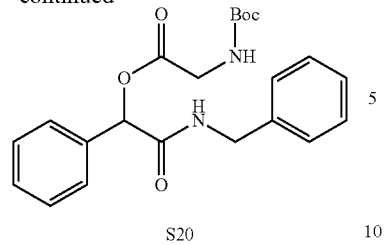

S20

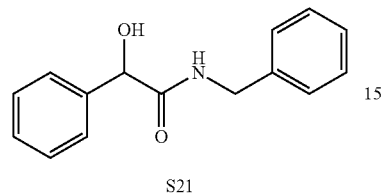

S21

Diazo compound 3 (0.005 g, 0.02 mmol) and BocGlyOH (0.004 g, 0.02 mmol) were added to 1:1 acetonitrile/100 mM MES-HCl buffer at pH 5.5, and the resulting solution was stirred for 6 h at ambient temperature. The reaction mixture was then concentrated under reduced pressure, and the ratio of products was determined by integration of $^1$H NMR spectral peaks.

Data for S20:

$^1$H NMR (750 MHz, CD$_3$CN, δ): 7.65 (s, 1H), 7.46 (m, 2H), 7.40 (m, 3H), 7.30 (t, 2H, J=7.4 Hz), 7.23 (m, 3H), 5.99 (s, 1H), 5.78 (s, 1H), 4.41 (dd, 1H, J=6.3, 15.2 Hz), 4.35 (dd, 1H, J=6.1, 15.2 Hz), 3.92 (dd, 1H, J=6.2, 17.9 Hz), 3.88 (dd, 1H, J=5.7, 18.0 Hz), 1.40 (s, 9H). $^{13}$C NMR (125 MHz, CDCl$_3$, δ): 168.7, 168.0, 156.4, 137.9, 135.0, 129.1, 128.8, 128.6, 127.8, 127.5, 127.4, 80.6, 76.2, 43.4, 43.0, 28.2. HRMS (ESI$^+$) m/z calcd for C$_{22}$H$_{26}$N$_2$O$_5$ [M+H]$^+$ 399.1915; found, 399.1917.

Data for S21:

$^1$H NMR (750 MHz, CD$_3$CN, δ): 7.48 (s, 1H), 7.43 (d, 2H, J=7.4 Hz), 7.36 (t, 2H, J=7.4 Hz), 7.31 (m, 3H), 7.24 (m, 3H), 5.04 (d, 1H, J=2.8 Hz), 4.37 (m, 2H), 4.28 (d, 1H, J=3.8 Hz). $^{13}$C NMR (125 MHz, CD$_3$CN, δ): 173.1, 141.6, 140.3, 129.3, 129.2, 128.8, 128.1, 127.9, 127.6, 74.7, 43.1. HRMS (ESI$^+$) m/z calcd for C$_{15}$H$_{15}$NO$_2$ [M+H]$^+$ 242.1176; found, 242.1169.

-continued

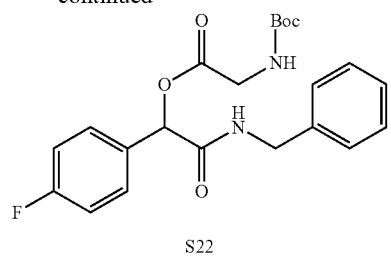

S22

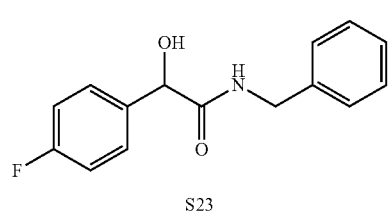

S23

Diazo 4 (0.005 g, 0.02 mmol) and BocGlyOH (0.003 g, 0.02 mmol) were added to 1:1 acetonitrile/100 mM MES-HCl buffer at pH 5.5, and the resulting solution was stirred for 6 h at ambient temperature. The reaction mixture was then concentrated under reduced pressure, and the ratio of products was determined by integration of $^1$H NMR spectral peaks.

Data for S22:

$^1$H NMR (500 MHz, CD$_3$CN, δ): ☐7.66 (s, 1H), 7.48 (dd, 2H, J=5.4, 8.6 Hz), 7.30 (t, 2H, J=7.3 Hz), 7.25-7.20 (m, 3H), 7.14 (t, 2H, J=8.9 Hz), 5.97 (s, 1H), 5.77 (s, 1H), 4.40 (dd, 1H, J=6.3, 15.2 Hz), 4.34 (dd, 1H, J=6.1, 15.2 Hz), 3.94-3.84 (m, 2H), 1.38 (s, 9H). $^{13}$C NMR (125 MHz, CDCl$_3$, δ): 168.6, 167.9, 163.1 (d, J=248.2 Hz), 156.4, 137.8, 131.0 (d, J=3.3 Hz), 129.4 (d, J=8.5 Hz), 127.8, 127.5, 115.8 (d, J=21.8 Hz), 80.7, 75.5, 43.4, 43.0, 28.2. HRMS (ESI$^+$) m/z calcd for C$_{22}$H$_{25}$FN$_2$O$_5$ [M+H]$^+$ 417.1821; found, 417.1816.

Data for S23:

$^1$H NMR (400 MHz, CD$_3$CN, δ): 7.53 (s, 1H), 7.45-7.42 (m, 2H), 7.32-7.28 (m, 2H), 7.24-7.20 (m, 3H), 7.09 (t, 2H, J=8.9 Hz), 5.04 (s, 1H), 4.41-4.31 (m, 2H). $^{13}$C NMR (125 MHz, CD$_3$CN, δ): 174.7, 165.0 (d, J=243.7 Hz), 142.0, 139.6, 131.3 (d, J=8.3 Hz), 131.1, 129.8, 129.6, 117.6 (d, J=21.7 Hz), 75.7, 44.8. HRMS (ESI$^+$) m/z calcd for C$_{15}$H$_{14}$FNO$_2$ [M+H]$^+$ 260.1082; found, 260.1080.

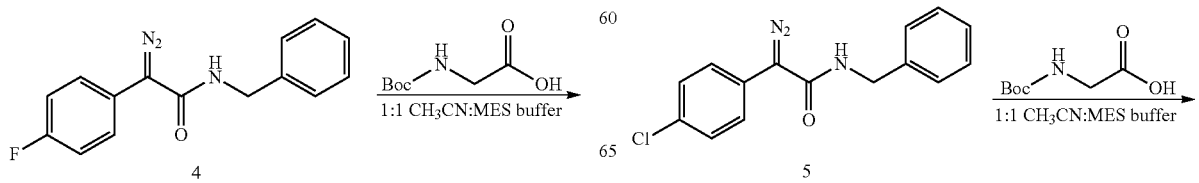

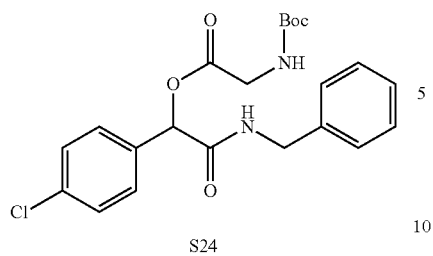

S24

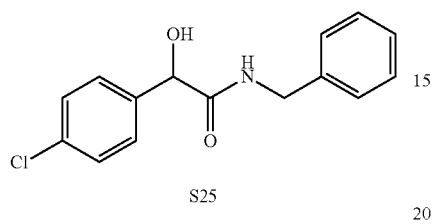

S25

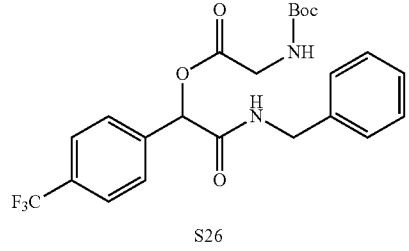

S26

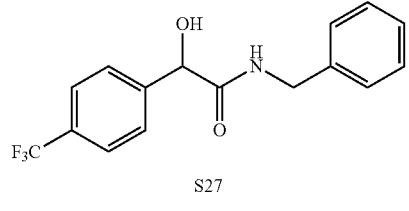

S27

Diazo 5 (0.005 g, 0.02 mmol) and BocGlyOH (0.003 g, 0.02 mmol) were added to 1:1 acetonitrile/100 mM MES-HCl buffer at pH 5.5, and the resulting solution was stirred for 6 h at ambient temperature. The reaction mixture was then concentrated under reduced pressure, and the ratio of products was determined by integration of $^1$H NMR spectral peaks.

Data for S24:

$^1$H NMR (500 MHz, CD$_3$CN, δ): 7.61 (s, 1H), 7.45-7.40 (m, 4H), 7.31-7.29 (m, 2H), 7.25-7.21 (m, 3H), 5.98 (s, 1H), 5.74 (s, 1H), 4.42-4.32 (m, 2H), 3.90 (m, 2H), 1.39 (s, 9H). $^{13}$C NMR (125 MHz, CDCl$_3$, δ): 168.5, 167.6, 156.4, 137.7, 135.1, 135.6, 128.9, 128.8, 128.6, 127.8, 127.5, 80.8, 75.4, 43.4, 43.0, 28.2. HRMS (ESI$^+$) m/z calcd for C$_{22}$H$_{25}$ClN$_2$O$_5$ [M+NH$_4$]$^+$ 450.1791; found, 450.1785.

Data for S25:

$^1$H NMR (500 MHz, CD$_3$CN, δ): 7.47 (s, 1H), 7.42 (d, 2H, J=8.5 Hz), 7.37 (d, 2H, 8.6 Hz), 7.32-7.29 (m, 2H), 7.25-7.21 (m, 3H), 5.04 (d, 1H, J=1.8 Hz), 4.36 (m, 2H), 4.31 (d, 1H, J=3.4 Hz). $^{13}$C NMR (125 MHz, CD$_3$CN, δ): 172.7, 140.5, 140.2, 134.0, 129.3, 129.21, 129.18, 128.1, 127.9, 73.9, 43.1. HRMS (ESI$^+$) m/z calcd for C$_{15}$H$_{14}$ClNO$_2$ [M+H]$^+$ 276.0786; found, 276.0789.

Diazo 6 (0.005 g, 0.02 mmol) and BocGlyOH (0.003 g, 0.02 mmol) were added to 1:1 acetonitrile/100 mM MES-HCl buffer at pH 5.5, and the resulting solution was stirred for 6 h at ambient temperature. The reaction mixture was then concentrated under reduced pressure, and the ratio of products was determined by integration of $^1$H NMR spectral peaks.

Data for S26:

$^1$H NMR (500 MHz, CD$_3$CN, δ): 7.73-7.71 (m, 3H), 7.65 (d, 2H, J=8.3 Hz), 7.31-7.28 (m, 2H), 7.25-7.20 (m, 3H), 6.06 (s, 1H), 5.77 (s, 1H), 4.42-4.32 (m, 2H), 3.97-3.87 (m, 2H), 1.38 (s, 1H). $^{13}$C NMR (125 MHz, CD$_3$CN, δ): 170.3, 168.4, 157.4, 141.1, 139.7, 131.1 (q, J=32.4 Hz), 129.4, 128.8, 128.1, 128.0, 126.3 (q, J=3.9 Hz), 125.1 (q, J=271.3 Hz), 80.4, 76.1, 43.4, 43.2, 28.4. HRMS (ESI$^+$) m/z calcd for C$_{23}$H$_{25}$F$_3$N$_2$O$_5$ [M+NH$_4$]$^+$ 484.2037; found, 484.2054.

Data for S27:

$^1$H NMR (400 MHz, CD$_3$CN, δ): 7.69-7.62 (m, 4H), 7.56 (s, 1H), 7.31-7.20 (m, 5H), 5.54 (s, 1H), 5.14 (d, 1H, J=4.6 Hz), 4.45 (d, 1H, J=4.8 Hz), 4.37-4.35 (m, 2H). $^{13}$C NMR (125 MHz, CD$_3$CN, δ): 172.3, 146.0, 140.1, 130.1 (q, J=32.3 Hz), 129.3, 128.1, 128.9, 126.2 (q, J=41.3 Hz), 125.3 (q, J=271.3 Hz), 74.0, 43.1. HRMS calcd for (C$_{16}$H$_{14}$F$_3$NO$_2$) [M+H]$^+$ 310.1050; found, 310.1043.

Example 5: Esterification of Other Small Molecules

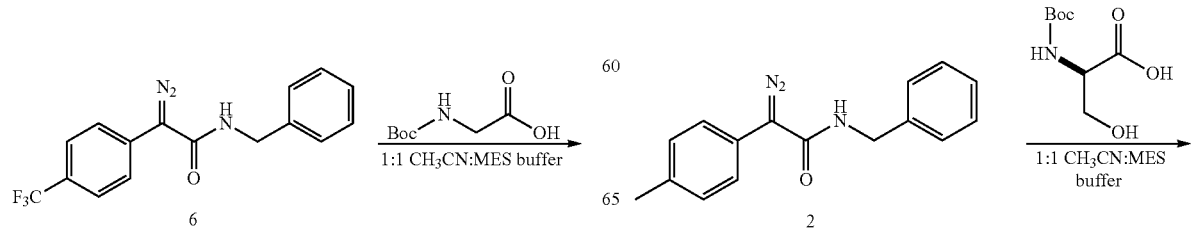

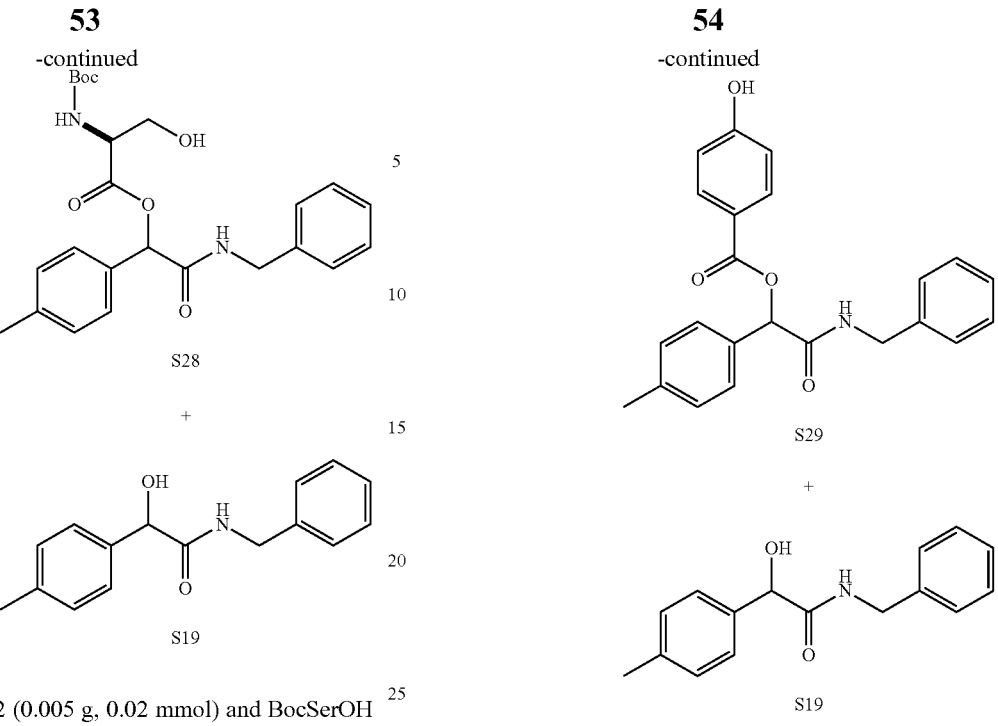

Diazo compound 2 (0.005 g, 0.02 mmol) and BocSerOH (0.004 g, 0.02 mmol) were added to 1:1 acetonitrile/100 mM MES-HCl buffer at pH 5.5, and the resulting solution was stirred for 6 h at ambient temperature. The solution was then concentrated under reduced pressure, and the ratio of products was determined by integration of $^1$H NMR spectral peaks. Data for S19 are reported above; data for S28 are reported below (both diastereomers). No other products were observed by TLC or $^1$H NMR spectroscopy.

Data for S28:

$^1$H NMR (500 MHz, CD$_3$CN, Diastereomer A, δ): 7.72 (s, 1H), 7.35 (d, 2H, J=8.0 Hz), 7.30 (t, 2H, J=7.3 Hz), 7.24 (t, 3H, J=7.7 Hz), 7.18 (d, 2H, J=7.2 Hz), 5.96 (s, 1H), 5.79 (d, 1H, J=6.8 Hz), 4.38-4.33 (m, 2H), 4.32-4.29 (m, 1H), 4.08-4.03 (m, 1H), 3.77-3.69 (m, 2H), 2.34 (s, 3H), 1.40 (s, 9H). $^1$H NMR (500 MHz, CD$_3$CN, Diastereomer B, δ): 7.64 (s, 1H), 7.36-7.28 (m, 4H), 7.25-7.17 (m, 5H), 5.95 (s, 1H), 5.84 (d, 1H, J=7.8 Hz), 4.41-4.30 (m, 2H), 4.28-4.25 (m, 1H), 3.86-3.82 (m, 1H), 3.79-3.72 (m, 1H), 3.41 (t, 3H, J=5.7 Hz), 2.34 (s, 3H), 1.36 (s, 9H). $^{13}$C NMR (125 MHz, CD$_3$CN, Diasteromer A, δ): 171.3, 169.7, 157.0, 140.2, 139.6, 133.2, 130.2, 129.3, 128.5, 128.1, 128.0, 80.3, 77.0, 63.3, 57.1, 43.4, 28.4, 21.2. $^{13}$C NMR (125 MHz, CD$_3$CN, Diastereomer B, δ): 171.2, 169.3, 156.7, 139.9, 139.8, 133.6, 130.1, 129.3, 128.4, 128.1, 127.9, 80.3, 77.0, 62.8, 57.1, 43.3, 28.4, 21.1. HRMS (ESI$^+$) m/z calcd for C$_{24}$H$_{30}$N$_2$O$_6$ [M+H]$^+$ 443.2177; found, 443.2185 (Diastereomer A), 443.2183 (Diastereomer B).

Diazo compound 2 (0.005 g, 0.02 mmol) and p-hydroxybenzoic acid (0.003 g, 0.02 mmol) were added to 1:1 acetonitrile/100 mM MES-HCl buffer at pH 5.5, and the resulting solution was stirred for 6 h at ambient temperature. The solution was then concentrated under reduced pressure, and the ratio of products was determined by integration of $^1$H NMR spectral peaks. Data for S19 are reported above; data for S29 are reported below. No other products were observed by TLC or $^1$H NMR spectroscopy.

Data for S29:

$^1$H NMR (500 MHz, CD$_3$CN, δ): 7.98 (d, 2H, J=8.8 Hz), 7.76 (s, 1H), 7.44 (d, 2H, J=8.1 Hz), 7.39 (s, 1H), 7.29-7.18 (m, 7H), 6.89 (d, 2H, J=8.8 Hz), 6.06 (s, 1H), 4.36 (d, 2H, J=6.2 Hz), 2.35 (s, 3H). $^{13}$C NMR (125 MHz, CD$_3$CN, δ): 169.7, 165.8, 162.6, 140.0, 139.8, 134.2, 133.0, 130.1, 129.3, 128.3, 128.0, 127.9, 121.9, 116.1, 76.8, 43.1, 21.2. HRMS (ESI$^+$) m/z calcd for C$_{23}$H$_{21}$NO$_4$ [M+H]$^+$ 376.1544; found, 376.1539.

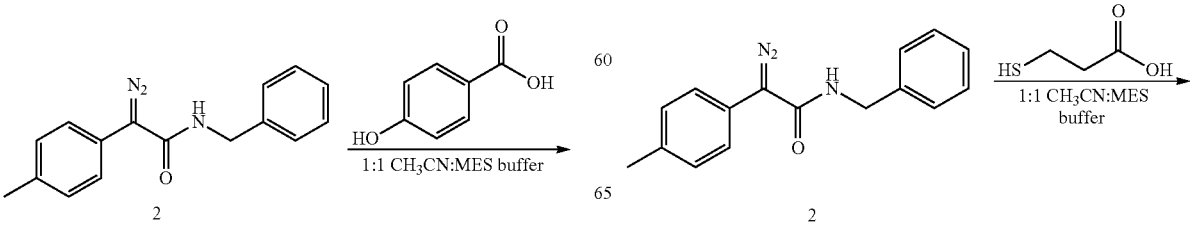

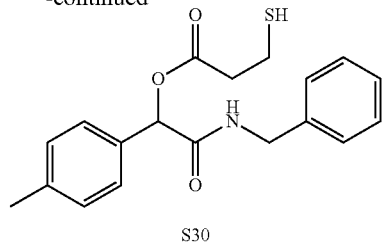

S30

+

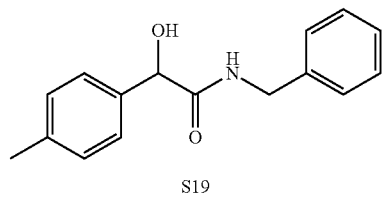

S19

Diazo compound 2 (0.005 g, 0.02 mmol) and 3-mercaptopropanoic acid (0.002 g, 0.02 mmol) were added to 1:1 acetonitrile/100 mM MES-HCl buffer at pH 5.5, and the resulting solution was stirred for 6 h at ambient temperature. The solution was then concentrated under reduced pressure, and the ratio of products was determined by integration of $^1$H NMR spectral peaks. Data for S19 are reported above; data for S30 are reported below. No other products were observed by TLC or $^1$H NMR spectroscopy.

Data for S30:
$^1$H NMR (500 MHz, CD$_3$CN, δ): 7.38 (s, 1H), 7.34 (d, 2H, J=8.1 Hz), 7.29 (t, 2H, J=7.3 Hz), 7.25-7.19 (m, 5H), 5.91 (s, 1H), 4.35 (d, 2H, J=6.2 Hz), 2.80-2.70 (m, 4H), 2.34 (s, 3H), 1.89 (t, 1H, J=8.2 Hz). $^{13}$C NMR (125 MHz, CD$_3$CN, δ): 171.5, 169.4, 139.9, 139.8, 133.9, 130.1, 129.3, 128.3, 128.1, 127.9, 76.6, 43.1, 39.1, 21.1, 20.2. HRMS (ESI$^+$) m/z calcd for (C$_{19}$H$_{21}$NO$_3$S) [M+H]$^+$ 344.1315; found, 344.1315.

Example 6: Protein Labeling

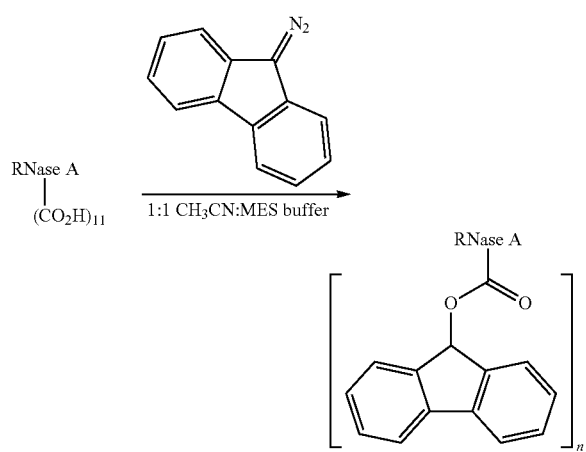

where n indicates the number of esters formed in the protein.

Figure 5:
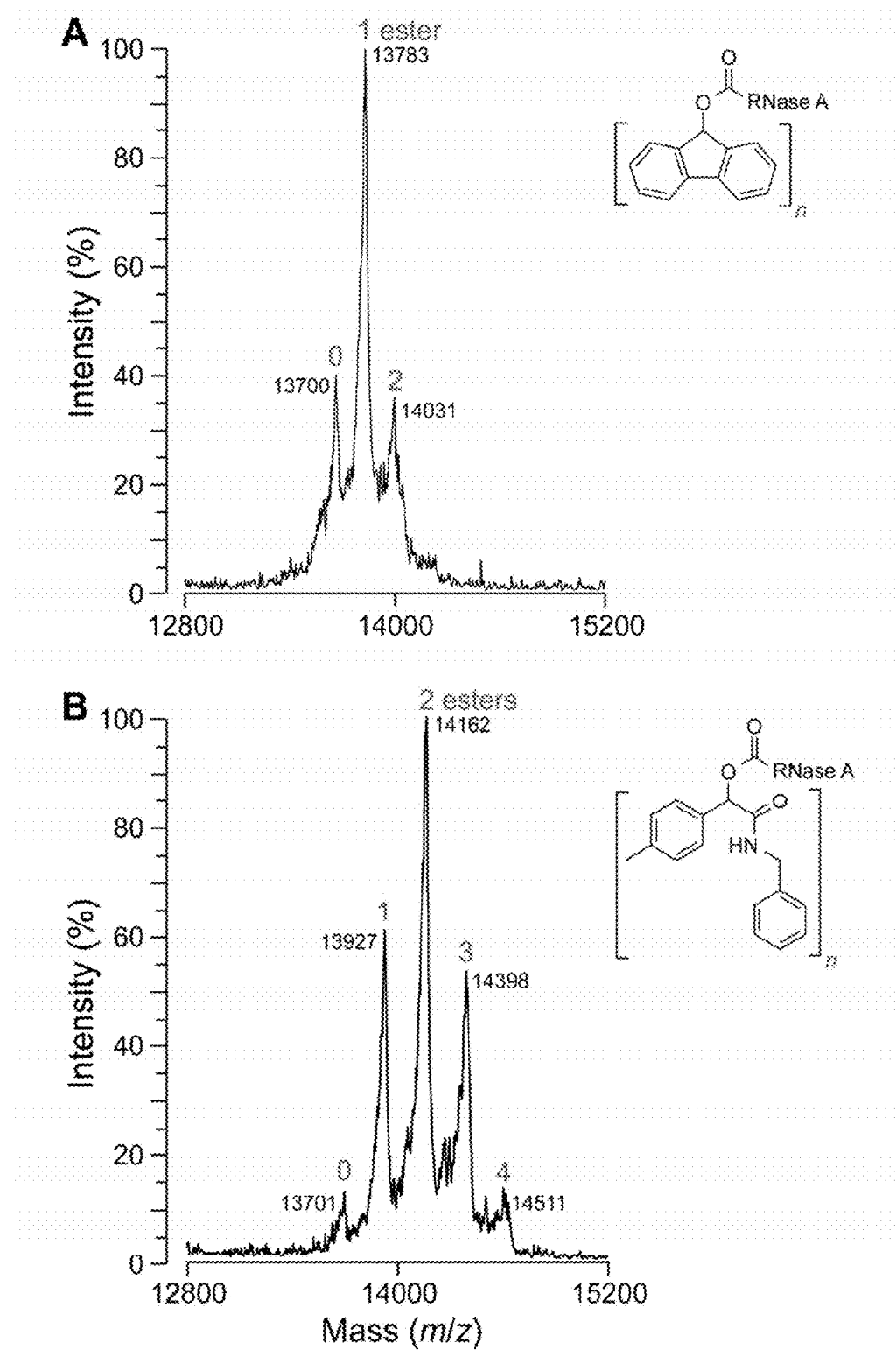
FIG. 5 provides MALDI-TOF mass spectrometry data for esterification of RNase A with (panel A) 9-diazofluorene and (panel B) diazo compound 2.

9-Diazofluorene was prepared as described previously. [5] Yields and spectra matched the published data. Ribonuclease A (0.010 g, 0.73 μmol) was dissolved in 1 mL of 10 mM MES-HCl buffer at pH 5.5. 9-Diazofluorene (0.007 g, 0.036 mmol) was dissolved in 5 mL of CH$_3$CN. A 100-μL aliquot of the diazo stock solution was added to a 100-μL aliquot of the RNase A stock solution. The resulting mixture was mixed by nutation for 4 h at 37° C. Any remaining diazo compound was then quenched by addition of 10 μL of 17.4 M acetic acid. Acetonitrile was removed by concentration under reduced pressure, and the aqueous solution of labeled protein was analyzed by MALDI-TOF mass spectrometry (FIG. 5).

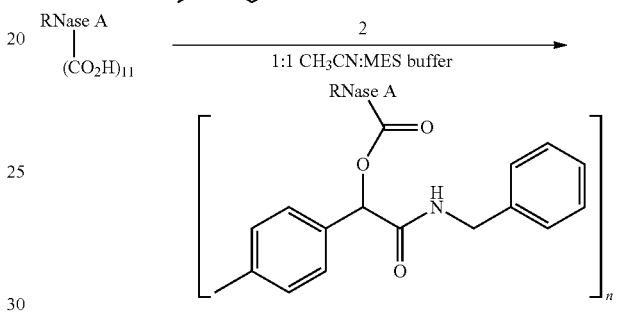

where n indicates the number of esters formed in the protein.

Ribonuclease A (0.010 g, 0.73 μmol) was dissolved in 1 mL of 10 mM MES-HCl buffer at pH 5.5. Diazo compound 2 (0.095 g, 0.036 mmol) was dissolved in 5 mL of CH$_3$CN. A 100-μL aliquot of the diazo stock solution was added to a 100-μL aliquot of the RNase A stock solution. The resulting mixture was mixed by nutation for 4 h at 37° C. Any remaining diazo compound was then quenched by addition of 10 μL of 17.4 M acetic acid. Acetonitrile was removed by concentration under reduced pressure, and the aqueous solution of labeled protein was analyzed by MALDI-TOF mass spectrometry (FIG. 5).

Example 7: Protein Labeling

Angiogenin is used as a model protein to test the efficiency and reversibility of labeling. Treatment of angiogenin with a stoichiometric amount of a diazo-compound of formula 1, particularly compounds 2, 3 and 4 results in the addition of up to 6 labels as determined by MALDI-TOF mass spectrometry (data not shown). Labeled protein is treated with HeLa cell extract, which completely removed all labels demonstrating bioreversibility of labeling.

In a specific example, a stock solution of diazo 3 (19.1 mg, 76 μmol) was prepared by dissolving diazo 3 in 2 mL MeCN. A 200 μL portion of stock solution was added to 200 μL of FLAG-angiogenin (2.9 mg/mL in 10 mM Bis-Tris buffer, pH 6.0). The resulting mixture was nutated for 12 hours at 25° C. The extent of labeling was determined by MALDI-TOF mass spectrometry (data not shown).

A stock solution of diazo 4 (20.4 mg, 76 μmol) was prepared by dissolving diazo 4 in 2 mL MeCN. A 200 μL portion of stock solution was added to 200 μL of FLAG-angiogenin (2.9 mg/mL in 10 mM Bis-Tris buffer, pH 6.0). The resulting mixture was nutated for 12 hours at 25° C. The extent of labeling was determined by MALDI-TOF mass spectrometry (data not shown).

HeLa cell cells were grown to confluence in a 10-cm² dish before collection and lysis using M-PER protein extraction reagent from Thermo Fisher Scientific. Esterase activity was verified by a colorimetric assay using p-nitrophenylacetate. 10 μL of FLAG-angiogenin labeled with either diazo 3 or diazo 4 was added to 10 μL of cell lysate and incubated at 25° C. overnight. FLAG-angiogenin was re-isolated using magnetic Anti-FLAG M2 beads from Sigma-Aldrich. The removal of all labels was confirmed using MALDI-TOF mass spectrometry (data not shown).

Example 8: Ultraviolet Spectra of Diazo Compound 2

Figure 6:
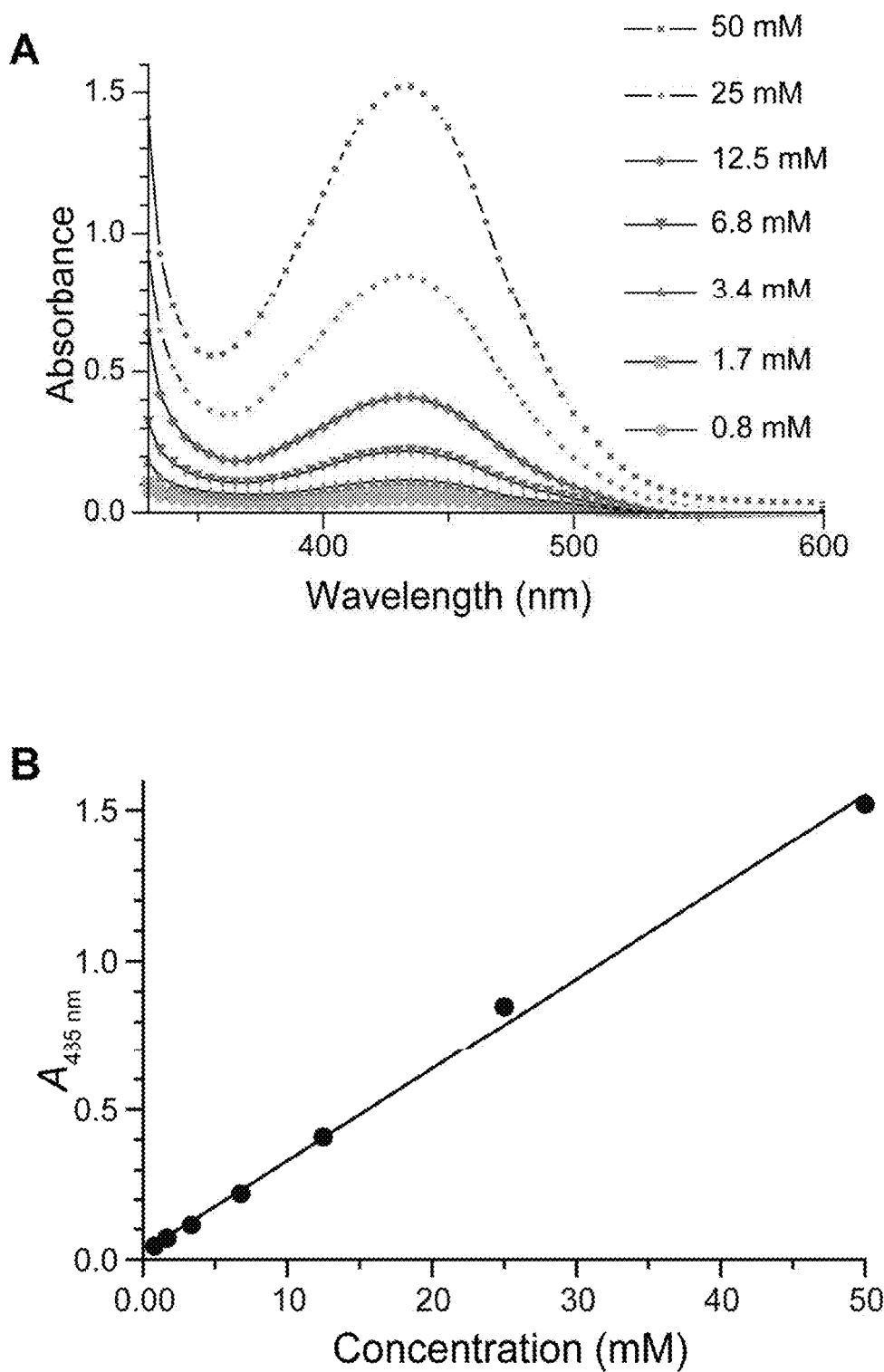
FIG. 6 Illustrates the ultraviolet spectra of diazo compound 2 measured over the concentration range 0.8-50 mM, (panel A). Panel b provides a plot of the concentration dependence of the absorbance of diazo compound 2 (0.8-50 mM) at $\lambda$max=435 nm which gave $\epsilon$=30.5 M-1 cm-1.

The ultraviolet spectra of diazo compound 2 were measured over the concentration range 0.8-50 mM, see FIG. 6, panel A. A plot (FIG. 6, panel B) of the concentration dependence of the absorbance of diazo compound 2 (0.8-50 mM) at $\lambda_{max}$=435 nm, gave $\epsilon$=30.5 M$^{-1}$ cm$^{-1}$.

Example 9: Summary of Results

Diazo compounds 1-6 were accessed from derivatives of phenylacetic acid (FIG. 1, panel B) as described in examples above. Briefly, an azide was installed at the benzylic position of the acid either through displacement of a bromide or by diazo transfer to an existing amine. The ensuing α-azido acids were then coupled to benzylamine and converted to the diazo compound by deimidogenation using a phosphinoester [5a,b].

Figure 2:
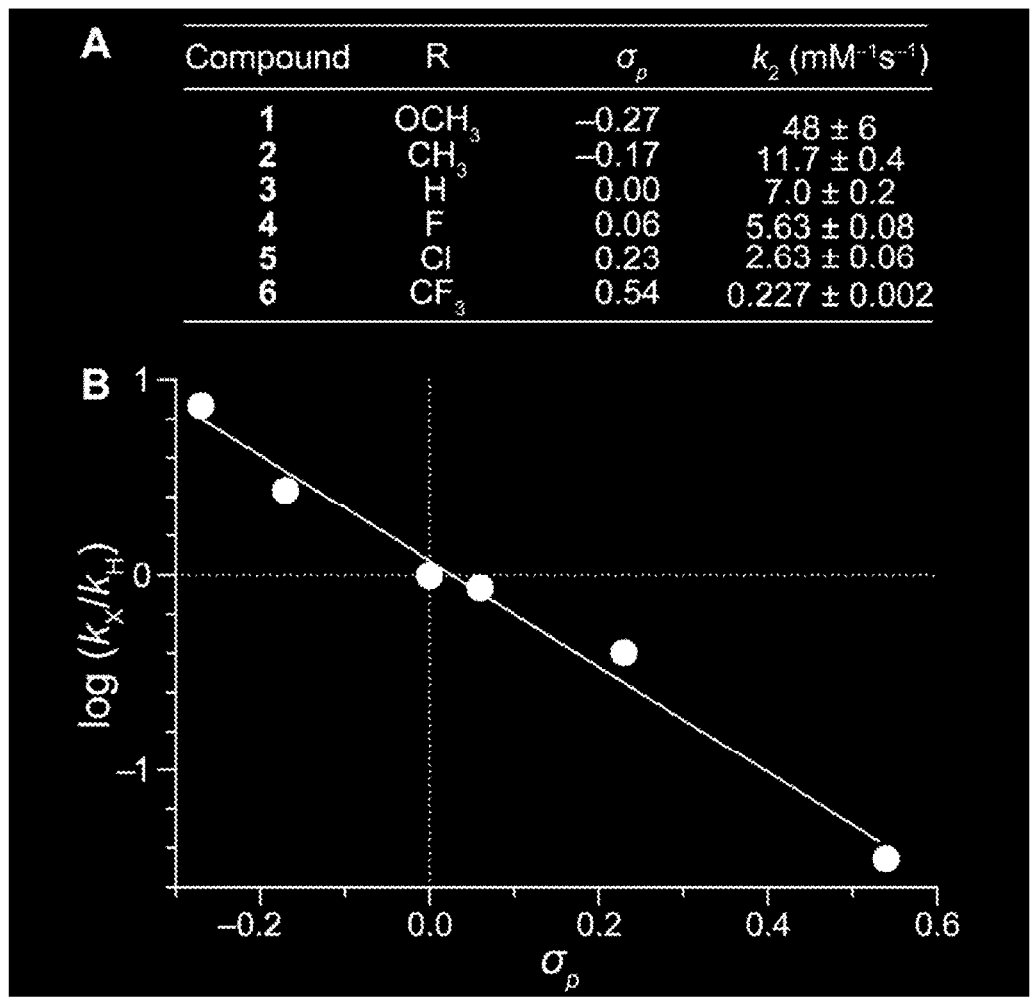
FIG. 2 shows a table of second-order rate constants for the esterification of BocGlyOH by diazo compounds 1-6 in CD$_3$CN in panel A.

In initial experiments, the effect of electron distribution on the reactivity of diazo groups was assessed by measuring the rate of esterification in acetonitrile. Diazo compounds 1-6 were first reacted with BocGlyOH, and the second-order rate constants were measured using ¹H NMR spectroscopy. The effect of electron distribution on the reaction rate was dramatic: rate constants spanned over two orders of magnitude and increased with the electron-donating character of the phenyl substituents (FIG. 2, panel A). Hammett analysis of these rate constants gave a slope of ρ=−2.7 (FIG. 2, panel B). This value is comparable to those for typical SN1 reactions and indicates that the esterification reaction is highly sensitive to substituents and that substantial positive charge accumulates during its course, [33] as expected from a mechanism involving an intermediate diazonium ion (Scheme 1, [27a, b]).

Figure 3:
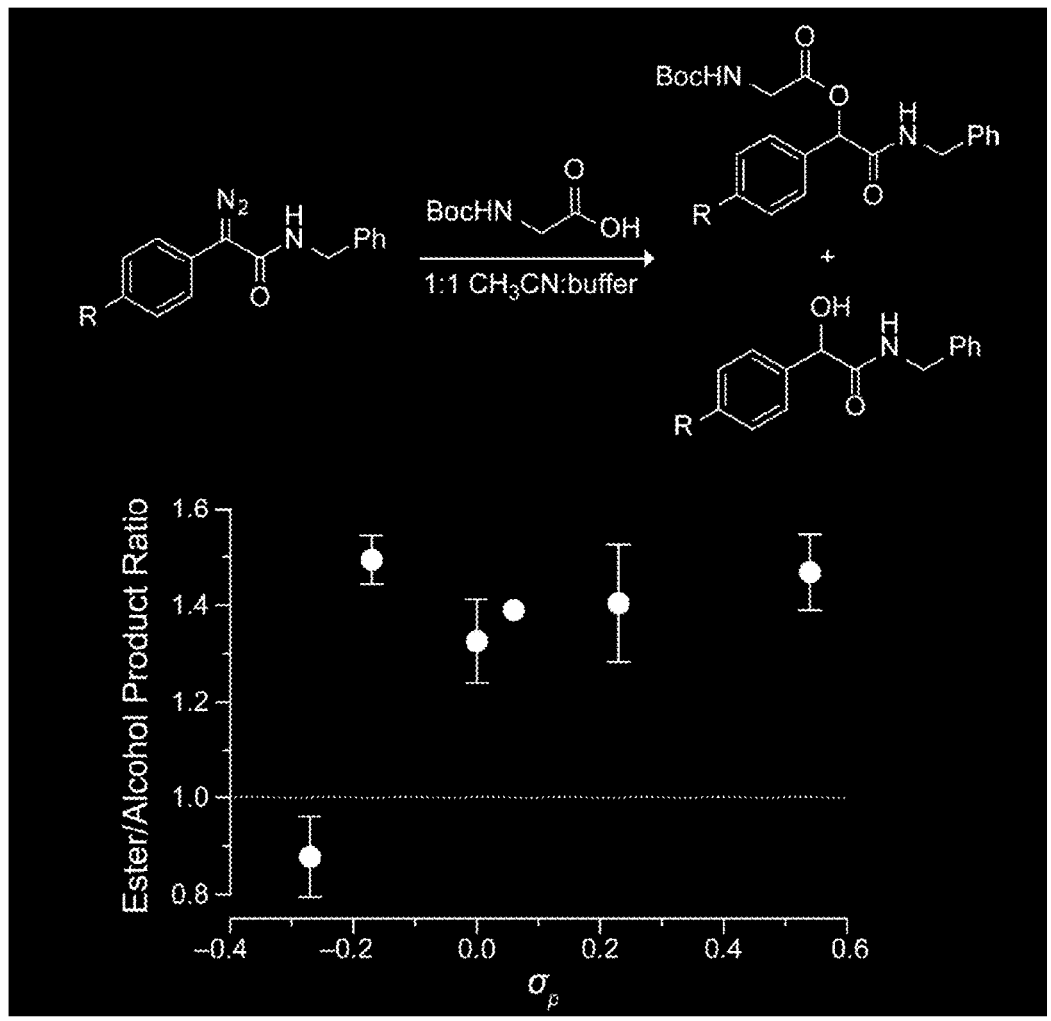
FIG. 3 illustrates the reaction to form ester or alcohol at the top of the figure.
Figure 4:
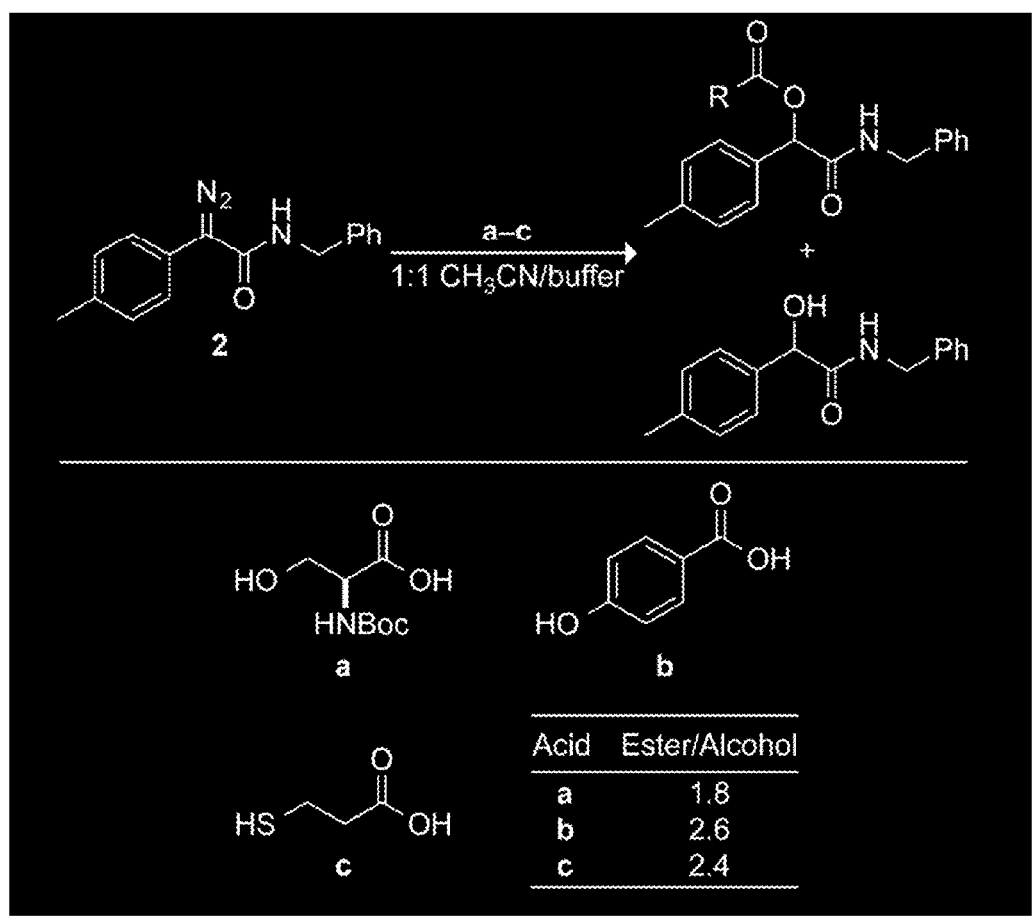
FIG. 4 illustrates the reaction of diazo-compound 2 to form ester or alcohol products with acids a-c at the top of the figure.

Next selectivity for esterification over hydrolysis in an aqueous environment was assessed. Towards that end, diazo compounds 1-6 were reacted with equimolar BocGlyOH in a 1:1 mixture of acetonitrile and 2-(N-morpholino)ethanesulfonic acid (MES)—HCl buffer at pH 5.5, and we determined the ratio of ester-to-alcohol product with ¹H NMR spectroscopy. Surprisingly, the ester:alcohol ratio reached a maximum of 1.4:1 and remained unchanged despite increasing electron-withdrawal by the substituents (FIG. 3). This result is consistent with a sharp cutoff for the formation of a carboxylate.diazonium intimate ion-pair intermediate that is maintained in a solvent cage by a Coulombic interaction (Scheme 1) [27a, b, 34].

Additional experiments were conducted with diazo compound 2 which demonstrated the fastest rate of those compounds that retained chemoselectivity in an aqueous environment. Certain diazo compounds undergo O—H and S—H insertion reactions [23c, 25a,b]. Diazo compound 2 was assessed to determine if it would esterify acids selectively in the presence of the sulfhydryl, hydroxyl, or phenolic moieties found on protein side chains. Diazo compound 2 esterified BocSerOH, p-hydroxybenzoic acid, and 3-mercaptopropionic acid in 1:1 acetonitrile/100 mM MES-HCl buffer at pH 5.5, and that no other coupling products were observable by ¹H NMR spectroscopy.

Additionally, the ability of diazo compound 2 for the labeling of a protein was compared to that of 9-diazofluorene. The well-known model protein ribonuclease A [21] was treated with 10 equiv of each diazo compound. The reactions were allowed to proceed for 4 h at 37° C. in 1:1 acetonitrile/10 mM MES-HCl buffer at pH 5.5. The extent of esterification with both diazo reagents was determined using MALDI-TOF mass spectrometry. Diazo compound 2 was approximately twofold more effective than was 9 diazofluorene in effecting esterification (FIG. 5). Representative diazo compound 2 can be used to esterify proteins in an aqueous environment very efficiently Example 10: Preparation of α-Diazo NHS Ester

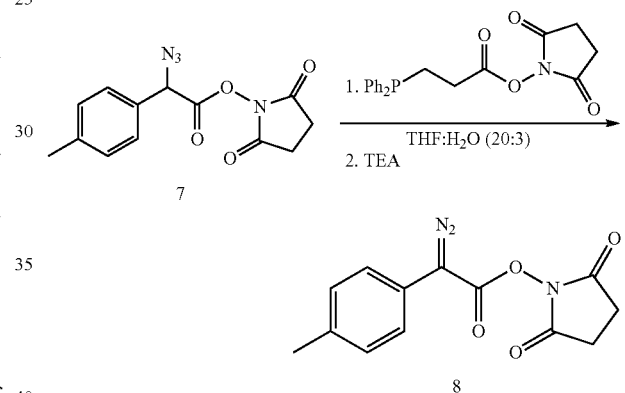

α-Azido-4-methylphenyl N-hydroxysuccinimidyl ester (7) was synthesized as described above. This compound 7 (3.4 g, 11.6 mmol) was dissolved in 20:3 THF/H₂O (50 mL). N-Succinimidyl 3-(diphenylphosphino)propionate (4.5 g, 12.8 mmol) was added under N₂(g), and the reaction mixture was stirred for 5 h. Triethylamine (2.3 g, 23.2 mmol) was added, and the solution was stirred for 1 h. The solution was diluted with brine (20 mL) and extracted with CH₂Cl₂ (2×10 mL). The organic layer was dried over anhydrous Na₂SO₄(s) and concentrated under reduced pressure. The residue was purified by chromatography on silica gel, eluting with 3:7 EtOAc/hexanes to afford α-diazo NHS ester 8 (0.31 g, 10%) as an orange solid.

Data for α-Diazo NHS Ester:

¹H NMR (500 MHz, CDCl₃, δ): 7.32 (d, 2H, J=8.3 Hz), 7.22 (d, 2H, J=8.1 Hz), 2.88 (s, 4H), 2.35 (s, 3H). ¹³C NMR (125 MHz, CDCl₃, δ): 169.4, 160.5, 137.1, 129.9, 124.6, 119.8, 25.6, 21.08 HRMS (ASAP-MS) m/z calcd for C₁₃H₁₁N₃O₄ [M−N₂+H]⁺ 246.0761; found 246.0764.

Compound 8 is an exemplary compound of formula II which can be used to synthesize compounds of formula I.

Example 11: Preparation of Additional α-Diazo Acetamides

A. α-Azido-4-methylphenyl-N-Propargylacetamide

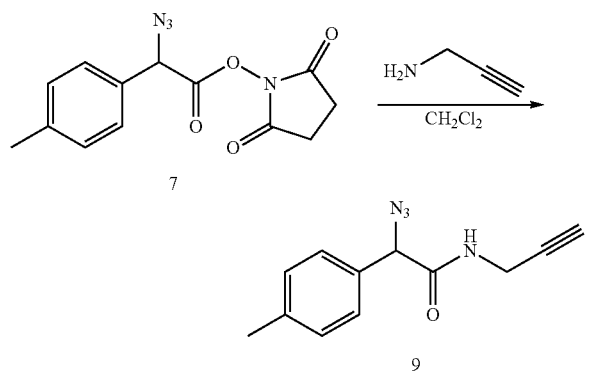

α-Azido-4-methylphenyl N-hydroxysuccinimidyl ester 7 (1.1 g, 3.7 mmol) was dissolved in CH₂Cl₂ (20 mL). Propargylamine (0.2 g, 4.0 mmol) was added, and the reaction mixture stirred overnight. The solution was concentrated under reduced pressure. The residue was dissolved in EtOAc, and washed twice with saturated aqueous NaHCO₃ (2×10 mL). The organic layer was dried over anhydrous Na₂SO₄(s) and concentrated under reduced pressure to afford α-azido-4-methylphenyl-N-propargylacetamide 9 (0.6 g, 75%) as an off-white solid.

Data for α-azido-4-methylphenyl-N-propargylacetamide $^1$H NMR (400 MHz, CDCl₃, δ): 7.25 (d, 2H, J=6.3 Hz), 7.21 (d, 2H, J=8.1 Hz), 6.64 (s, 1H), 5.03 (s, 1H), 4.08 (dd, 2H, J=2.5 Hz, 5.25 Hz), 2.36 (s, 3H), 2.26 (t, 1H, J=2.4 Hz). $^{13}$C NMR (125 MHz, CDCl₃, δ): 167.8, 139.3, 131.6, 129.8, 127.7, 79.9, 72.1, 67.0, 29.4, 21.2. HRMS (ESI⁺) m/z calcd for C₁₂H₁₂N₄O [M+H]⁺ 229.1084; found 229.1085.

B. Preparation of α-Diazo-4-methylphenyl-N-Propargylacetamide

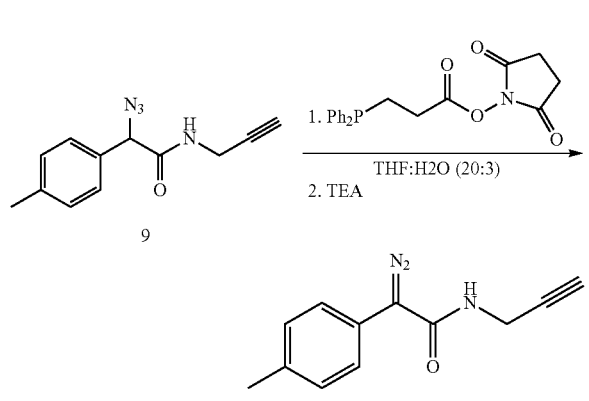

α-Azido-4-methylphenyl-N-propargylacetamide (0.6 g, 2.7 mmol) was dissolved in a solution of 20:3 THF/H₂O (16 mL). N-Succinimidyl 3-(diphenylphosphino)propionate (1.1 g, 3.0 mmol) was added under N₂(g), and the reaction mixture was stirred for 5 h. 1,8-Diazabicycloundec-7-ene (DBU; 0.8 g, 5.5 mmol) was added, and the solution was stirred overnight. The solution was diluted with brine (20 mL) and extracted with CH₂Cl₂ (2×10 mL). The organic layer was dried over anhydrous Na₂SO₄(s) and concentrated under reduced pressure. The residue was purified by chromatography on silica gel, eluting with 3:7 EtOAc/hexanes to afford α-diazo-N-propargylacetamide (0.176 g, 30%) as a red solid.

Data for α-diazo-4-methylphenyl-N-propargylacetamide $^1$H NMR (500 MHz, CDCl₃, δ): 7.28-7.24 (m, 4H), 5.52 (s, 1H), 4.15-4.14 (dd, 2H, J=2.5, 5.4 Hz), 2.38 (s, 3H), 2.23 (s, 1H). $^{13}$C NMR (125 MHz, CDCl₃, δ): 164.9, 138.3, 130.5, 128.0, 122.6, 79.6, 71.6, 64.0, 29.7, 21.2. HRMS (ESI⁺) m/z calcd for C₁₂H₁₁N₃O [M+H]⁺ 214.0975; found 214.0975.

Example 12: Preparation of Compounds of Formula I Using Compounds of Formula II

A. α-Diazo-4-methylphenyl-N-Methylacetamide

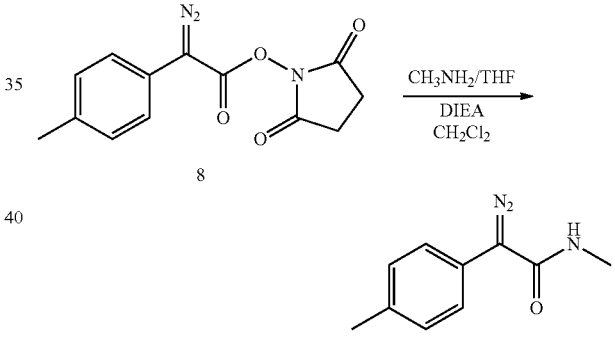

α-Diazo NHS ester 8 (100 mg, 0.37 mmol) was dissolved in CH₂Cl₂ (37 mL). Methylamine (0.2 mL of a 2.0 M solution in THF; 0.41 mmol) and N,N-diisopropylethylamine (DIEA; 143 mg, 1.1 mmol) were added, and the reaction mixture was stirred overnight. The solution was concentrated under reduced pressure, and the residue was dissolved in EtOAc. The residue was purified by chromatography on silica gel, eluting with 3:7 EtOAc/hexanes to afford α-diazo-4-methyphenyl-N-methylacetamide (34 mg, 49%) as a red solid.

Data for α-diazo-4-methylphenyl-N-methylacetamide $^1$H NMR (500 MHz, CDCl₃, δ): 7.26-7.25 (m, 4H), 5.36 (s, 1H), 2.90 (d, 3H, J=4.8 Hz), 2.37 (s, 3H). $^{13}$C NMR (125 MHz, CDCl₃, δ): 165.8, 138.0, 130.4, 127.9, 123.2, 63.7, 27.0, 21.2. HRMS (ESI⁺) m/z calcd for C₁₀H₁₁N₄O [M−N₂+H]⁺ 162.0913; found 162.0915.

B. Preparation of α-Diazo-4-methylphenyl-N,N-Dimethylacetamide

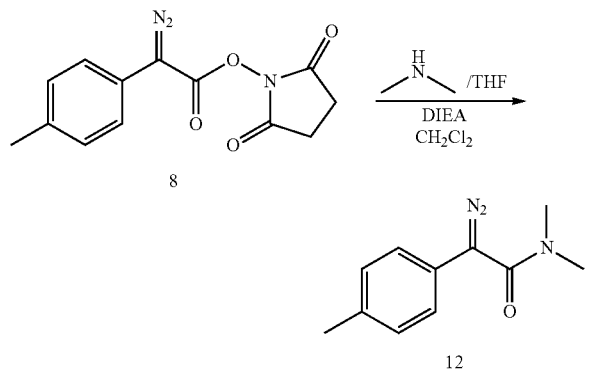

α-Diazo NHS ester 8 (100 mg, 0.37 mmol) was dissolved in CH$_2$Cl$_2$ (37 mL). Dimethylamine (0.2 mL of a 2.0 M solution in THF; 0.41 mmol) and DIEA (143 mg, 1.1 mmol) were added, and the reaction mixture was stirred overnight. The solution was concentrated under reduced pressure, and the residue was dissolved in EtOAc. The residue was purified by chromatography on silica gel, eluting with 3:7 EtOAc/hexanes to afford α-diazo-4-methylphenyl-N,N-dimethyl acetamide (24 mg, 32%) as a red solid.

Data for α-diazo-N,N-dimethylacetamide $^1$H NMR (500 MHz, CDCl$_3$, δ): 7.19 (d, 2H, J=8.1 Hz), 7.11 (d, 2H, J=8.3 Hz), 2.95 (s, 6H), 2.34 (s, 3H). $^{13}$C NMR (125 MHz, CDCl$_3$, δ): 166.1, 135.6, 129.9, 124.7, 124.4, 62.4, 37.8, 21.0. HRMS (ESI$^+$) m/z calcd for C$_{11}$H$_{13}$N$_3$O [M−N$_2$+H]$^+$ 176.1070; found 176.1071.

C. Preparation of α-Diazo-4-methylphenyl-N-pentylacetamide

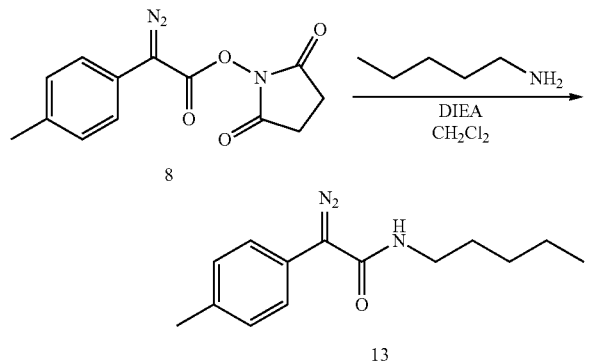

α-Diazo NHS ester 8 (100 mg, 0.37 mmol) was dissolved in CH$_2$Cl$_2$ (37 mL). Pentylamine (35.4 mg, 0.41 mmol) and DIEA (143 mg, 1.1 mmol) were added, and the reaction mixture was stirred overnight. The solution was concentrated under reduced pressure, and the residue was dissolved in EtOAc. The residue was purified by chromatography on silica gel, eluting with 1:4 EtOAc/hexanes to afford α-diazo-4-methylphenyl-N-pentylacetamide (65 mg, 72%) as a red solid.

Data for α-Diazo-4-methylphenyl-N-pentylacetamide $^1$H NMR (500 MHz, CDCl$_3$, δ): 7.26-7.23 (m, 4H), 5.37 (s, 1H), 3.36-3.32 (q, 2H, J=7.0 Hz), 2.38 (s, 3H), 1.53-1.49 (m, 2H), 1.33-1.28 (m, 4H), 0.90-0.88 (t, 3H, J=6.9 Hz). $^{13}$C NMR (125 MHz, CDCl$_3$, δ): 164.9, 137.9, 130.4, 127.8, 123.3, 63.8, 40.2, 29.6, 29.0, 22.3, 21.2, 14.0. HRMS (ESI$^+$) m/z calcd for C$_{14}$H$_{19}$N$_3$O [M−N$_2$+H]$^+$ 218.1539; found 218.1541.

Example 13: Esterification of Proteins and Internalization

Figure 7:
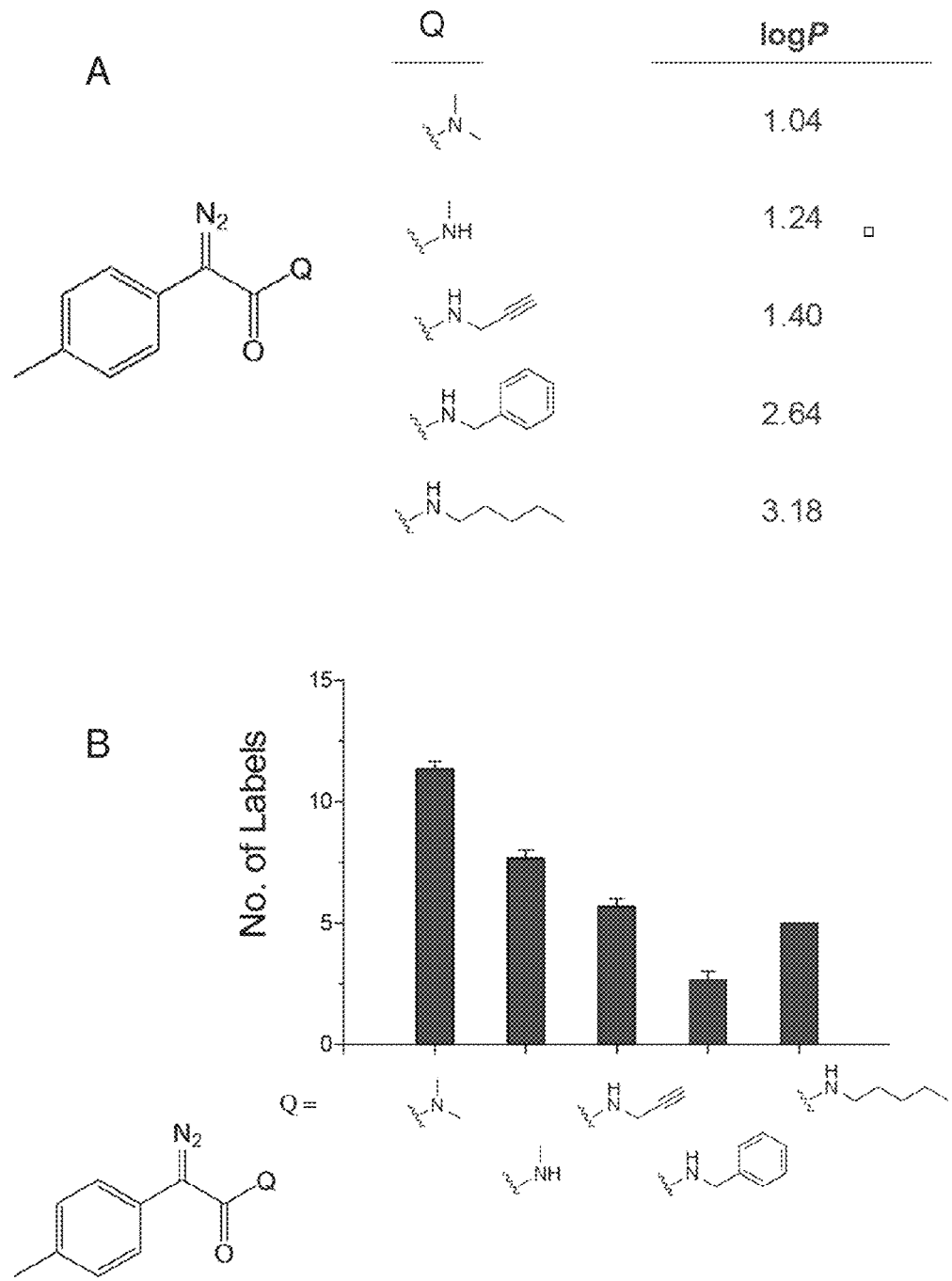
FIG. 7 reports quantification of labeling efficiency of GFP by certain diazo compounds. Panel A shows the compound structure and log P for certain diazo compounds.

GFP was esterified as described above with five exemplary diazo compounds 2, 10-13 (FIG. 7, Panel A). The GFP variant used in these experiments and its production were described previously [24]. Using mass spectrometry, an average of ~3-11 labels per protein were found (FIG. 7, Panel B). Less polar diazo compounds tended to provide more extensive labeling.

Figure 8:
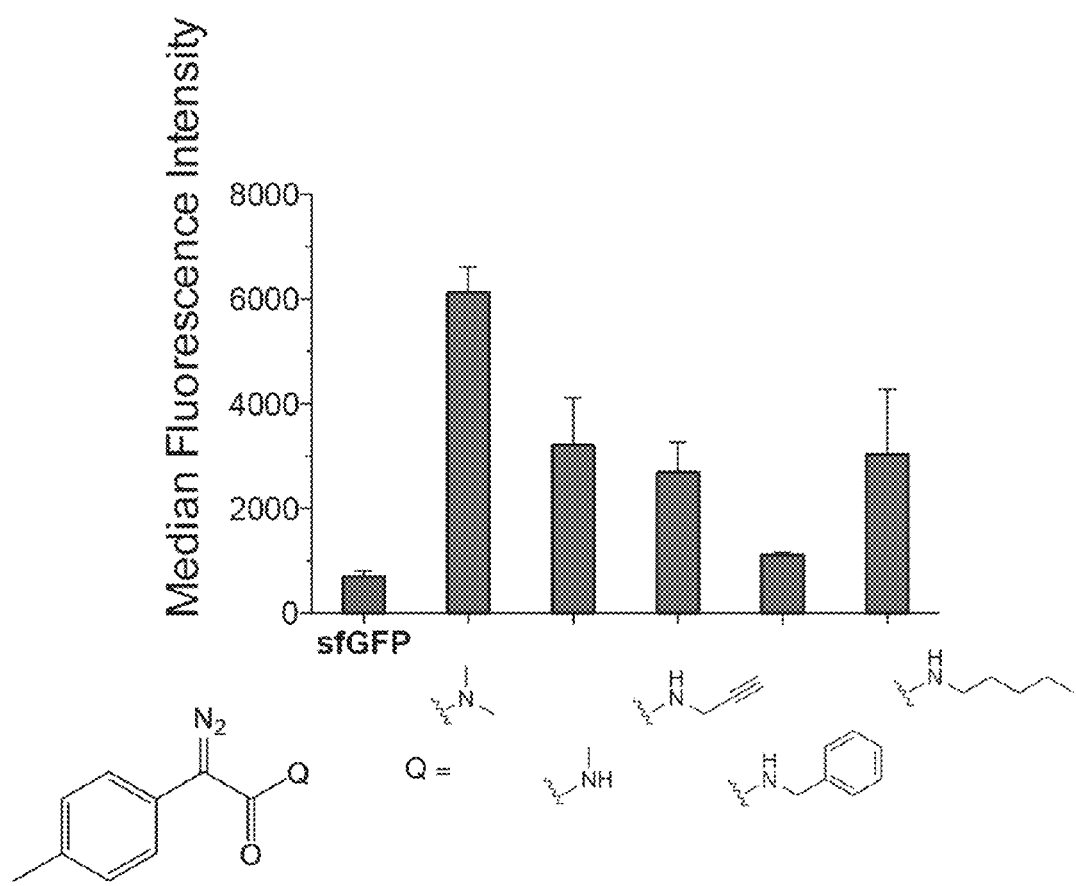
FIG. 8 is a graph showing quantification of internalization of labeled versus unlabeled GFP by CHO K1 cells using flow cytometry measuring median fluorescence intensity. Single cells were sorted based on forward scatter-side scatter measurements, and live cells were sorted using 7AAD (7-amino-actinomycin D) stain.
Figure 9:
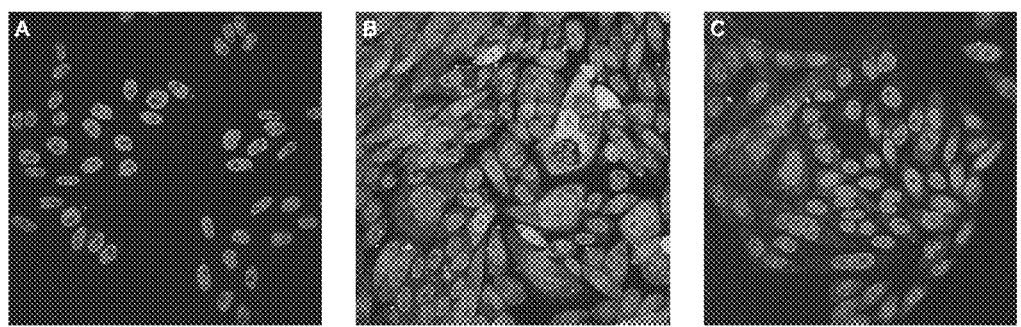
FIG. 9 illustrates microscopy images of uptake of esterified GFP (green) by CHO K1 cells. (panel A) Not esterified. (panel B) Esterified with α-diazo-4-methylphenyl-N-propargylacetamide 10 (panel C) Esterified with α-diazo-4-methylphenyl-N,N-dimethylacetamide. Cell nuclei are stained with Hoechst 33342 (blue).

Chinese hamster ovary (CHO) K1 cells were incubated at 37° C. for 2 h in F-12K medium (which was supplemented with penicillin/streptomycin) containing either unlabeled or labeled GFP (15 μM). Internalization of GFP was then quantified with flow cytometry, counting only live, single cells, as shown in FIG. 8. More extensively labeled GFPs tended to be internalized more efficiently. Individual cells were imaged by confocal microscopy for two of the diazo compounds. Esterification with either diazo compound 11 or 12 enhanced the uptake of GFP into CHO K1 cells, as shown in FIG. 9. The images shown demonstrate that the labelled proteins are inside of the cell.

These data indicate that protein internalization is enhanced by forming esters with the diazo compounds of the invention.

One barrier to cellular entry of a protein into a cell is the Coulombic repulsion between negatively charged amino acid residues on the protein and negatively charged cell membrane components. Without wishing to be bound by any particular theory it is presently believed based on the results of FIGS. 8 and 9 that masking of negative charges on a protein by esterification facilitates cell penetration.

REFERENCES (1) Trost, B. M. *Science* 1983, 219, 245.
(2) Trost, B. M.; Salzmann, T. N. *J. Am. Chem. Soc.* 1973, 95, 6840.
(3) Yamamoto, Y.; Toi, H.; Sonoda, A.; Murahashi, S. I. *J. Am. chem. Soc.* 1976, 98, 1965.
(4) McGrath, N. A.; Raines, R. T. *Chem. Sci.* 2012, 3, 3237.
(5) (a) Myers, E. L.; Raines, R. T. *Angew. Chem. Int. Ed.* 2009, 48, 2359; (b) Chou, H.-H.; Raines, R. T. *J. Am. Chem. Soc.* 2013, 135, 14936-14939.
(6) Chibnall, A. C.; Mangan, J. L.; Rees, M. W. *Biochem. J.* 1958, 68, 114.
(7) Tian, L.; Yang, Y.; Wysocki, L. M.; Arnold, A. C.; Hu, A.; Ravichandran, B.; Sternson, S. M.; Looger, L. L.; Lavis, L. D. *P. Natl. Acad. Sci. USA* 2012, 109, 4756.
(8) Boyce, M.; Bertozzi, C. R. *Nat Methods* 2011, 8, 638.
(9) Ye, T.; McKervey, M. A. *Chem. Rev.* 1994, 94, 1091.
(10) Doyle, M. P. *Chem. Rev.* 1986, 86, 919.
(11) Bertelsen, S.; Nielsen, M.; Bachmann, S.; Jorgensen, K. A. *Synthesis-Stuttgart* 2005, 2234.
(12) Shinada, T.; Kawakami, T.; Sakai, H.; Takada, I.; Ohfune, Y. *Tetrahedron Lett.* 1998, 39, 3757.

(13) Dumitrescu, L.; Azzouzi-Zriba, K.; Bonnet-Delpon, D.; Crousse, B. *Org. Lett.* 2011, 13, 692.
(14) De, K.; Legros, J.; Crousse, B.; Bonnet-Delpon, D. *J. Org. Chem.* 2009, 74, 6260.
(15) Furrow, M. E.; Myers, A. G. *J. Am. Chem. Soc.* 2004, 126, 12222.
(16) Riehm, J. P.; Scheraga, H. A. *Biochemistry* 1965, 4, 772.
(17) Delpierre, G. R.; Fruton, J. S. *P. Natl. Acad. Sci. USA* 1965, 54, 1161.
(18) Doscher, M. S.; Wilcox, P. E. *J. Biol. Chem.* 1961, 236, 1328.
(19) Grossberg, A. L.; Pressman, D. *J. Am. Chem. Soc.* 1960, 82, 5478.
(20) Lázníček, M.; Lázníčková, A. *J. Pharmaceut. Biomed.* 1995, 13, 823.
(22) F. G. Bordwell (1988) Acc. Chem. Res. 21, 456, 463. A Table of pKa data of acidity of various organic compounds in DMSO is found at the web site chem.wisc.edu/areas/reich/pkatable/; F. G. Bordwell et al. J. Am. Chem. Soc. 1975, 97, 7006; F. G. Bordwell et al. J. Org. Chem. 1980, 45, 3325; F. G. Bordwell et al. J. Org. Chem. 1981, 46, 632; F. G. Bordwell et al. J. Am. Chem. Soc. 1983, 105, 6188; F. G. Bordwell et al. J. Org. Chem. 1990, 55, 3330; F. G. Bordwell et al. J. Org. Chem. 1991, 56, 4218; F. G. Bordwell et al. Can. J. Chem. 1990, 68, 1714.
(23) (a) Regitz, M.; Maas, G. Diazo Compounds: Properties and Synthesis; Academic Press: London, 1986. (b) Padwa, A.; Weingarten, M. D. Chem. Rev. 1996, 96, 223-269. (c) Doyle, M. P.; McKervey, M. A.; Ye, T. Modern Catalytic Methods for Organic Synthesis with Diazo Compounds; Wiley: New York, N.Y., 1998. (d) Davies, H. M. L.; Beckwith, R. E. J. Chem. Rev. 2003, 103, 2861-2904. (e) Candelas, N. R.; Alfonso, C. A. Curr. Org. Chem. 2009, 13, 763-787.
(24) Andersen, K. A.; Aronoff, M. R.; McGrath, N. A.; Raines, R. T. J. Am. Chem. Soc. 2015, 137, 2412-2415.
(25) (a) Antos, J. M.; Francis, M. B. J. Am. Chem. Soc. 2004, 126, 10256-10257. (b) Antos, J. M.; McFarland, J. M.; Lavarone, A. T.; Francis, M. B. J. Am. Chem. Soc. 2009, 131, 6301-6308.
(26) (a) Testa, B.; Mayer, J. M. Hydrolysis in Drug and Prodrug Metabolism; Verlag Helvetica Chimica Acta: Zurich, Switzerland, 2003. (b) Liederer, B. M.; Borchardt, R. T. J. Pharm. Sci. 2006, 95, 1177-1195. (c) Lavis, L. D. ACS Chem. Biol. 2008, 3, 203-206.
(27) (a) Roberts, J. D.; Watanabe, W.; McMahon, R. E. J. Am. Chem. Soc. 1951, 73, 760-765. (b) Roberts, J. D.; Watanabe, W.; McMahon, R. E. J. Am. Chem. Soc. 1951, 73, 2521-2523.
(28) (a) Doscher, M. S.; Wilcox, P. E. J. Biol. Chem. 1961, 236, 1328-1337. (b) Riehm, J. P.; Sheraga, H. A. Biochemistry 1965, 4, 772-782. (c) Delpierre, G. R.; Fruton, J. S. Proc. Natl. Acad. Sci. USA 1965, 54, 1161-1167.
(29) Goddard-Borger, E. D., Stick, R. V. Org. Lett 2007, 9, 3797.
(30) Harris, J. M.; Chess, R. B. Nat. Rev. Drug Discov. 2003, 2, 214-221.
(31) (a) Hammett, L. P. Chem. Rev. 1935, 17, 125-136. (b) Hammett, L. P. J. Am. Chem. Soc. 1937, 59, 96-103. (c) Hammett, L. P. In Physical Organic Chemistry; McGraw-Hill: New York, N.Y., 1940, pp 184-228. (d) Shorter, J. Chem. Listy 2000, 94, 210-214.
(32) Hansch, C.; Leo, A.; Taft, R. W. Chem. Rev. 1991, 91, 165-175.
(33) Anslyn, E. V.; Doughertry, D. A. Modern Physical Organic Chemistry; University Science Books: Sausalito, Calif., 2006.
(34) Szele, I.; Tencer, M.; Zollinger, H. Helv. Chim. Acta 1983, 66, 1691-1703.
(35) Chames, P. Van Regenmortel, M. Weiss, E. & Baty, D. Therapeutic antibodies: successes, limitations and hopes for the future. Br J Pharmacol. 2009 May; 157(2): 220-233.
(36) Maiese, K.; Chong, Z. Z.; Shang, Y. C.; Hou, J. L. "FOXO" in sight: Targeting Foxo proteins from conception to cancer" *Med. Res. Rev.* 2009, 29, 395-418.
(37) Martin-Belmonte, F.; Perez-Moreno, M. *Nat. Rev. Cancer* 2012, 12, 23-38.
(38) Srinivasarao, M. et al. (2015) Nature Reviews/Drug Discovery 14:203-219.
(39) Josa-Cullere, I. et al. (2014) RSC Advances 4:52241.
(40) Ma, M. et al. (2005) J. Am. Chem. Soc. 127(43) 15016-15017.

We claim:

1. A compound of formula I:

$$\underset{R_A}{\text{Ph}}\!-\!\overset{N_2}{\underset{O}{C}}\!-\!\overset{R}{\underset{}{C(=O)}}\!-\!N(R)(R_M)$$

or salts thereof,
where:
R is an alkyl, alkenyl, alkynyl group or hydrogen,
$R_A$ is an alkyl or alkoxy at the para position on the indicated phenyl ring, and
$R_M$ is an alkyl, alkenyl, alkynyl, cycloalkyl, aryl, or arylalkyl group which is optionally substituted with one or more alkyl, alkoxy, aryl, alkylaryl, halogen, haloalkyl, or haloalkoxy groups.

2. The compound of claim 1, wherein $R_M$ is an alkyl, alkenyl, alkynyl, phenyl or benzyl group.

3. The compound of claim 1, wherein $R_A$ is an alkyl group having 1-6 carbon atoms in the para position on the phenyl ring.

4. The compound of claim 1, wherein $R_A$ is a methyl group in the para position on the phenyl ring.

5. The compound of claim 1, wherein $R_M$ is an alkyl group having 1-6 carbon atoms or an alkynyl group having 2-6 carbon atoms.

6. The compound of claim 5, wherein $R_A$ is an alkyl group substituted at the para position on the phenyl ring.

7. The compound of claim 6, wherein R is hydrogen or a methyl group.

8. The compound of claim 1, wherein $R_M$ is an alkyl group having 1-6 carbon atoms.

9. The compound of claim 8, wherein $R_A$ is an alkyl group substituted at the para-position of the phenyl ring.

10. The compound of claim 9, wherein R is hydrogen or a methyl group.

11. The compound of claim 1, wherein $R_A$ is a methyl group substituted at the para position of the phenyl ring.

12. The compound of claim 11, wherein R and $R_M$ are methyl or ethyl groups.

13. The compound of claim 12, wherein R and $R_M$ are both methyl groups.

14. The compound of claim 1, wherein $R_M$ is an alkyl, or benzyl group.

15. The compound of claim 14, wherein R is hydrogen, or an alkyl group.

16. The compound of claim 15, wherein $R_A$ is an alkyl group at the para position of the phenyl ring.

17. The compound of claim 15, wherein $R_A$ is a methyl group at the para position of the phenyl ring.

* * * * *

UNITED STATES PATENT AND TRADEMARK OFFICE
CERTIFICATE OF CORRECTION

| | | |
|---|---|---|
| PATENT NO. | : 9,790,483 B2 | Page 1 of 1 |
| APPLICATION NO. | : 15/093510 | |
| DATED | : October 17, 2017 | |
| INVENTOR(S) | : Ronald T. Raines and Kalie Mix | |

It is certified that error appears in the above-identified patent and that said Letters Patent is hereby corrected as shown below:

Column 1, Lines 15-18, please replace the whole paragraph, "This invention was made with government support under GM044783 and GM007215 awarded by the National Institutes of Health. The government has certain rights in the invention." with --This invention was made with government support under GM044783 awarded by the National Institutes of Health. The government has certain rights in the invention.--

Signed and Sealed this
Fifth Day of December, 2017

Joseph Matal
*Performing the Functions and Duties of the
Under Secretary of Commerce for Intellectual Property and
Director of the United States Patent and Trademark Office*